United States Patent
Neamati et al.

(10) Patent No.: US 10,457,662 B2
(45) Date of Patent: Oct. 29, 2019

(54) SUBSTITUTED AMIDES FOR TREATING AND PREVENTING CANCER

(71) Applicants: The Regents of the University of Michigan, Ann Arbor, MI (US); The Board of Regents of The University of Texas System, Austin, TX (US)

(72) Inventors: Nouri Neamati, Ann Arbor, MI (US); Jia Zhou, Austin, TX (US); Yuting Kuang, Ann Arbor, MI (US); Na Ye, Austin, TX (US)

(73) Assignees: The Regents of the University of Michigan, Ann Arbor, MI (US); The Board of Regents of the University of Texas System, Austin, TX (US)

( * ) Notice: Subject to any disclaimer, the term of this patent is extended or adjusted under 35 U.S.C. 154(b) by 0 days.

(21) Appl. No.: 15/575,676

(22) PCT Filed: May 20, 2016

(86) PCT No.: PCT/US2016/033540
§ 371 (c)(1),
(2) Date: Nov. 20, 2017

(87) PCT Pub. No.: WO2016/187544
PCT Pub. Date: Nov. 24, 2016

(65) Prior Publication Data
US 2018/0282296 A1    Oct. 4, 2018

Related U.S. Application Data

(60) Provisional application No. 62/164,286, filed on May 20, 2015.

(51) Int. Cl.
| | | |
|---|---|---|
| *A61K 31/165* | (2006.01) |
| *C07C 233/64* | (2006.01) |
| *C07D 401/04* | (2006.01) |
| *A61K 31/4706* | (2006.01) |
| *A61K 31/497* | (2006.01) |
| *A61K 31/501* | (2006.01) |
| *A61K 31/506* | (2006.01) |
| *C07D 215/40* | (2006.01) |
| *C07D 401/14* | (2006.01) |
| *C07D 401/12* | (2006.01) |
| *C07D 239/28* | (2006.01) |
| *C07D 241/24* | (2006.01) |
| *C07D 471/04* | (2006.01) |
| *A61K 31/4709* | (2006.01) |
| *A61K 31/498* | (2006.01) |
| *A61K 31/5377* | (2006.01) |
| *A61K 45/06* | (2006.01) |

(52) U.S. Cl.
CPC ........ *C07D 401/04* (2013.01); *A61K 31/4706* (2013.01); *A61K 31/4709* (2013.01); *A61K 31/497* (2013.01); *A61K 31/498* (2013.01); *A61K 31/501* (2013.01); *A61K 31/506* (2013.01); *A61K 31/5377* (2013.01); *A61K 45/06* (2013.01); *C07D 215/40* (2013.01); *C07D 239/28* (2013.01); *C07D 241/24* (2013.01); *C07D 401/12* (2013.01); *C07D 401/14* (2013.01); *C07D 471/04* (2013.01)

(58) Field of Classification Search
CPC ........................... A61K 31/165; C07C 233/64
USPC .......................................... 514/613; 564/123
See application file for complete search history.

(56) References Cited

U.S. PATENT DOCUMENTS

| | | |
|---|---|---|
| 6,218,393 B1 | 4/2001 | Ryder et al. |
| 8,420,647 B2 | 4/2013 | Bissantz et al. |
| 2015/0065436 A1 | 3/2015 | Arora et al. |

FOREIGN PATENT DOCUMENTS

| | | |
|---|---|---|
| WO | 2000/012498 | 3/2000 |
| WO | 2007/048070 | 4/2007 |
| WO | 2010/037129 | 4/2010 |
| WO | 2013/122609 | 8/2013 |

OTHER PUBLICATIONS

Jordan, V. C. Nature Reviews: Drug Discovery, 2, 2003, 205.*
Vippagunta, et al. Advanced Drug Delivery Reviews, 48, 2001, 18.*
Wolff, Manfred E., Ed. Burger's Medicinal Chemistry and Drug Discovery—Fifth Edition, vol. 1: Principles and Practice, New York: John Wiley & Sons, 1994, 975-977.*
Kim, et al. Inorganic Chemistry, 46(21), 2007, 8481-8483.*
Kim, et al. Inorganic Chemistry, 46(25), 2007, 10461-10463.*
Al-Lazikani B, et al. "Combinatorial drug therapy for cancer in the post-genomic era." (2012) Nature biotechnology 30(7): 679-692.

(Continued)

*Primary Examiner* — Douglas M Willis
(74) *Attorney, Agent, or Firm* — Casimir Jones, S.C.; Robert A. Goetz

(57) ABSTRACT

This invention is in the field of medicinal chemistry. In particular, the invention relates to novel small molecule compounds having a quinolin-8-yl-nicotinamide structure (e.g., a compound having Formula I:

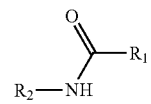

which are useful in treating, ameliorating, or preventing various forms of cancer (e.g., pancreatic cancer).

12 Claims, 12 Drawing Sheets

(56) References Cited

OTHER PUBLICATIONS

Baek SJ, et al., "Epicatechin gallate-induced expression of NAG-1 is associated with growth inhibition and apoptosis in colon cancer cells." (2004) Carcinogenesis 25(12): 2425-2432.
Bottone FG, Jr., et al. "Gene Modulation by the Cyclooxygenase Inhibitor, Sulindac Sulfide, in Human Colorectal Carcinoma Cells" (2003) The Journal of biological chemistry 278(28): 25790-25801.
CJ OC, et al., "Diversity-oriented synthesis: producing chemical tools for dissecting biology." (2012) Chemical Society reviews 41(12): 4444-4456.
Dawson JC, et al. "Quantitative phenotypic and pathway profiling guides rational drug combination strategies" (2014) Frontiers in pharmacology 5: 118.
Deretic V, et al. "Autophagy in infection, inflammation and immunity." (2013) Nature reviews. Immunology 13(10): 722-737.
Din FV, et al., "Aspirin inhibits mTOR signaling, activates AMP-activated protein kinase, and induces autophagy in colorectal cancer cells." (2012) Gastroenterology 142(7): 1504-1515 e1503.
Dombroski BA, et al., "Gene Expression and Genetic Variation in Response to Endoplasmic Reticulum Stress in Human Cells" (2010) American journal of human genetics 86(5): 719-729.
Dutertre M, et al., "Estrogen Regulation and Physiopathologic Significance of Alternative Promoters in Breast Cancer" (2010) Cancer research 70(9): 3760-3770.
Hai T, Hartman MG "The molecular biology and nomenclature of the activating transcription factor/cAMP responsive element binding family of transcription factors: activating transcription factor proteins and homestasis" (2001) Gene 273(1): 1-11.
Huang S, "Celecoxib-induced apoptosis is enhanced by ABT-737 and by inhibition of autophagy in human colorectal cancer cells" (2010) Autophagy 6(2): 256-269.
Hutchinson L. Kirk R "High drug attrition rates—where are we going wrong?" (2011) Nature reviews. Clinical oncology 8(4): 189-190.
International Search Report, International Patent Application No. PCT/US2016/033540, dated Aug. 30, 2016, 7 pages.
Joseph SB, et al., "Synthetic LXR ligand inhibits the development of atherosclerosis in mice." (2002) Proceedings of the National Academy of Sciences of the United States of America 99(11): 7604-7609.
Kaileh M, et al., "Withaferin A Strongly Elicits IκB Kinase β Hyperphosphorylation Concomitant with" (2007) The Journal of biological chemistry 282(7): 4253-4264.
Kim JM, et al., "NAG-1/GDF15 transgenic mouse has less white adipose tissue and a reduced inflammatory response." (2013) Mediators of inflammation 2013: 641851.
Kroemer G, et al. "Autophagy and the integrated stress response." (2010) Molecular cell 40(2): 280-293.
Lee SH, et al., "Indole-3-carbinol and 3,3'-diindolylmethane induce expression of NAG-1 in a p53-independent manner." (2005) Biochemical and biophysical research communications 328(1): 63-69.
Lee SH, et al., "Conjugated linoleic acid stimulates an antitumorigenic protein NAG-1 in an isomer specific manner." (2006) Carcinogenesis 27(5): 972-981.
Lee SH, et al. "NSAID-activated gene-1 as a molecular target for capsaicin-induced apoptosis through a novel molecular mechanism involving GSK3beta, C/EBPbeta and ATF3." (2010) Carcinogenesis 31(4): 719-728.
Leik CE, et al., "GW3965, a synthetic liver X receptor (LXR) agonist, reduces angiotensin II-mediated pressor responses in Sprague—Dawley rats" (2007) British journal of pharmacology 151(4): 450-456.
Li PX, , et al. "Placental transforming growth factor-beta is a downstream mediator of the growth arrest and apoptotic response of tumor cells to DNA damage and p53 overexpression." (2000) The Journal of biological chemistry 275(26): 20127-20135.
Liu T, et al., "Macrophage Inhibitory Cytokin 1 Reduces Cell Adhesion and Induces Apoptosis in Prostate Cancer Cells" (2003) Cancer research 63(16): 5034-5040.
Mayr LM, et al. "Novel trends in high-throughput screening." (2009) Current opinion in pharmacology 9(5): 580-588.
Moffat JG, et al. "Phenotypic screening in cancer drug discovery—past, present and future." (2014) Nature reviews. Drug discovery 13(8): 588-602.
Mohan R, et al., "Withaferin A is a potent inhibitor of angiogenesis." (2004) Angiogenesis 7(2): 115-122.
Monks A, et al., "Genotoxic Profiling of MCF-7 Breast Cancer Cell Line Elucidates Gene Expression Modifications Underlying Toxicity of the Anticancer Drug 2-(4-Amino-3-methylphenyl)-5-fluorobenzothiazole" (2003) Molecular pharmacology 63(3): 766-772.
Nielsen TE, "Diversity-Oriented Syntheses Using the Build/Couple/Pair Strategy" (2008) Angewandte Chemie 47(1): 48-56.
Ogata M, et al., "Autophagy Is Activated for Cell Survival after Endoplasmic Reticulum Stress" (2006) Molecular and cellular biology 26(24): 9220-9231.
Pubchem-'656' Date Created: Oct. 26, 2006, Date Accessed: Jul. 18, 2016; p. 3, compound.
Sakaki K, Wu et al. "Protein Kinase Cθ Is Required for Autophagy in Response to Stress in the Endoplasmic Reticulum" (2008) The Journal of biological chemistry 283(22): 15370-15380.
Shim M, et al. "Protein Kinase C-dependent Regulation of NAG-1/Placental Bone Morphogenic Protein/MIC-1 Expression in LNCaP Prostate" (2005) The Journal of biological chemistry 280(19): 18636-18642.
Sundberg SA "High-throughput and ultra-high-throughput screening: solution- and cell-based approaches." (2000) Current opinion in biotechnology 11(1): 47-53.
Tan M, et al. "PTGF-β, a type β transforming growth factor (TGF-β) superfamily member, is a p53 target gene that inhibits tumor cell growth via TGF-β signaling pathway" (2000) Proceedings of the National Academy of Sciences of the United States of America 97(1): 109-114.
Tsuyuki S, et al., "Detection of WIPI1 mRNA as an indicator of autophagosome formation." (2014) Autophagy 10(3): 497-513.
Vanhara P, et al. (2012) "Growth/differentiation factor-15: prostate cancer suppressor or promoter?" Prostate cancer and prostatic diseases 15(4): 320-328.
Yan J, et al. "Usp9x- and Noxa-mediated Mcl-1 downregulation contributes to pemetrexed-induced apoptosis in human non-small-cell lung cancer cells" (2014) Cell death & disease 5: e1316.
Yang J, et al. "The Regulation of the Autophagic Network and Its Implications for Human Disease" (2013) International journal of biological sciences 9(10): 1121-1133.
Yap TA, Omlin A, de Bono JS "Development of therapeutic combinations targeting major cancer signaling pathways." (2013) Journal of clinical oncology : official journal of the American Society of Clinical Oncology 31(12): 1592-1605.
Zhang L, et al., "Small molecule regulators of autophagy identified by an image-based high-throughput screen" (2007) Proceedings of the National Academy of Sciences of the United States of America 104(48): 19023-19028.

* cited by examiner

A

B

US 10,457,662 B2

SUBSTITUTED AMIDES FOR TREATING AND PREVENTING CANCER

CROSS-REFERENCE TO RELATED APPLICATIONS

The present application is a national stage of International (PCT) Patent Application Serial No. PCT/US2016/033540, filed May 20, 2016, which claims priority to U.S. Provisional Patent Application No. 62/164,286, filed May 20, 2015, hereby incorporated by reference in their entireties.

FIELD OF THE INVENTION

This invention is in the field of medicinal chemistry. In particular, the invention relates to novel small molecule compounds having a quinolin-8-yl-nicotinamide structure which are useful in treating, ameliorating, or preventing various forms of cancer (e.g., pancreatic cancer).

INTRODUCTION

Cancer is the second most common cause of death in the United States, exceeded only by heart disease. In the United States, cancer accounts for 1 of every 4 deaths. The 5-year relative survival rate for all cancers patients diagnosed in 1996-2003 is 66%, up from 50% in 1975-1977 (see, e.g., Cancer Facts & Figures American Cancer Society: Atlanta, Ga. (2008)). This improvement in survival reflects progress in diagnosing at an earlier stage and improvements in treatment.

Discovering highly effective anticancer agents with low toxicity are needed.

SUMMARY OF THE INVENTION

Experiments conducted during the course of preparing embodiments for the present invention identified QN519

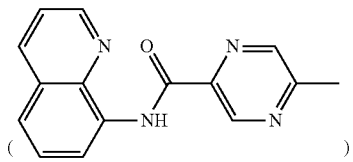 [SMILES: Cc1cnc(C(=O)Nc2cccc3cccnc23)cn1]

as a promising anticancer compound through a phenotypic screen of a library of 20,000 small-molecules representing five million compounds. QN519 represents a novel scaffold with drug-like properties and shows potent in vitro cytotoxicity in a panel of 12 cancer cell lines. Subsequent experiments involved performance of a lead optimization campaign to synthesize a series of novel analogs. Fifty novel analogs were tested in three pancreatic cancer cell lines using MTT assay. Sixteen compounds produced IC50 values <1 µM in at least one cell line. One of the optimized compounds, QN523

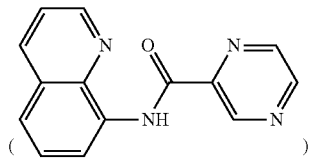 [SMILES: O=C(Nc1cccc2cccnc12)c1cnccn1]

showed significant in vivo efficacy in a pancreatic cancer xenograft model. No symptoms of gross toxicity such as weakness, weight loss or lethargy were observed in the QN523 treatment group. H&E stained organ sections of liver, kidney, heart, lung, spleen and pancreas did not reveal significant histopathological changes, further confirming the safety of the treatment. QN523 treatment was shown to significantly increase the expression of GDF15, ATF3, DDIT3 and HSPA5 genes, indicating activation of the stress response pathway. A significant decrease in the expression of WIPI1, GABARAPL1 and MAP1LC3B was also observed implicating autophagy as a major mechanism of action. Because of the lack of effective treatments for pancreatic cancer, discovery of novel agents such as the compounds disclosed herein with a unique mechanism of action, will fulfill this unmet medical need. As such, the invention relates to novel small molecule compounds having a quinolin-8-yl-nicotinamide structure which are useful in treating, ameliorating, or preventing various forms of cancer (e.g., pancreatic cancer).

Accordingly, the present invention contemplates that exposure of animals (e.g., humans) suffering from cancer (e.g., pancreatic cancer) (e.g., and/or cancer related disorders) to therapeutically effective amounts of drug(s) having a quinolin-8-yl-nicotinamide structure (e.g., small molecules having a quinolin-8-yl-nicotinamide structure as disclosed herein) will inhibit the growth of cancer cells or supporting cells outright and/or render such cells as a population more susceptible to the cell death-inducing activity of cancer therapeutic drugs or radiation therapies (e.g., through inhibition of gene expression associated with the stress response pathway) (e.g., through activation of gene expression associated with autophagy).

The present invention contemplates that the small molecule compounds as disclosed herein (e.g., having a quinolin-8-yl-nicotinamide structure) satisfy an unmet need for the treatment of multiple cancer types, either when administered as monotherapy to induce cell growth inhibition, apoptosis and/or cell cycle arrest in cancer cells, or when administered in a temporal relationship with additional agent(s), such as other cell death-inducing or cell cycle disrupting cancer therapeutic drugs or radiation therapies (combination therapies), so as to render a greater proportion of the cancer cells or supportive cells susceptible to executing the apoptosis program compared to the corresponding proportion of cells in an animal treated only with the cancer therapeutic drug or radiation therapy alone.

In certain embodiments of the invention, combination treatment of animals with a therapeutically effective amount of a compound of the present invention and a course of an anticancer agent produces a greater tumor response and clinical benefit in such animals compared to those treated with the compound or anticancer drugs/radiation alone. Since the doses for all approved anticancer drugs and radiation treatments are known, the present invention contemplates the various combinations of them with the present compounds.

The Applicants have found that certain small molecule compounds having a quinolin-8-yl-nicotinamide structure serve as therapeutics for the treatment of cancer and other diseases. Thus, the present invention relates to quinolin-8-yl-nicotinamide compounds useful for inhibiting cancer cell growth (e.g., pancreatic cancer cell growth) (e.g., through inhibition of gene expression associated with the stress response pathway) (e.g., through activation of gene expression associated with autophagy) (e.g., thereby facilitating cell apoptosis), and increasing the sensitivity of cells to inducers of apoptosis and/or cell cycle arrest. Certain quinolin-8-yl-nicotinamide compounds of the present invention may exist as stereoisomers including optical isomers. The invention includes all stereoisomers, both as pure individual stereoisomer preparations and enriched preparations of each, and both the racemic mixtures of such stereoisomers as well as the individual diastereomers and enantiomers that may be separated according to methods that are well known to those of skill in the art.

In a particular embodiment, compounds encompassed within Formula I are provided:

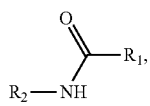

including pharmaceutically acceptable salts, solvates, and/or prodrugs thereof. Formula I is not limited to a particular chemical moiety for R1 and R2.

In some embodiments, the particular chemical moiety for R1 and R2 independently include any chemical moiety that permits the resulting compound to inhibit cancer cell growth (e.g., pancreatic cell growth).

In some embodiments, the particular chemical moiety for R1 and R2 independently include any chemical moiety that permits the resulting compound to activate gene expression within the stress response pathway within cancer cells. For example, in some embodiments, the particular chemical moiety for R1 and R2 independently include any chemical moiety that permits the resulting compound to activate expression of one or more of the following genes within the stress response pathway within cancer cells: GDF15, ATF3, DDIT3 and HSPA5.

In some embodiments, the particular chemical moiety for R1 and R2 independently include any chemical moiety that permits the resulting compound to inhibit gene expression known to inhibit autophagy within cancer cells. For example, in some embodiments, the particular chemical moiety for R1 and R2 independently include any chemical moiety that permits the resulting compound to inhibit gene expression of one or more of the following genes known to inhibit autophagy within cancer cells: WIPI1, GABARAPL1, and MAP1LC3B.

In some embodiments, R1 is selected from the group consisting of hydrogen,

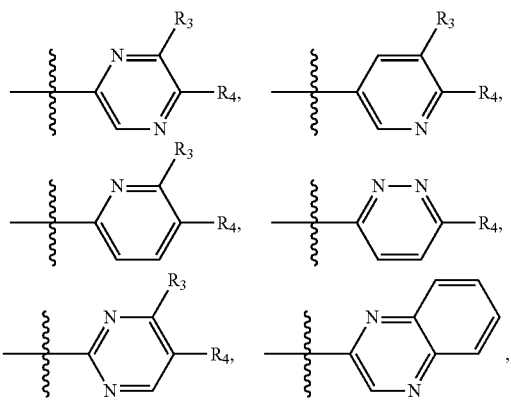

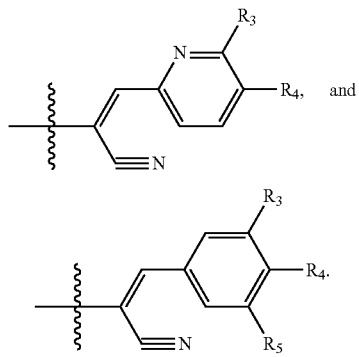

In some embodiments, R3, R4 and R5 are independently selected from hydrogen, halogen (e.g., Chlorine, Bromine, Fluorine, etc.), methoxy (e.g., —OCH3), alkyl (e.g., methyl, ethyl, etc.), and hydroxy (e.g., OH).

In some embodiments, R2 is selected from hydrogen,

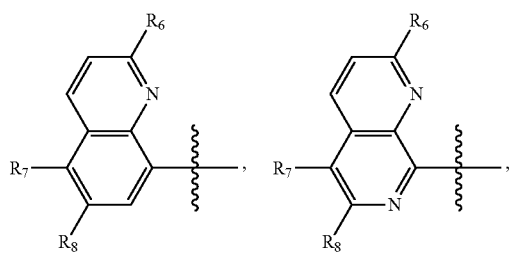

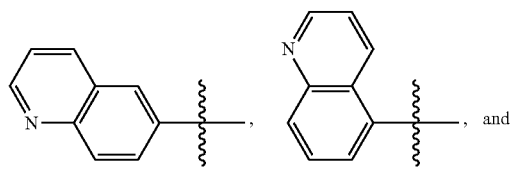

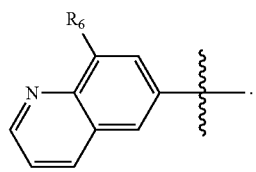

In some embodiments, R6, R7 and R8 are independently selected from hydrogen, halogen (e.g., Chlorine, Bromine, Fluorine, etc.), alkyl (e.g., methyl, ethyl),

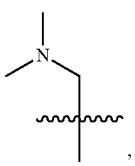

hydroxyl (e.g., —OH), methoxy (e.g., —OCH3),
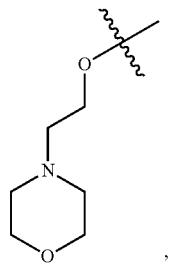 [SMILES: *OCCN1CCOCC1]
amino (e.g., —NH2),
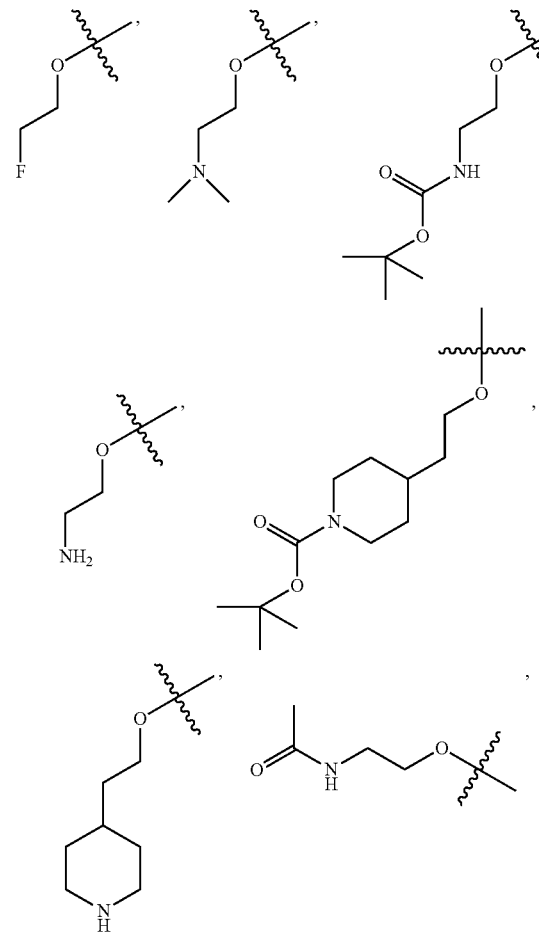
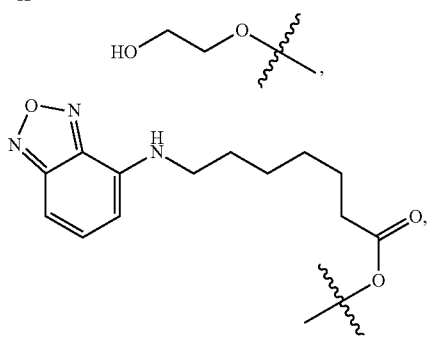
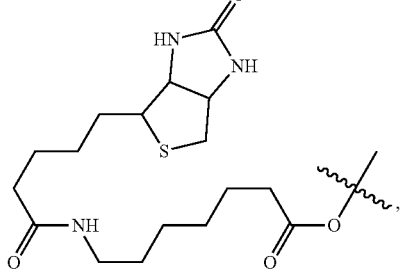
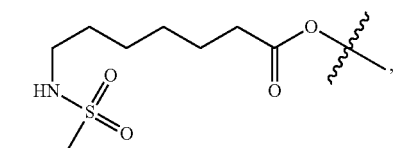
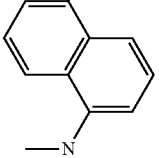
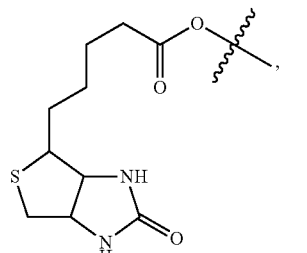
Table 1 (see, Examples) show IC$_{50}$ values of compounds encompassed within Formula I in pancreatic cell lines.
In some embodiments, the following compounds are contemplated for Formula I:
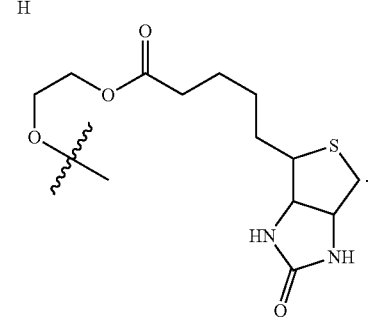
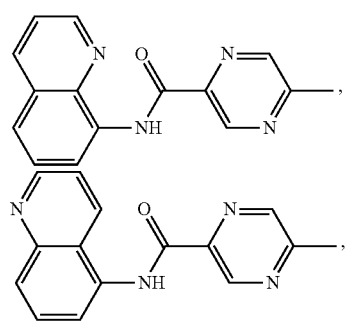

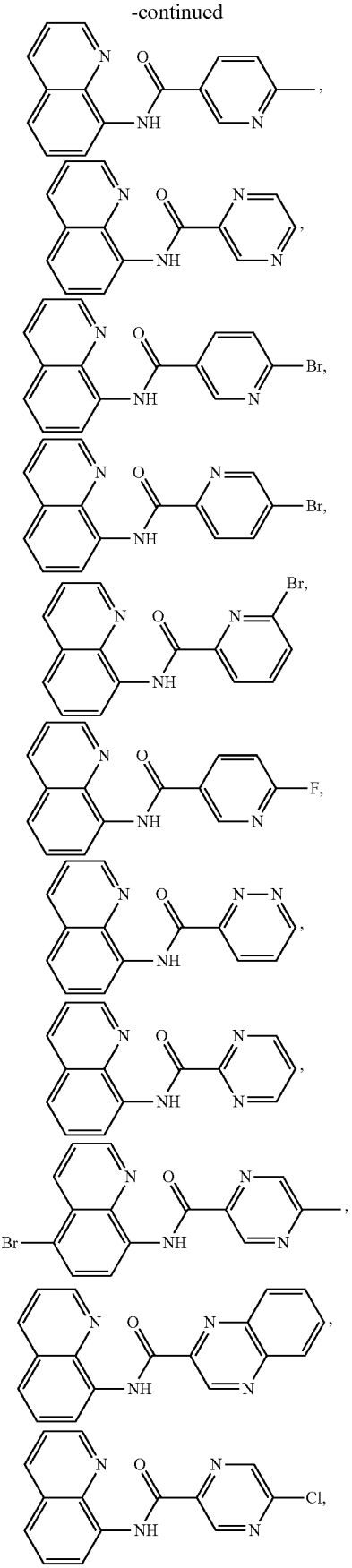
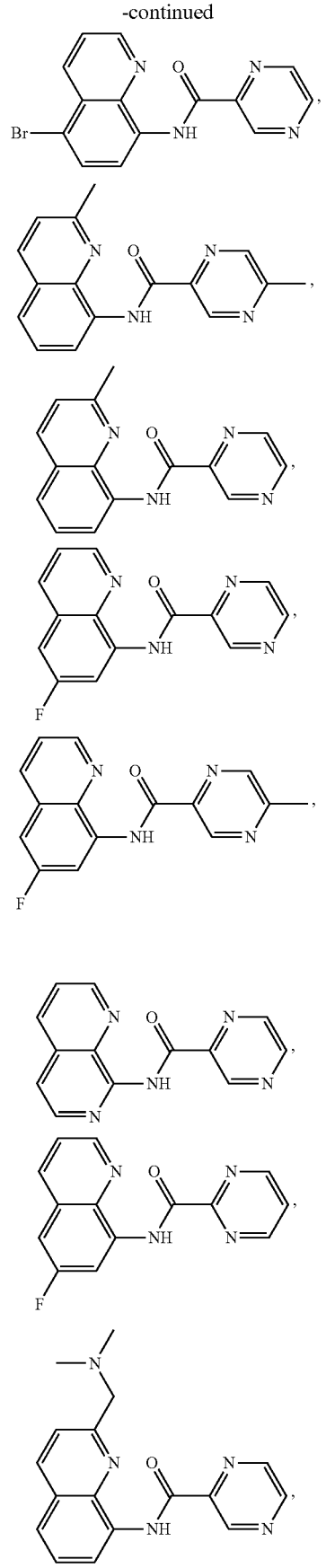

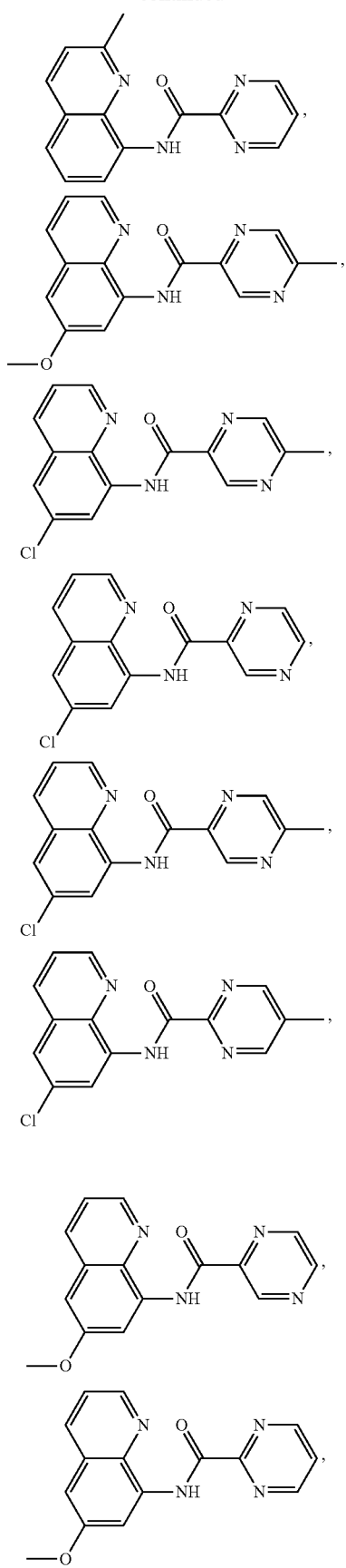
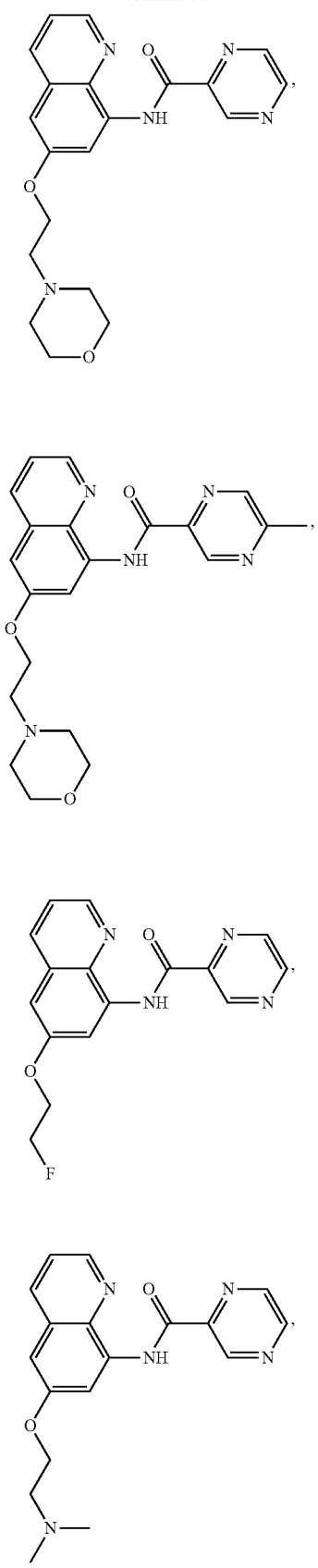

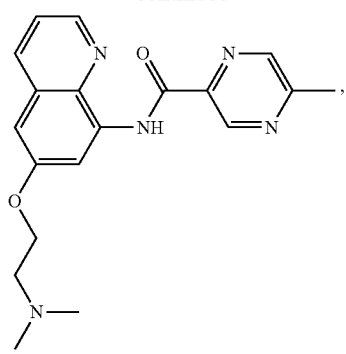
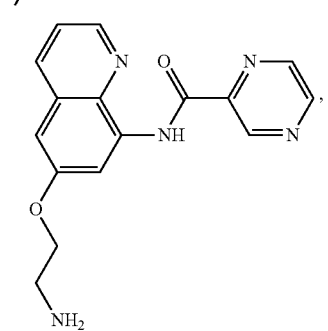
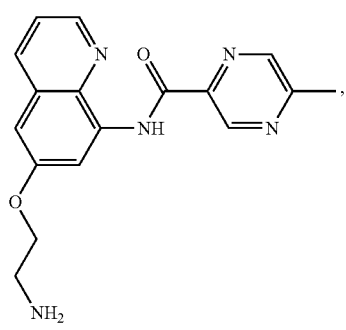
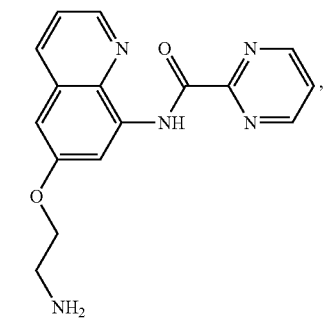
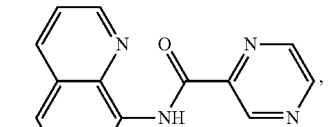
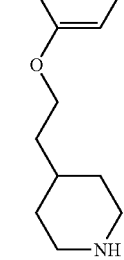
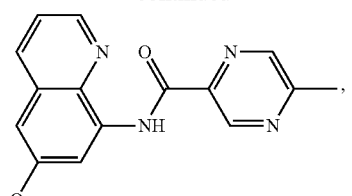
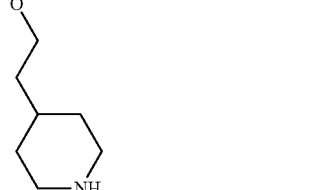
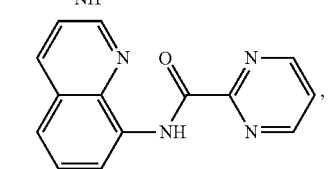
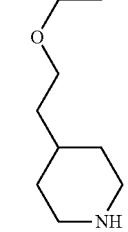
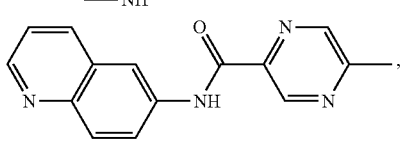
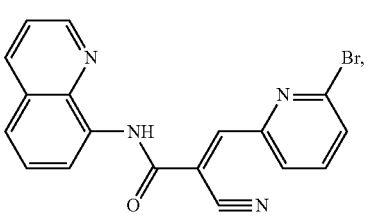
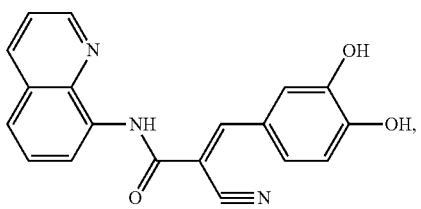
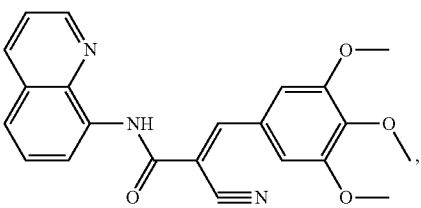

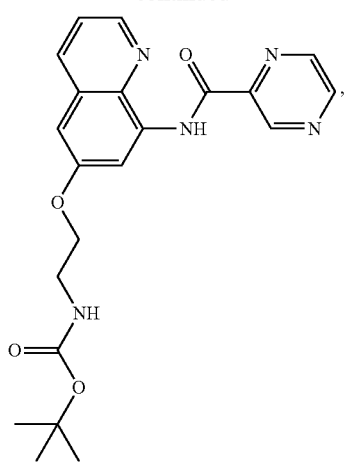
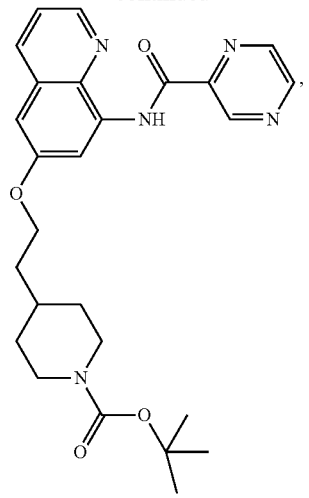
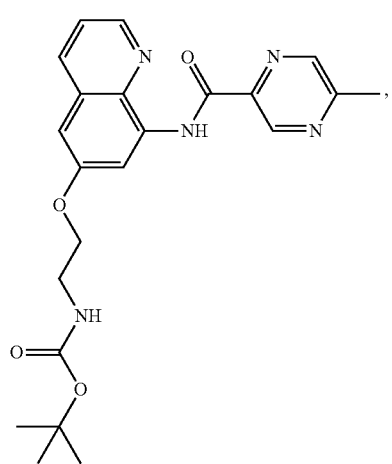
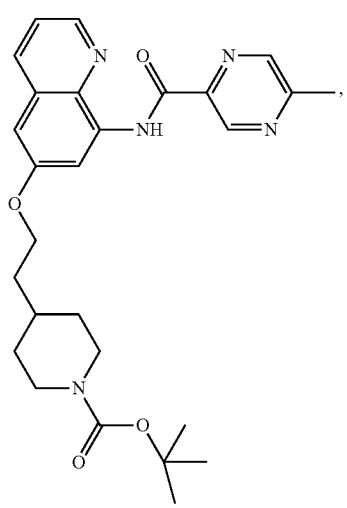
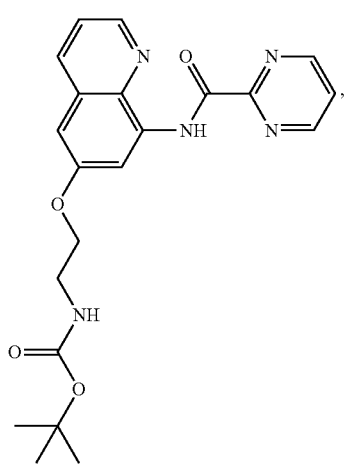
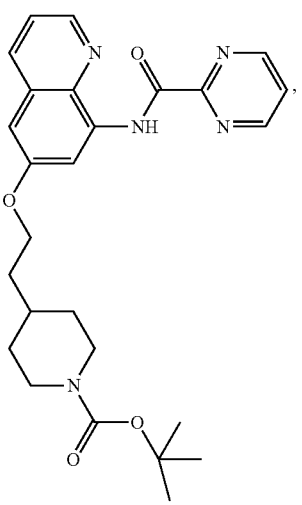

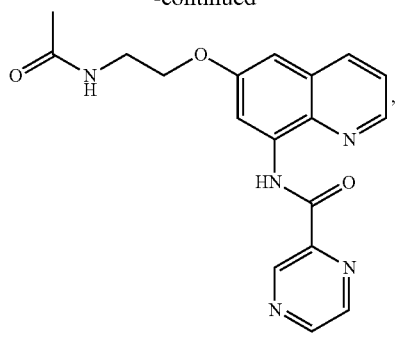
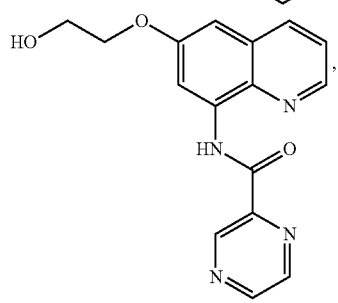
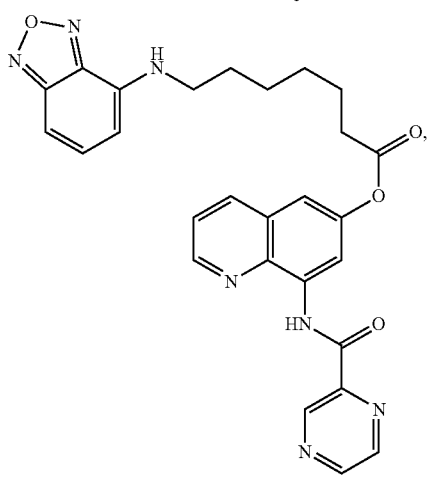
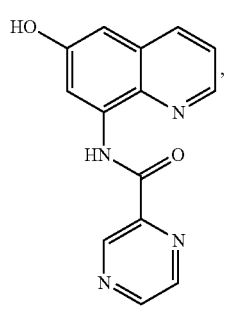
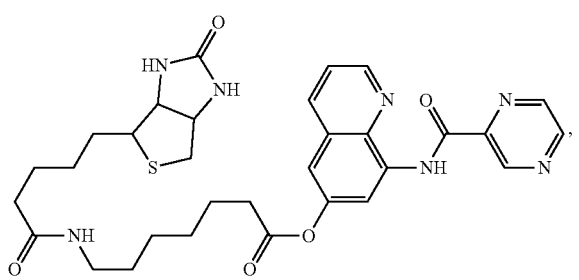
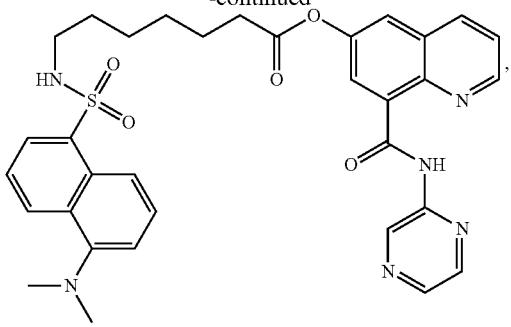
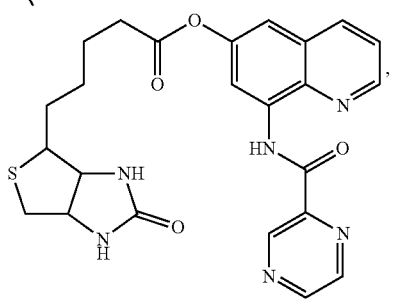
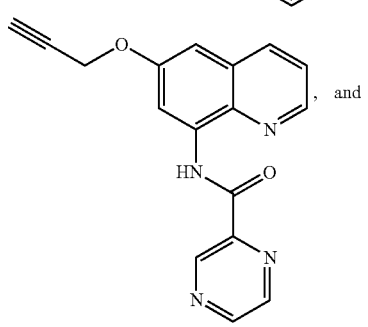
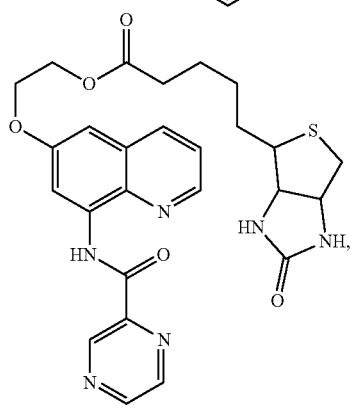
or a pharmaceutically acceptable salt, solvate, or prodrug thereof.
In some embodiments, the present invention provides the following compound:
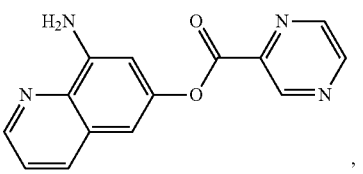 [SMILES: Nc1cc(OC(=O)c2cnccn2)cc2cccnc12]

or a pharmaceutically acceptable salt, solvate, or prodrug thereof.

The invention further provides processes for preparing any of the compounds of the present invention through following at least a portion of the techniques recited the Examples.

The invention also provides the use of compounds to induce cell cycle arrest and/or apoptosis in cancer cells (e.g., pancreatic cancer cells). The invention also relates to the use of compounds for sensitizing cells to additional agent(s), such as inducers of apoptosis and/or cell cycle arrest, and chemoprotection of normal cells through the induction of cell cycle arrest prior to treatment with chemotherapeutic agents.

The compounds of the invention are useful for the treatment, amelioration, or prevention of disorders, such as those responsive to induction of apoptotic cell death, e.g., disorders characterized by dysregulation of apoptosis, including hyperproliferative diseases such as cancer. In certain embodiments, the compounds can be used to treat, ameliorate, or prevent cancer that is characterized by resistance to cancer therapies (e.g., those cancer cells which are chemoresistant, radiation resistant, hormone resistant, and the like). In certain embodiments, the cancer is pancreatic cancer.

The invention also provides pharmaceutical compositions comprising the compounds of the invention in a pharmaceutically acceptable carrier.

The invention also provides kits comprising a compound of the invention and instructions for administering the compound to an animal. The kits may optionally contain other therapeutic agents, e.g., anticancer agents or apoptosis-modulating agents.

DEFINITIONS

Figure 1:
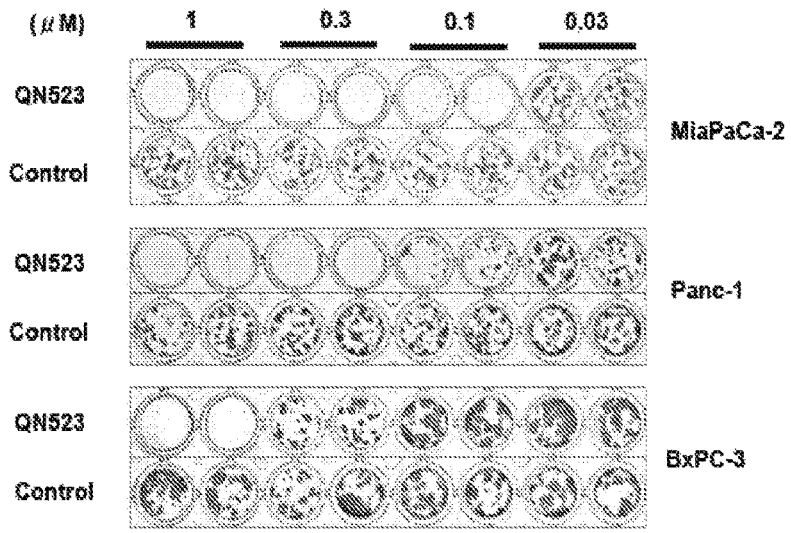
FIG. 1A-B: QN523 is cytotoxic in pancreatic cancer cell lines. A) QN523 inhibits colony formation in PDAC cell lines. Cells were treated with QN523 for 24 h and left in culture in fresh media until colonies were observed in control wells. B) QN523 inhibits cell proliferation time dependently in MiaPaCa-2 cells. Cells were treated with QN523 for 1, 4, 8, 24, 48, 72 h and left in culture in fresh media. MTT assay was performed 72 h after initiation of treatment. Data points represent Mean±SD from three independent experiments.

The term "anticancer agent" as used herein, refer to any therapeutic agents (e.g., chemotherapeutic compounds and/or molecular therapeutic compounds), antisense therapies, radiation therapies, or surgical interventions, used in the treatment of hyperproliferative diseases such as cancer (e.g., in mammals, e.g., in humans).

The term "prodrug" as used herein, refers to a pharmacologically inactive derivative of a parent "drug" molecule that requires biotransformation (e.g., either spontaneous or enzymatic) within the target physiological system to release, or to convert (e.g., enzymatically, physiologically, mechanically, electromagnetically) the prodrug into the active drug. Prodrugs are designed to overcome problems associated with stability, water solubility, toxicity, lack of specificity, or limited bioavailability. Exemplary prodrugs comprise an active drug molecule itself and a chemical masking group (e.g., a group that reversibly suppresses the activity of the drug). Some prodrugs are variations or derivatives of compounds that have groups cleavable under metabolic conditions. Prodrugs can be readily prepared from the parent compounds using methods known in the art, such as those described in A Textbook of Drug Design and Development, Krogsgaard-Larsen and H. Bundgaard (eds.), Gordon & Breach, 1991, particularly Chapter 5: "Design and Applications of Prodrugs"; Design of Prodrugs, H. Bundgaard (ed.), Elsevier, 1985; Prodrugs: Topical and Ocular Drug Delivery, K. B. Sloan (ed.), Marcel Dekker, 1998; Methods in Enzymology, K. Widder et al. (eds.), Vol. 42, Academic Press, 1985, particularly pp. 309-396; Burger's Medicinal Chemistry and Drug Discovery, 5th Ed., M. Wolff (ed.), John Wiley & Sons, 1995, particularly Vol. 1 and pp. 172-178 and pp. 949-982; Pro-Drugs as Novel Delivery Systems, T. Higuchi and V. Stella (eds.), Am. Chem. Soc., 1975; and Bioreversible Carriers in Drug Design, E. B. Roche (ed.), Elsevier, 1987.

Exemplary prodrugs become pharmaceutically active in vivo or in vitro when they undergo solvolysis under physiological conditions or undergo enzymatic degradation or other biochemical transformation (e.g., phosphorylation, hydrogenation, dehydrogenation, glycosylation). Prodrugs often offer advantages of water solubility, tissue compatibility, or delayed release in the mammalian organism. (See e.g., Bundgard, Design of Prodrugs, pp. 7-9, 21-24, Elsevier, Amsterdam (1985); and Silverman, The Organic Chemistry of Drug Design and Drug Action, pp. 352-401, Academic Press, San Diego, Calif. (1992)). Common prodrugs include acid derivatives such as esters prepared by reaction of parent acids with a suitable alcohol (e.g., a lower alkanol) or esters prepared by reaction of parent alcohol with a suitable carboxylic acid, (e.g., an amino acid), amides prepared by reaction of the parent acid compound with an amine, basic groups reacted to form an acylated base derivative (e.g., a lower alkylamide), or phosphorus-containing derivatives, e.g., phosphate, phosphonate, and phosphoramidate esters, including cyclic phosphate, phosphonate, and phosphoramidate (see, e.g., US Patent Application Publication No. US 2007/0249564 A1; herein incorporated by reference in its entirety).

The term "pharmaceutically acceptable salt" as used herein, refers to any salt (e.g., obtained by reaction with an acid or a base) of a compound of the present invention that is physiologically tolerated in the target animal (e.g., a mammal). Salts of the compounds of the present invention may be derived from inorganic or organic acids and bases. Examples of acids include, but are not limited to, hydrochloric, hydrobromic, sulfuric, nitric, perchloric, fumaric, maleic, phosphoric, glycolic, lactic, salicylic, succinic, toluene-p-sulfonic, tartaric, acetic, citric, methanesulfonic, ethanesulfonic, formic, benzoic, malonic, sulfonic, naphthalene-2-sulfonic, benzenesulfonic acid, and the like. Other acids, such as oxalic, while not in themselves pharmaceutically acceptable, may be employed in the preparation of salts useful as intermediates in obtaining the compounds of the invention and their pharmaceutically acceptable acid addition salts.

Examples of bases include, but are not limited to, alkali metal (e.g., sodium) hydroxides, alkaline earth metal (e.g., magnesium) hydroxides, ammonia, and compounds of formula $NW_4^+$, wherein W is $C_{1-4}$ alkyl, and the like.

Examples of salts include, but are not limited to: acetate, adipate, alginate, aspartate, benzoate, benzenesulfonate, bisulfate, butyrate, citrate, camphorate, camphorsulfonate, cyclopentanepropionate, digluconate, dodecylsulfate, ethanesulfonate, fumarate, flucoheptanoate, glycerophosphate, hemisulfate, heptanoate, hexanoate, chloride, bromide, iodide, 2-hydroxyethanesulfonate, lactate, maleate, mesylate, methanesulfonate, 2-naphthalenesulfonate, nicotinate, oxalate, palmoate, pectinate, persulfate, phenylpropionate, picrate, pivalate, propionate, succinate, tartrate, thiocyanate, tosylate, undecanoate, and the like. Other examples of salts include anions of the compounds of the present invention compounded with a suitable cation such as $Na^+$, $NH_4^+$, and $NW_4^+$ (wherein W is a $C_{1-4}$ alkyl group), and the like. For therapeutic use, salts of the compounds of the present invention are contemplated as being pharmaceutically acceptable. However, salts of acids and bases that are non-pharmaceutically acceptable may also find use, for example, in the preparation or purification of a pharmaceutically acceptable compound.

The term "solvate" as used herein, refers to the physical association of a compound of the invention with one or more solvent molecules, whether organic or inorganic. This physical association often includes hydrogen bonding. In certain instances, the solvate is capable of isolation, for example, when one or more solvate molecules are incorporated in the crystal lattice of the crystalline solid. "Solvate" encompasses both solution-phase and isolable solvates. Exemplary solvates include hydrates, ethanolates, and methanolates.

The term "therapeutically effective amount," as used herein, refers to that amount of the therapeutic agent sufficient to result in amelioration of one or more symptoms of a disorder, or prevent advancement of a disorder, or cause regression of the disorder. For example, with respect to the treatment of cancer, in one embodiment, a therapeutically effective amount will refer to the amount of a therapeutic agent that decreases the rate of tumor growth, decreases tumor mass, decreases the number of metastases, increases time to tumor progression, or increases survival time by at least 5%, at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95%, or at least 100%.

The terms "sensitize" and "sensitizing," as used herein, refer to making, through the administration of a first agent (e.g., a benzoic acid compound of the invention), an animal or a cell within an animal more susceptible, or more responsive, to the biological effects (e.g., promotion or retardation of an aspect of cellular function including, but not limited to, cell division, cell growth, proliferation, invasion, angiogenesis, necrosis, or apoptosis) of a second agent. The sensitizing effect of a first agent on a target cell can be measured as the difference in the intended biological effect (e.g., promotion or retardation of an aspect of cellular function including, but not limited to, cell growth, proliferation, invasion, angiogenesis, or apoptosis) observed upon the administration of a second agent with and without administration of the first agent. The response of the sensitized cell can be increased by at least about 10%, at least about 20%, at least about 30%, at least about 40%, at least about 50%, at least about 60%, at least about 70%, at least about 80%, at least about 90%, at least about 100%, at least about 150%, at least about 200%, at least about 250%, at least about 300%, at least about 350%, at least about 400%, at least about 450%, or at least about 500% over the response in the absence of the first agent.

The term "dysregulation of apoptosis," as used herein, refers to any aberration in the ability of (e.g., predisposition) a cell to undergo cell death via apoptosis. Dysregulation of apoptosis is associated with or induced by a variety of conditions, non-limiting examples of which include, autoimmune disorders (e.g., systemic lupus erythematosus, rheumatoid arthritis, graft-versus-host disease, myasthenia gravis, or Sjögren's syndrome), chronic inflammatory conditions (e.g., psoriasis, asthma or Crohn's disease), hyperproliferative disorders (e.g., tumors, B cell lymphomas, or T cell lymphomas), viral infections (e.g., herpes, papilloma, or HIV), and other conditions such as osteoarthritis and atherosclerosis.

The term "hyperproliferative disease," as used herein, refers to any condition in which a localized population of proliferating cells in an animal is not governed by the usual limitations of normal growth. Examples of hyperproliferative disorders include tumors, neoplasms, lymphomas and the like. A neoplasm is said to be benign if it does not undergo invasion or metastasis and malignant if it does either of these. A "metastatic" cell means that the cell can invade and destroy neighboring body structures. Hyperplasia is a form of cell proliferation involving an increase in cell number in a tissue or organ without significant alteration in structure or function. Metaplasia is a form of controlled cell growth in which one type of fully differentiated cell substitutes for another type of differentiated cell.

The term "neoplastic disease," as used herein, refers to any abnormal growth of cells being either benign (non-cancerous) or malignant (cancerous).

The term "normal cell," as used herein, refers to a cell that is not undergoing abnormal growth or division. Normal cells are non-cancerous and are not part of any hyperproliferative disease or disorder.

The term "anti-neoplastic agent," as used herein, refers to any compound that retards the proliferation, growth, or spread of a targeted (e.g., malignant) neoplasm.

The terms "prevent," "preventing," and "prevention," as used herein, refer to a decrease in the occurrence of pathological cells (e.g., hyperproliferative or neoplastic cells) in an animal. The prevention may be complete, e.g., the total absence of pathological cells in a subject. The prevention may also be partial, such that the occurrence of pathological cells in a subject is less than that which would have occurred without the present invention.

The term "pharmaceutically acceptable carrier" or "pharmaceutically acceptable vehicle" encompasses any of the standard pharmaceutical carriers, solvents, surfactants, or vehicles. Suitable pharmaceutically acceptable vehicles include aqueous vehicles and nonaqueous vehicles. Standard pharmaceutical carriers and their formulations are described in Remington's Pharmaceutical Sciences, Mack Publishing Co., Easton, Pa., 19th ed. 1995.

DETAILED DESCRIPTION OF THE INVENTION

Numerous high throughput-screening platforms are routinely being used in drug discovery programs to identify lead compounds (see, e.g., Sundberg S A (2000) Current opinion in biotechnology 11(1): 47-53; Mayr L M, Bojanic D (2009) Current opinion in pharmacology 9(5): 580-588). Expanding collections of synthetic small molecules prepared by new organic chemistry strategies (see, e.g., Nielsen T E, Schreiber S L (2008) Angewandte Chemie 47(1): 48-56; C J O C, et al., (2012) Chemical Society reviews 41(12): 4444-4456) are fueling such screening systems. Advances in target-based screening approaches are especially prominent and has enabled rapid discovery of potent and selective molecules against single targets. Discovery of cancer drug candidates has largely adopted this approach and generated a variety of targeted therapeutics that entered clinical trials. However, only 5% of such investigational agents are marketed after demonstrating efficacy in phase III clinical trials (see, e.g., Hutchinson L, Kirk R (2011) Nature reviews. Clinical oncology 8(4): 189-190). As a complex disease, cancer cells display low therapeutic susceptibility to targeted treatment by hijacking multiple signaling networks with functional redundancies to fulfill its deleterious features. The high cellular heterogeneity adds to the complexity of the disease, leading to high drug attrition rates in oncology. As a result, the therapeutic demand for cancer treatment is highly unmet, and calls for discovery of drugs with novel mechanisms. To address such challenges in cancer drug discovery, phenotypic screen with representative models resurging as a promising strategy (see, e.g., Moffat J G, Rudolph J, Bailey D (2014) Nature reviews. Drug discovery 13(8): 588-602). Without predetermined therapeutic assumptions on certain targets, this approach uses selected phenotype as experimental readout, giving rise to discovery of new drug candidates with novel targets and unique mechanisms of action in the disease-relevant context. In addition, when combined with pathway profiling or genomic analysis, phenotypic assays can guide rational drug combination, which represents the current standard of care for cancer (see, e.g., Al-Lazikani B, Banerji U, Workman P (2012) Nature biotechnology 30(7): 679-692; Yap T A, Omlin A, de Bono J S (2013) Journal of clinical oncology: official journal of the American Society of Clinical Oncology 31(12): 1592-1605; Dawson J C, Carragher N O (2014) Frontiers in pharmacology 5: 118). Taken together, phenotypic screen demonstrates great potential as the starting point for cancer drug discovery.

Experiments conducted during the course of preparing embodiments for the present invention identified QN519

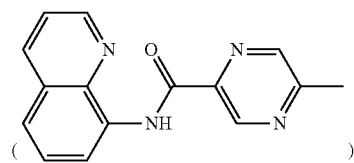

as a promising anticancer compound through a phenotypic screen of a library of 20,000 small-molecules representing five million compounds. QN519 represents a novel scaffold with drug-like properties and shows potent in vitro cytotoxicity in a panel of 12 cancer cell lines. Subsequent experiments involved performance of a lead optimization campaign to synthesize a series of novel analogs. Fifty novel analogs were tested in three pancreatic cancer cell lines using MTT assay. Sixteen compounds produced IC50 values <1 μM in at least one cell line. One of the optimized compounds, QN523

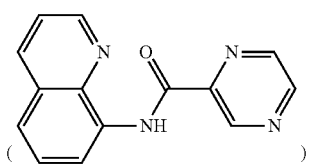 [SMILES: O=C(Nc1cccc2cccnc12)c1cnccn1]

showed significant in vivo efficacy in a pancreatic cancer xenograft model. No symptoms of gross toxicity such as weakness, weight loss or lethargy were observed in the QN523 treatment group. H&E stained organ sections of liver, kidney, heart, lung, spleen and pancreas did not reveal significant histopathological changes, further confirming the safety of the treatment. QN523 treatment was shown to significantly increase the expression of GDF15, ATF3, DDIT3 and HSPA5 genes, indicating activation of the stress response pathway. A significant decrease in the expression of WIPI1, GABARAPL1 and MAP1LC3B was also observed implicating autophagy as a major mechanism of action. Because of the lack of effective treatments for pancreatic cancer, discovery of novel agents such as the compounds disclosed herein with a unique mechanism of action, will fulfill this unmet medical need. As such, the invention relates to novel small molecule compounds having a quinolin-8-yl-nicotinamide structure which are useful in treating, ameliorating, or preventing various forms of cancer (e.g., pancreatic cancer).

Accordingly, the present invention contemplates that exposure of animals (e.g., humans) suffering from cancer (e.g., pancreatic cancer) (e.g., and/or cancer related disorders) to therapeutically effective amounts of drug(s) having a quinolin-8-yl-nicotinamide structure (e.g., small molecules having a quinolin-8-yl-nicotinamide structure as disclosed herein) will inhibit the growth of cancer cells or supporting cells outright and/or render such cells as a population more susceptible to the cell death-inducing activity of cancer therapeutic drugs or radiation therapies (e.g., through inhibition of gene expression associated with the stress response pathway) (e.g., through activation of gene expression associated with autophagy).

The present invention contemplates that the small molecule compounds as disclosed herein (e.g., having a quinolin-8-yl-nicotinamide structure) satisfy an unmet need for the treatment of multiple cancer types, either when administered as monotherapy to induce cell growth inhibition, apoptosis and/or cell cycle arrest in cancer cells, or when administered in a temporal relationship with additional agent(s), such as other cell death-inducing or cell cycle disrupting cancer therapeutic drugs or radiation therapies (combination therapies), so as to render a greater proportion of the cancer cells or supportive cells susceptible to executing the apoptosis program compared to the corresponding proportion of cells in an animal treated only with the cancer therapeutic drug or radiation therapy alone.

In certain embodiments of the invention, combination treatment of animals with a therapeutically effective amount of a compound of the present invention and a course of an anticancer agent produces a greater tumor response and clinical benefit in such animals compared to those treated with the compound or anticancer drugs/radiation alone. Since the doses for all approved anticancer drugs and radiation treatments are known, the present invention contemplates the various combinations of them with the present compounds.

The Applicants have found that certain small molecule compounds having a quinolin-8-yl-nicotinamide structure serve as therapeutics for the treatment of cancer and other diseases. Thus, the present invention relates to quinolin-8-yl-nicotinamide compounds useful for inhibiting cancer cell growth (e.g., pancreatic cancer cell growth) (e.g., through inhibition of gene expression associated with the stress response pathway) (e.g., through activation of gene expression associated with autophagy) (e.g., thereby facilitating cell apoptosis), and increasing the sensitivity of cells to inducers of apoptosis and/or cell cycle arrest. Certain quinolin-8-yl-nicotinamide compounds of the present invention may exist as stereoisomers including optical isomers. The invention includes all stereoisomers, both as pure individual stereoisomer preparations and enriched preparations of each, and both the racemic mixtures of such stereoisomers as well as the individual diastereomers and enantiomers that may be separated according to methods that are well known to those of skill in the art.

In a particular embodiment, compounds encompassed within Formula I are provided:

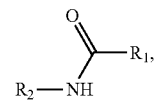

including pharmaceutically acceptable salts, solvates, and/or prodrugs thereof. Formula I is not limited to a particular chemical moiety for R1 and R2.

In some embodiments, the particular chemical moiety for R1 and R2 independently include any chemical moiety that permits the resulting compound to inhibit cancer cell growth (e.g., pancreatic cell growth).

In some embodiments, the particular chemical moiety for R1 and R2 independently include any chemical moiety that permits the resulting compound to activate gene expression within the stress response pathway within cancer cells. For example, in some embodiments, the particular chemical moiety for R1 and R2 independently include any chemical moiety that permits the resulting compound to activate expression of one or more of the following genes within the stress response pathway within cancer cells: GDF15, ATF3, DDIT3 and HSPA5.

In some embodiments, the particular chemical moiety for R1 and R2 independently include any chemical moiety that permits the resulting compound to inhibit gene expression known to inhibit autophagy within cancer cells. For example, in some embodiments, the particular chemical moiety for R1 and R2 independently include any chemical moiety that permits the resulting compound to inhibit gene expression of one or more of the following genes known to inhibit autophagy within cancer cells: WIPI1, GABARAPL1, and MAP1LC3B.

In some embodiments, R1 is selected from the group consisting of hydrogen,

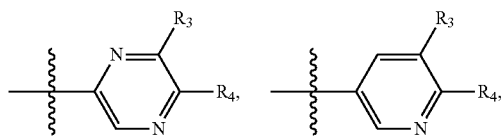

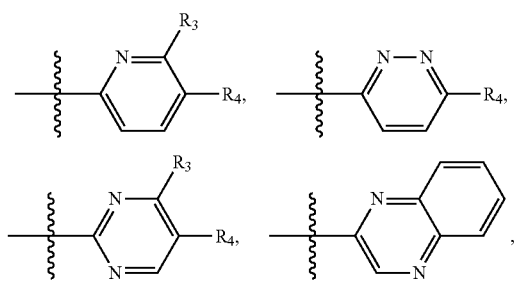
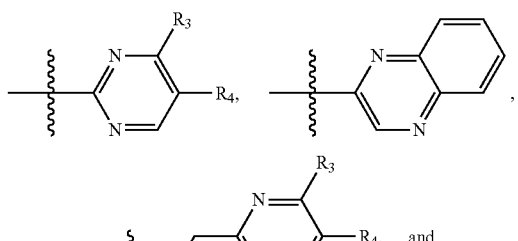
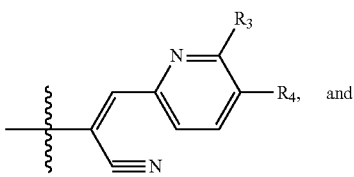
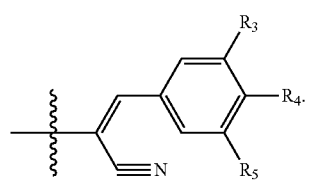

In some embodiments, R3, R4 and R5 are independently selected from hydrogen, halogen (e.g., Chlorine, Bromine, Fluorine, etc.), methoxy (e.g., —OCH3), alkyl (e.g., methyl, ethyl, etc.), and hydroxy (e.g., OH).

In some embodiments, R2 is selected from hydrogen,

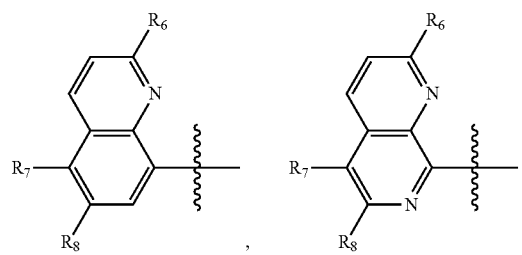
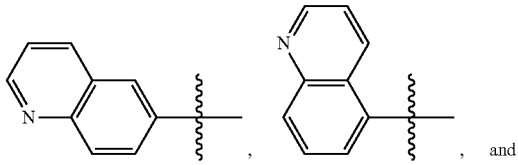
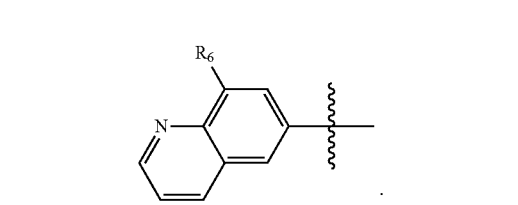

In some embodiments, R6, R7 and R8 are independently selected from hydrogen, halogen (e.g., Chlorine, Bromine, Fluorine, etc.), alkyl (e.g., methyl, ethyl),

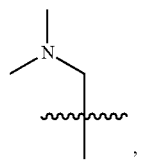

methoxy (e.g., —OCH3),

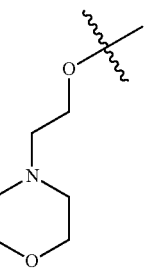

amino (e.g., —NH2),

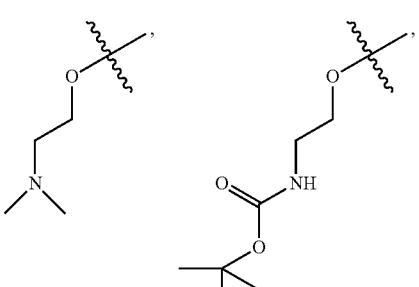
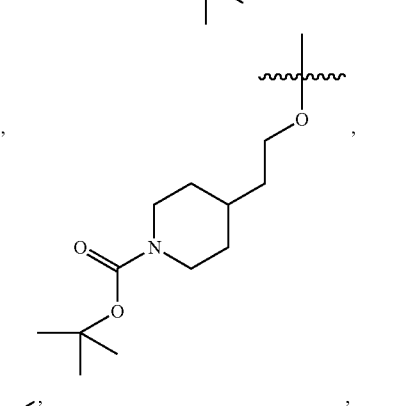
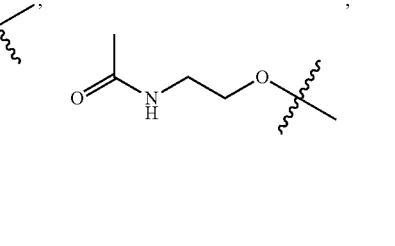

-continued
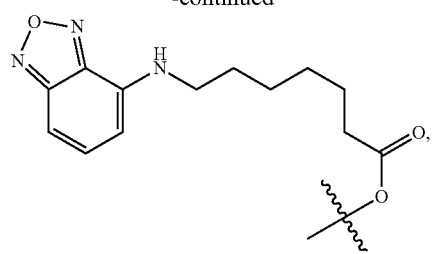
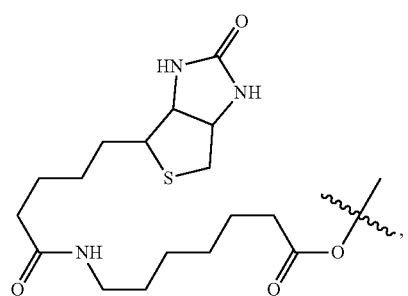
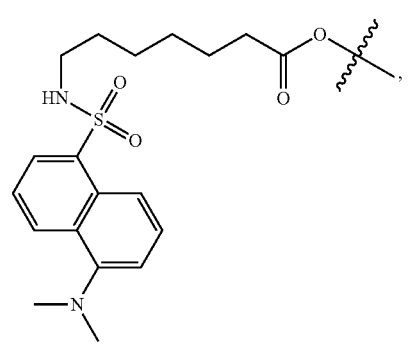
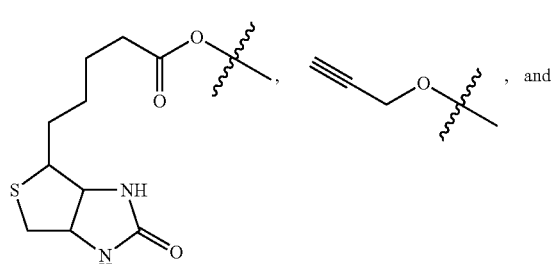
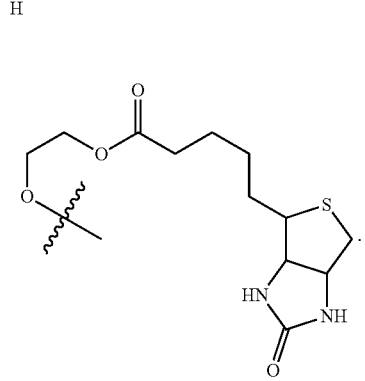
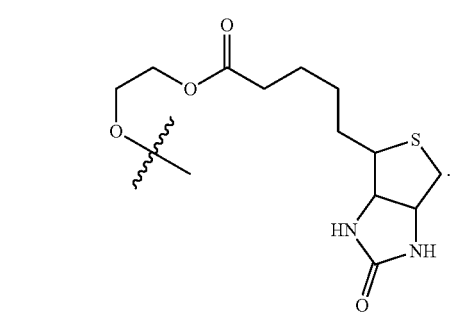
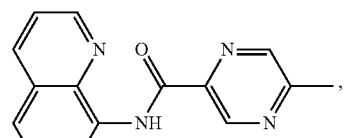
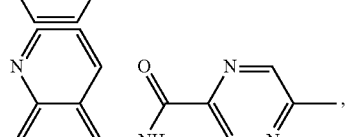
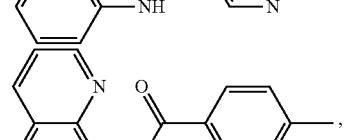
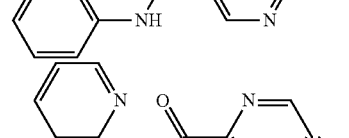
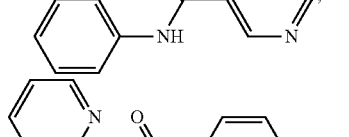
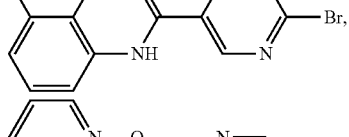
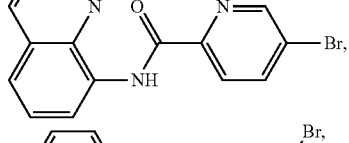
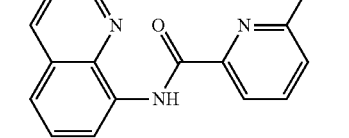
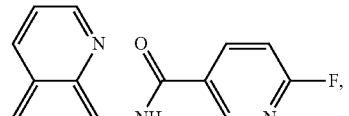
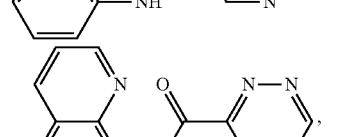
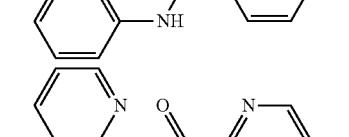
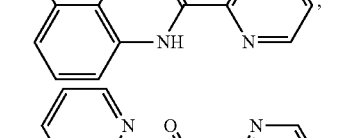
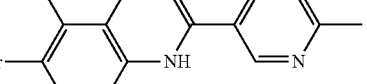
Table 1 (see, Example I) show IC$_{50}$ values of compounds encompassed within Formula I in pancreatic cell lines.
In some embodiments, the following compounds are contemplated for Formula I:

-continued
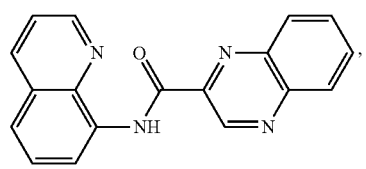
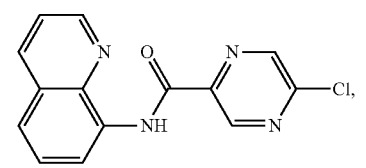
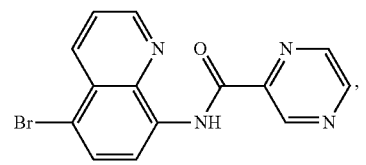
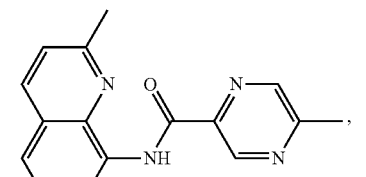
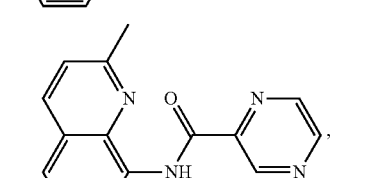
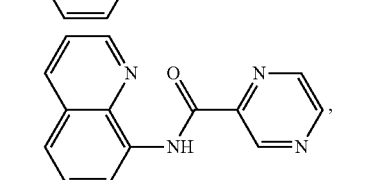
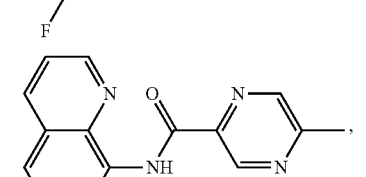
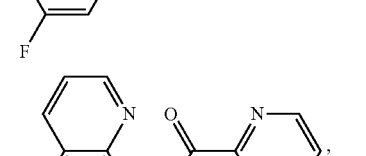
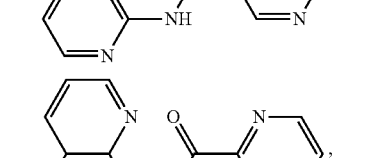
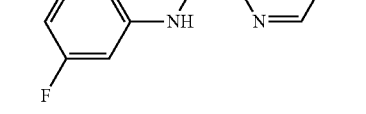
-continued
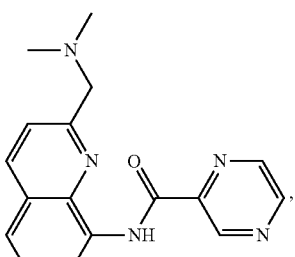
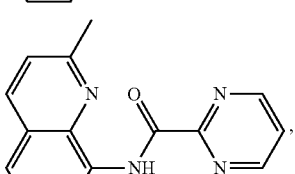
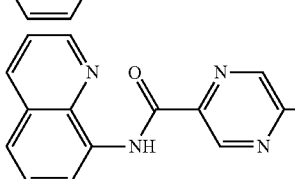
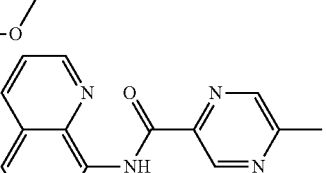
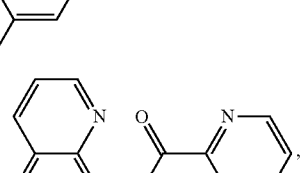
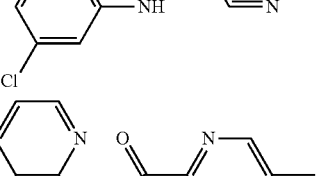
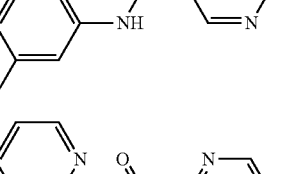
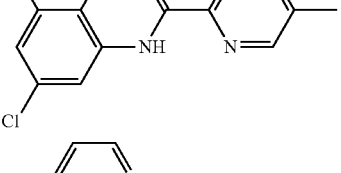
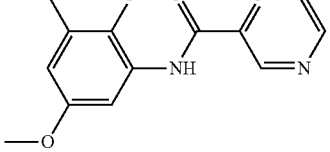

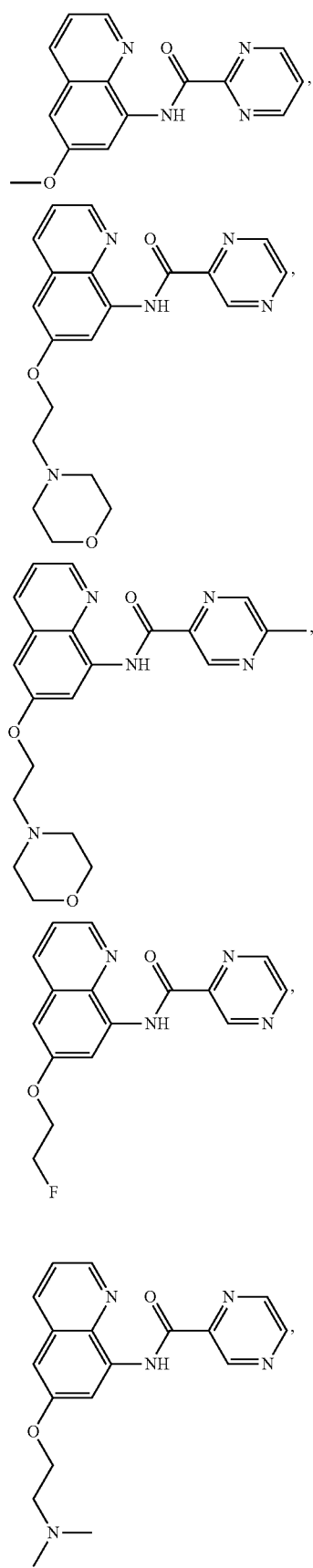
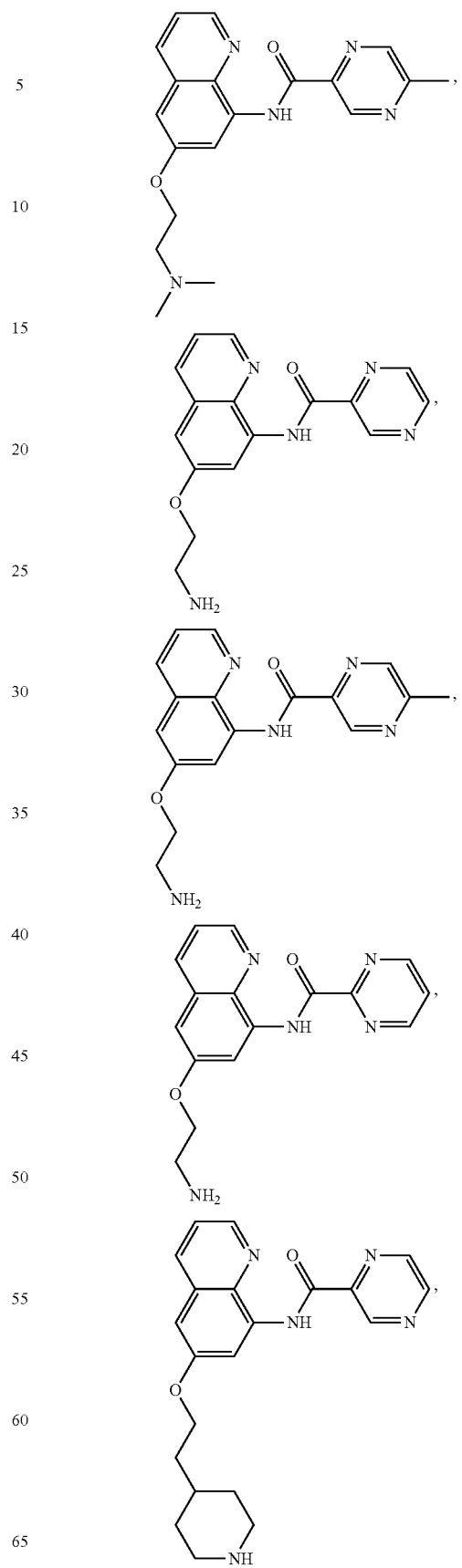

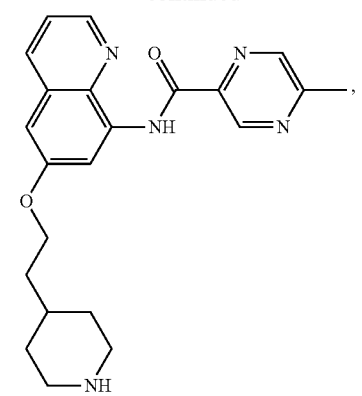
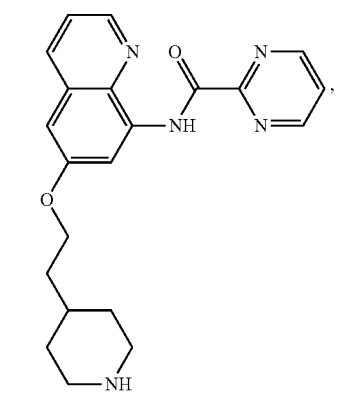
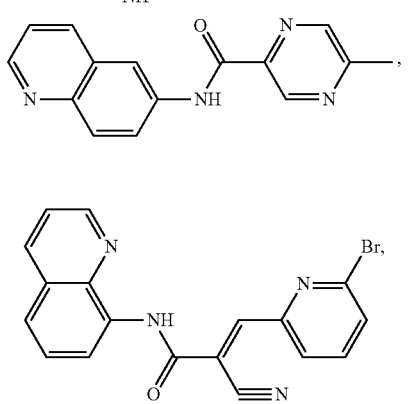
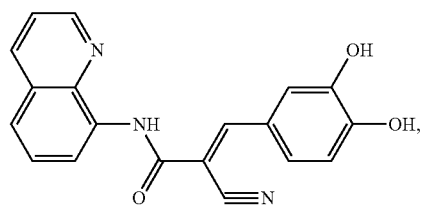
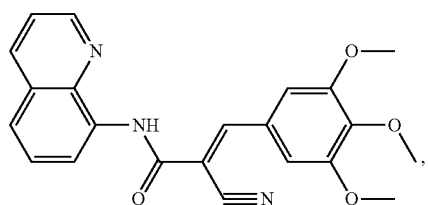
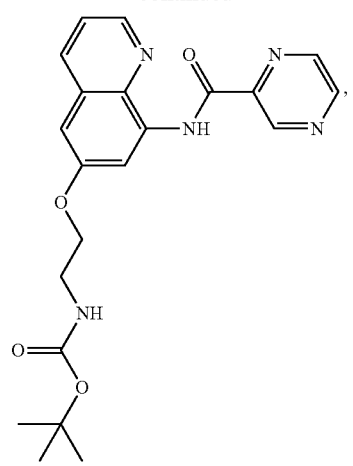
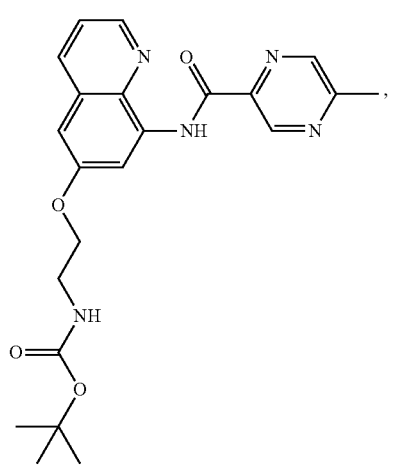
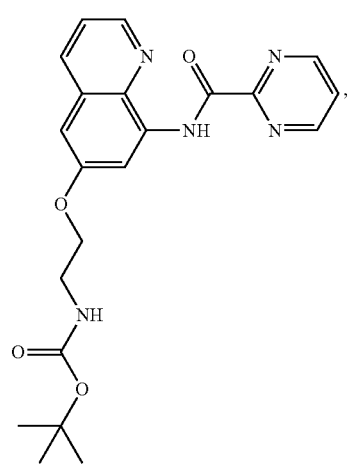

35
-continued
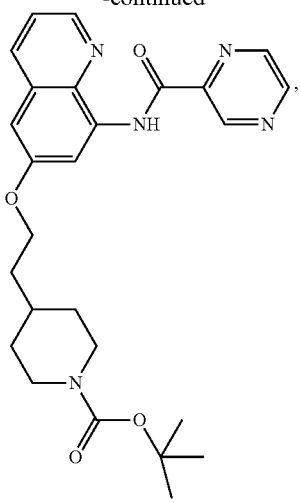
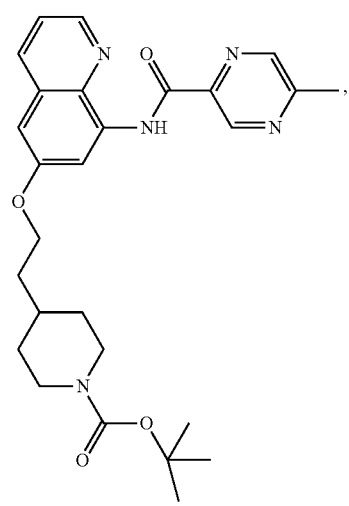
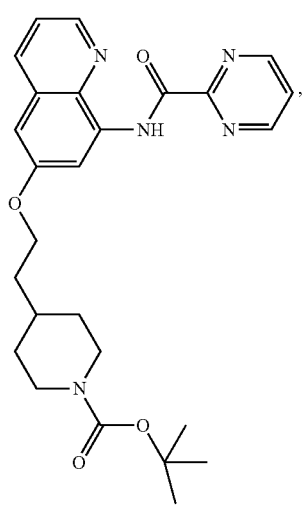
36
-continued
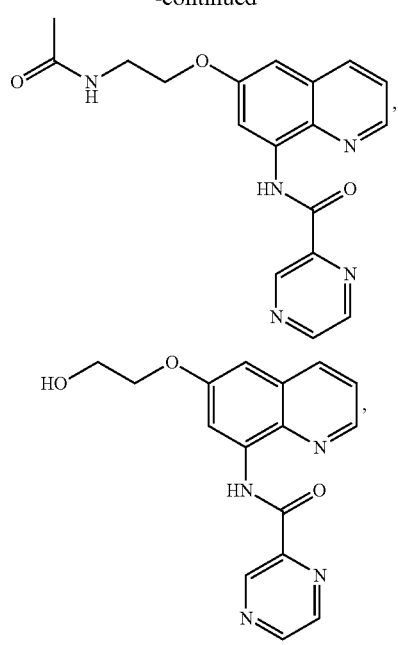
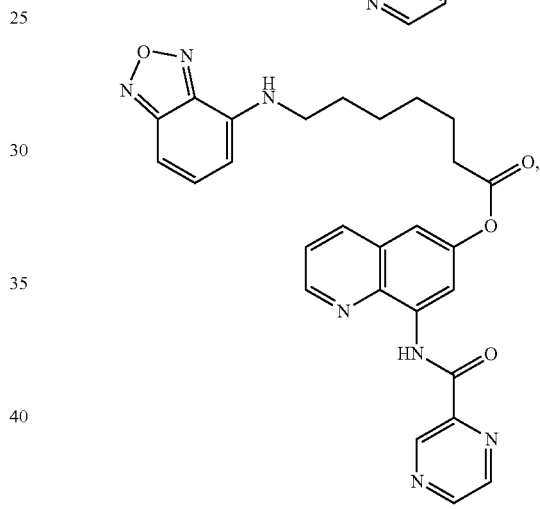
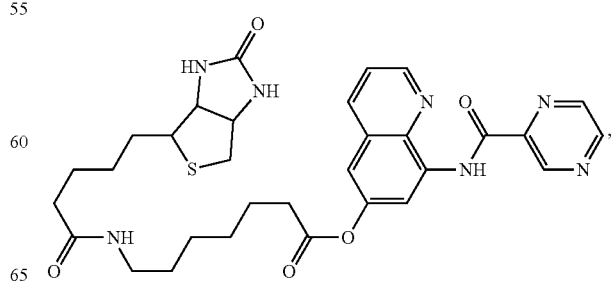

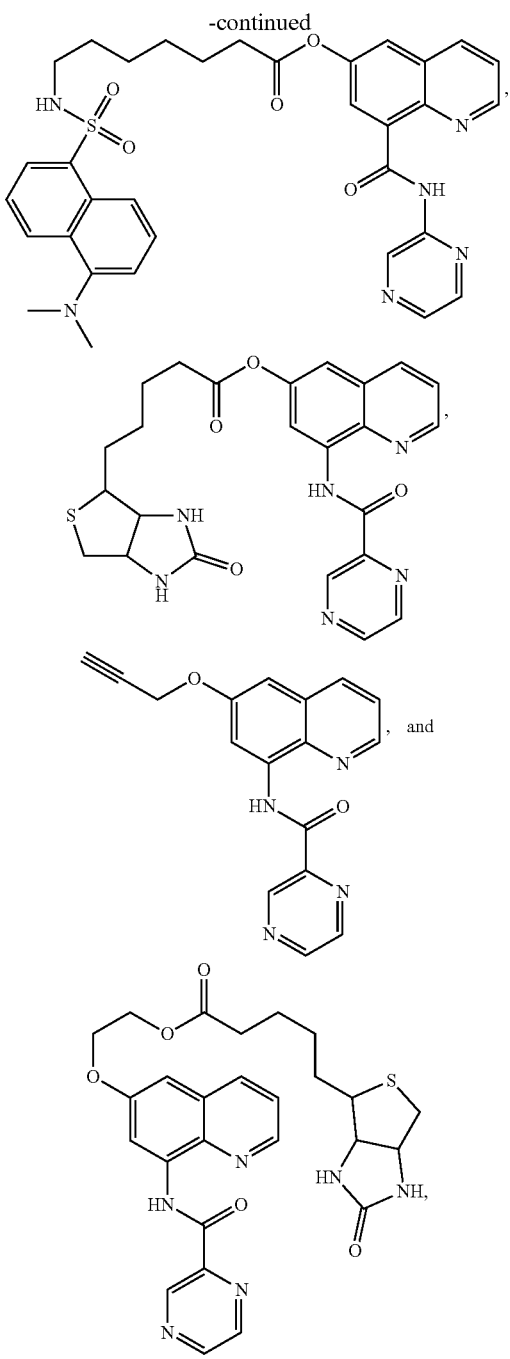

or a pharmaceutically acceptable salt, solvate, or prodrug thereof.

In some embodiments, the present invention provides the following compound:

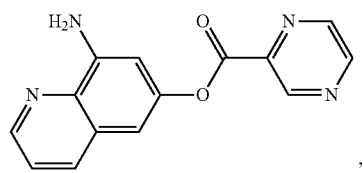 [SMILES: Nc1cc(OC(=O)c2cnccn2)cc2cccnc12]

or a pharmaceutically acceptable salt, solvate, or prodrug thereof.

An important aspect of the present invention is that compounds of the invention induce cell cycle arrest and/or apoptosis and also potentiate the induction of cell cycle arrest and/or apoptosis either alone or in response to additional apoptosis induction signals. Therefore, it is contemplated that these compounds sensitize cells to induction of cell cycle arrest and/or apoptosis, including cells that are resistant to such inducing stimuli. The compounds of the present invention can be used to induce apoptosis in any disorder that can be treated, ameliorated, or prevented by the induction of apoptosis.

In some embodiments, the compositions and methods of the present invention are used to treat diseased cells, tissues, organs, or pathological conditions and/or disease states in an animal (e.g., a mammalian patient including, but not limited to, humans and veterinary animals). In this regard, various diseases and pathologies are amenable to treatment or prophylaxis using the present methods and compositions. A non-limiting exemplary list of these diseases and conditions includes, but is not limited to, pancreatic cancer, breast cancer, prostate cancer, lymphoma, skin cancer, colon cancer, melanoma, malignant melanoma, ovarian cancer, brain cancer, primary brain carcinoma, head-neck cancer, glioma, glioblastoma, liver cancer, bladder cancer, non-small cell lung cancer, head or neck carcinoma, breast carcinoma, ovarian carcinoma, lung carcinoma, small-cell lung carcinoma, Wilms' tumor, cervical carcinoma, testicular carcinoma, bladder carcinoma, pancreatic carcinoma, stomach carcinoma, colon carcinoma, prostatic carcinoma, genitourinary carcinoma, thyroid carcinoma, esophageal carcinoma, myeloma, multiple myeloma, adrenal carcinoma, renal cell carcinoma, endometrial carcinoma, adrenal cortex carcinoma, malignant pancreatic insulinoma, malignant carcinoid carcinoma, choriocarcinoma, mycosis fungoides, malignant hypercalcemia, cervical hyperplasia, leukemia, acute lymphocytic leukemia, chronic lymphocytic leukemia, acute myelogenous leukemia, chronic myelogenous leukemia, chronic granulocytic leukemia, acute granulocytic leukemia, hairy cell leukemia, neuroblastoma, rhabdomyosarcoma, Kaposi's sarcoma, polycythemia vera, essential thrombocytosis, Hodgkin's disease, non-Hodgkin's lymphoma, soft-tissue sarcoma, osteogenic sarcoma, primary macroglobulinemia, and retinoblastoma, and the like, T and B cell mediated autoimmune diseases; inflammatory diseases; infections; hyperproliferative diseases; AIDS; degenerative conditions, vascular diseases, and the like. In some embodiments, the cancer cells being treated are metastatic. In other embodiments, the cancer cells being treated are resistant to anticancer agents.

In other embodiments, the disorder is any disorder having cells characterized by reduced gene expression of one or more genes associated with the stress response pathway (e.g., GDF15, ATF3, DDIT3, and HSPA5). In some embodiments, the compounds of the present invention are able to increase expression of one or more genes associated with the stress response pathway (e.g., GDF15, ATF3, DDIT3, and HSPA5).

In some embodiments, the disorder is any disorder having cells with a reduced ability to undergo autophagy. For example, in some embodiments, the disorder in any disorder having increased expression of genes associated with inhibited autophagy (e.g., WIPI1, GABARAPL1, and MAP1LC3B). In some embodiments, the compounds of the present invention are able to inhibit expression of genes associated with inhibited autophagy (e.g., WIPI1, GABARAPL1, and MAP1LC3B).

Some embodiments of the present invention provide methods for administering an effective amount of a compound of the invention and at least one additional therapeutic agent (including, but not limited to, chemotherapeutic antineoplastics, apoptosis-modulating agents, antimicrobials, antivirals, antifungals, and anti-inflammatory agents) and/or therapeutic technique (e.g., surgical intervention, and/or radiotherapies). In a particular embodiment, the additional therapeutic agent(s) is an anticancer agent.

A number of suitable anticancer agents are contemplated for use in the methods of the present invention. Indeed, the present invention contemplates, but is not limited to, administration of numerous anticancer agents such as: agents that induce apoptosis; polynucleotides (e.g., anti-sense, ribozymes, siRNA); polypeptides (e.g., enzymes and antibodies); biological mimetics; alkaloids; alkylating agents; antitumor antibiotics; antimetabolites; hormones; platinum compounds; monoclonal or polyclonal antibodies (e.g., antibodies conjugated with anticancer drugs, toxins, defensins), toxins; radionuclides; biological response modifiers (e.g., interferons (e.g., IFN-α) and interleukins (e.g., IL-2)); adoptive immunotherapy agents; hematopoietic growth factors; agents that induce tumor cell differentiation (e.g., all-trans-retinoic acid); gene therapy reagents (e.g., antisense therapy reagents and nucleotides); tumor vaccines; angiogenesis inhibitors; proteosome inhibitors: NF-κB modulators; anti-CDK compounds; HDAC inhibitors; and the like. Numerous other examples of chemotherapeutic compounds and anticancer therapies suitable for co-administration with the disclosed compounds are known to those skilled in the art.

In certain embodiments, anticancer agents comprise agents that induce or stimulate apoptosis. Agents that induce apoptosis include, but are not limited to, radiation (e.g., X-rays, gamma rays, UV); tumor necrosis factor (TNF)-related factors (e.g., TNF family receptor proteins, TNF family ligands, TRAIL, antibodies to TRAIL-R1 or TRAIL-R2); kinase inhibitors (e.g., epidermal growth factor receptor (EGFR) kinase inhibitor, vascular growth factor receptor (VGFR) kinase inhibitor, fibroblast growth factor receptor (FGFR) kinase inhibitor, platelet-derived growth factor receptor (PDGFR) kinase inhibitor, and Bcr-Abl kinase inhibitors (such as GLEEVEC)); antisense molecules; antibodies (e.g., HERCEPTIN, RITUXAN, ZEVALIN, and AVASTIN); anti-estrogens (e.g., raloxifene and tamoxifen); anti-androgens (e.g., flutamide, bicalutamide, finasteride, aminoglutethamide, ketoconazole, and corticosteroids); cyclooxygenase 2 (COX-2) inhibitors (e.g., celecoxib, meloxicam, NS-398, and non-steroidal anti-inflammatory drugs (NSAIDs)); anti-inflammatory drugs (e.g., butazolidin, DECADRON, DELTASONE, dexamethasone, dexamethasone intensol, DEXONE, HEXADROL, hydroxychloroquine, METICORTEN, ORADEXON, ORASONE, oxyphenbutazone, PEDIAPRED, phenylbutazone, PLAQUENIL, prednisolone, prednisone, PRELONE, and TANDEARIL); and cancer chemotherapeutic drugs (e.g., irinotecan (CAMPTOSAR), CPT-11, fludarabine (FLUDARA), dacarbazine (DTIC), dexamethasone, mitoxantrone, MYLOTARG, VP-16, cisplatin, carboplatin, oxaliplatin, 5-FU, doxorubicin, gemcitabine, bortezomib, gefitinib, bevacizumab, TAXOTERE or TAXOL); cellular signaling molecules; ceramides and cytokines; staurosporine, and the like.

In still other embodiments, the compositions and methods of the present invention provide a compound of the invention and at least one anti-hyperproliferative or antineoplastic agent selected from alkylating agents, antimetabolites, and natural products (e.g., herbs and other plant and/or animal derived compounds).

Alkylating agents suitable for use in the present compositions and methods include, but are not limited to: 1) nitrogen mustards (e.g., mechlorethamine, cyclophosphamide, ifosfamide, melphalan (L-sarcolysin); and chlorambucil); 2) ethylenimines and methylmelamines (e.g., hexamethylmelamine and thiotepa); 3) alkyl sulfonates (e.g., busulfan); 4) nitrosoureas (e.g., carmustine (BCNU); lomustine (CCNU); semustine (methyl-CCNU); and streptozocin (streptozotocin)); and 5) triazenes (e.g., dacarbazine (DTIC; dimethyltriazenoimid-azolecarboxamide).

In some embodiments, antimetabolites suitable for use in the present compositions and methods include, but are not limited to: 1) folic acid analogs (e.g., methotrexate (amethopterin)); 2) pyrimidine analogs (e.g., fluorouracil (5-fluorouracil; 5-FU), floxuridine (fluorode-oxyuridine; FudR), and cytarabine (cytosine arabinoside)); and 3) purine analogs (e.g., mercaptopurine (6-mercaptopurine; 6-MP), thioguanine (6-thioguanine; TG), and pentostatin (2'-deoxycoformycin)).

In still further embodiments, chemotherapeutic agents suitable for use in the compositions and methods of the present invention include, but are not limited to: 1) vinca alkaloids (e.g., vinblastine (VLB), vincristine); 2) epipodophyllotoxins (e.g., etoposide and teniposide); 3) antibiotics (e.g., dactinomycin (actinomycin D), daunorubicin (daunomycin; rubidomycin), doxorubicin, bleomycin, plicamycin (mithramycin), and mitomycin (mitomycin C)); 4) enzymes (e.g., L-asparaginase); 5) biological response modifiers (e.g., interferon-alfa); 6) platinum coordinating complexes (e.g., cisplatin (cis-DDP) and carboplatin); 7) anthracenediones (e.g., mitoxantrone); 8) substituted ureas (e.g., hydroxyurea); 9) methylhydrazine derivatives (e.g., procarbazine (N-methylhydrazine; MIH)); 10) adrenocortical suppressants (e.g., mitotane (o,p'-DDD) and aminoglutethimide); 11) adrenocorticosteroids (e.g., prednisone); 12) progestins (e.g., hydroxyprogesterone caproate, medroxyprogesterone acetate, and megestrol acetate); 13) estrogens (e.g., diethylstilbestrol and ethinyl estradiol); 14) antiestrogens (e.g., tamoxifen); 15) androgens (e.g., testosterone propionate and fluoxymesterone); 16) antiandrogens (e.g., flutamide): and 17) gonadotropin-releasing hormone analogs (e.g., leuprolide).

Any oncolytic agent that is routinely used in a cancer therapy context finds use in the compositions and methods of the present invention. For example, the U.S. Food and Drug Administration maintains a formulary of oncolytic agents approved for use in the United States. International counterpart agencies to the U.S.F.D.A. maintain similar formularies. Table 15 provides a list of exemplary antineoplastic agents approved for use in the U.S. Those skilled in the art will appreciate that the "product labels" required on all U.S. approved chemotherapeutics describe approved indications, dosing information, toxicity data, and the like, for the exemplary agents.

TABLE 15

| | | |
|---|---|---|
| Aldesleukin (des-alanyl-1, serine-125 human interleukin-2) | Proleukin | Chiron Corp., Emeryville, CA |
| Alemtuzumab (IgG1κ anti CD52 antibody) | Campath | Millennium and ILEX Partners, LP, Cambridge, MA |
| Alitretinoin (9-cis-retinoic acid) | Panretin | Ligand Pharmaceuticals, Inc., San Diego CA |
| Allopurinol (1,5-dihydro-4H-pyrazolo[3,4-d]pyrimidin-4-one monosodium salt) | Zyloprim | GlaxoSmithKline, Research Triangle Park, NC |
| Altretamine (N,N,N',N',N'',N''-hexamethyl-1,3,5-triazine-2,4,6-triamine) | Hexalen | US Bioscience, West Conshohocken, PA |
| Amifostine (ethanethiol, 2-[(3-aminopropyl)amino]-, dihydrogen phosphate (ester)) | Ethyol | US Bioscience |
| Anastrozole (1,3-Benzenediacetonitrile, a,a,a',a'-tetramethyl-5-(1H-1,2,4-triazol-1-ylmethyl)) | Arimidex | AstraZeneca Pharmaceuticals, LP, Wilmington, DE |
| Arsenic trioxide | Trisenox | Cell Therapeutic, Inc., Seattle, WA |
| Asparaginase (L-asparagine amidohydrolase, type EC-2) | Elspar | Merck & Co., Inc., Whitehouse Station, NJ |
| BCG Live (lyophilized preparation of an attenuated strain of *Mycobacterium bovis* (*Bacillus Calmette-Gukin* [BCG], substrain Montreal) | TICE BCG | Organon Teknika, Corp., Durham, NC |
| bexarotene capsules (4-[1-(5,6,7,8-tetrahydro-3,5,5,8,8-pentamethyl-2-napthalenyl) ethenyl] benzoic acid) | Targretin | Ligand Pharmaceuticals |
| bexarotene gel | Targretin | Ligand Pharmaceuticals |
| Bleomycin (cytotoxic glycopeptide antibiotics produced by *Streptomyces verticillus*; bleomycin $A_2$ and bleomycin $B_2$) | Blenoxane | Bristol-Myers Squibb Co., NY, NY |
| Capecitabine (5'-deoxy-5-fluoro-N-[(pentyloxy)carbonyl]-cytidine) | Xeloda | Roche |
| Carboplatin (platinum, diammine [1,1-cyclobutanedicarboxylato(2-)-0,0']-, (SP-4-2)) | Paraplatin | Bristol-Myers Squibb |
| Carmustine (1,3-bis(2-chloroethyl)-1-nitrosourea) | BCNU, BiCNU | Bristol-Myers Squibb |
| Carmustine with Polifeprosan 20 Implant | Gliadel Wafer | Guilford Pharmaceuticals, Inc., Baltimore, MD |
| Celecoxib (as 4-[5-(4-methylphenyl)-3-(trifluoromethyl)-1H-pyrazol-1-yl] benzenesulfonamide) | Celebrex | Searle Pharmaceuticals, England |
| Chlorambucil (4-[bis(2chlorethyl)amino]benzenebutanoic acid) | Leukeran | GlaxoSmithKline |
| Cisplatin ($PtCl_2H_6N_2$) | Platinol | Bristol-Myers Squibb |
| Cladribine (2-chloro-2'-deoxy-b-D-adenosine) | Leustatin, 2-CdA | R. W. Johnson Pharmaceutical Research Institute, Raritan, NJ |
| Cyclophosphamide (2-[bis(2-chloroethyl)amino] tetrahydro-2H-13,2-oxazaphosphorine 2-oxide monohydrate) | Cytoxan, Neosar | Bristol-Myers Squibb |
| Cytarabine (1-b-D-Arabinofuranosylcytosine, $C_9H_{13}N_3O_5$) | Cytosar-U | Pharmacia & Upjohn Company |
| cytarabine liposomal | DepoCyt | Skye Pharmaceuticals, Inc., San Diego, CA |
| Dacarbazine (5-(3,3-dimethyl-l-triazeno)-imidazole-4-carboxamide (DTIC)) | DTIC-Dome | Bayer AG, Leverkusen, Germany |

TABLE 15-continued

| | | |
|---|---|---|
| Dactinomycin, actinomycin D (actinomycin produced by *Streptomyces parvullus*, $C_{62}H_{86}N_{12}O_{16}$) | Cosmegen | Merck |
| Darbepoetin alfa (recombinant peptide) | Aranesp | Amgen, Inc., Thousand Oaks, CA |
| daunorubicin liposomal ((8S-cis)-8-acetyl-10-[(3-amino-2,3,6-trideoxy-á-L-lyxo-hexopyranosyl)oxy]-7,8,9,10-tetrahydro-6,8,11-trihydroxy-1-methoxy-5,12-naphthacenedione hydrochloride) | DanuoXome | Nexstar Pharmaceuticals, Inc., Boulder, CO |
| Daunorubicin HCl, daunomycin ((1S,3S)-3-Acetyl-1,2,3,4,6,11-hexahydro-3,5,12-trihydroxy-10-methoxy-6,11-dioxo-1-naphthacenyl 3-amino-2,3,6-trideoxy-(alpha)-L-lyxo-hexopyranoside hydrochloride) | Cerubidine | Wyeth Ayerst, Madison, NJ |
| Denileukin diftitox (recombinant peptide) | Ontak | Seragen, Inc., Hopkinton, MA |
| Dexrazoxane ((S)-4,4'-(1-methyl-1,2-ethanediyl)bis-2,6-piperazinedione) | Zinecard | Pharmacia & Upjohn Company |
| Docetaxel ((2R,3S)-N-carboxy-3-phenylisoserine, N-tert-butyl ester, 13-ester with 5b-20-epoxy-12a,4,7b,10b,13a-hexahydroxytax-11-en-9-one 4-acetate 2-benzoate, trihydrate) | Taxotere | Aventis Pharmaceuticals, Inc., Bridgewater, NJ |
| Doxorubicin HCl (8S,10S)-10-[(3-amino-2,3,6-trideoxy-a-L-lyxo-hexopyranosyl)oxy]-8-glycolyl-7,8,9,10-tetrahydro-6,8,11-trihydroxy-1-methoxy-5,12-naphthacenedione hydrochloride) | Adriamycin, Rubex | Pharmacia & Upjohn Company |
| doxorubicin | Adriamycin PFS Intravenous injection | Pharmacia & Upjohn Company |
| doxorubicin liposomal | Doxil | Sequs Pharmaceuticals, Inc., Menlo park, CA |
| dromostanolone propionate (17b-Hydroxy-2a-methyl-5a-androstan-3-one propionate) | Dromostanolone | Eli Lilly & Company, Indianapolis, IN |
| dromostanolone propionate | Masterone injection | Syntex, Corp., Palo Alto, CA |
| Elliott's B Solution | Elliott's B Solution | Orphan Medical, Inc |
| Epirubicin ((8S-cis)-10-[(3-amino-2,3,6-trideoxy-a-L-arabino-hexopyranosyl)oxy]-7,8,9,10-tetrahydro-6,8,11-trihydroxy-8-(hydroxyacetyl)-1-methoxy-5,12-naphthacenedione hydrochloride) | Ellence | Pharmacia & Upjohn Company |
| Epoetin alfa (recombinant peptide) | Epogen | Amgen, Inc |
| Estramustine (estra-1,3,5(10)-triene-3,17-diol(17(beta))-, 3-[bis(2-chloroethyl)carbamate] 17-(dihydrogen phosphate), disodium salt, monohydrate, or estradiol 3-[bis(2-chloroethyl)carbamate] 17-(dihydrogen phosphate), disodium salt, monohydrate) | Emcyt | Pharmacia & Upjohn Company |
| Etoposide phosphate (4'-Demethylepipodophyllotoxin 9-[4,6-O-(R)-ethylidene-(beta)-D-glucopyranoside], 4'-(dihydrogen phosphate)) | Etopophos | Bristol-Myers Squibb |
| etoposide, VP-16 (4'-demethylepipodophyllotoxin 9-[4,6-0-(R)-ethylidene-(beta)-D-glucopyranoside]) | Vepesid | Bristol-Myers Squibb |
| Exemestane (6-methylenandrosta-1,4-diene-3,17-dione) | Aromasin | Pharmacia & Upjohn Company |
| Filgrastim (r-metHuG-CSF) | Neupogen | Amgen, Inc |
| floxuridine (intraarterial) (2'-deoxy-5-fluorouridine) | FUDR | Roche |

TABLE 15-continued

| | | |
|---|---|---|
| Fludarabine (fluorinated nucleotide analog of the antiviral agent vidarabine, 9-b-D-arabinofuranosyladenine (ara-A)) | Fludara | Berlex Laboratories, Inc., Cedar Knolls, NJ |
| Fluorouracil, 5-FU (5-fluoro-2,4(1H,3H)-pyrimidinedione) | Adrucil | ICN Pharmaceuticals, Inc., Humacao, Puerto Rico |
| Fulvestrant (7-alpha-[9-(4,4,5,5,5-penta fluoropentylsulphinyl) nonyl]estra-1,3,5-(10)-triene-3,17-beta-diol) | Faslodex | IPR Pharmaceuticals, Guayama, Puerto Rico |
| Gemcitabine (2'-deoxy-2',2'-difluorocytidine monohydrochloride (b-isomer)) | Gemzar | Eli Lilly |
| Gemtuzumab Ozogamicin (anti-CD33 hP67.6) | Mylotarg | Wyeth Ayerst |
| Goserelin acetate | Zoladex Implant | AstraZeneca Pharmaceuticals |
| Hydroxyurea | Hydrea | Bristol-Myers Squibb |
| Ibritumomab Tiuxetan (immunoconjugate resulting from a thiourea covalent bond between the monoclonal antibody Ibritumomab and the linker-chelator tiuxetan [N-[2-bis(carboxymethyl)amino]-3-(p-isothiocyanatophenyl)-propyl]-[N-[2-bis(carboxymethyl)amino]-2-(methyl)-ethyl]glycine) | Zevalin | Biogen IDEC, Inc., Cambridge MA |
| Idarubicin (5,12-Naphthacenedione, 9-acetyl-7-[(3-amino-2,3,6-trideoxy-(alpha)-L-lyxo-hexopyranosyl)oxy]-7,8,9,10-tetrahydro-6,9,11-trihydroxyhydrochloride, (7S-cis)) | Idamycin | Pharmacia & Upjohn Company |
| Ifosfamide (3-(2-chloroethyl)-2-[(2-chloroethyl)amino]tetrahydro-2H-1,3,2-oxazaphosphorine 2-oxide) | IFEX | Bristol-Myers Squibb |
| Imatinib Mesilate (4-[(4-Methyl-1-piperazinyl)methyl]-N-[4-methyl-3-[[4-(3-pyridinyl)-2-pyrimidinyl]amino]-phenyl]benzamide methanesulfonate) | Gleevec | Novartis AG, Basel, Switzerland |
| Interferon alfa-2a (recombinant peptide) | Roferon-A | Hoffmann-La Roche, Inc., Nutley, NJ |
| Interferon alfa-2b (recombinant peptide) | Intron A (Lyophilized Betaseron) | Schering AG, Berlin, Germany |
| Irinotecan HCl ((4S)-4,11-diethyl-4-hydroxy-9-[(4-piperi-dinopiperidino)carbonyloxy]-1H-pyrano[3',4': 6,7] indolizino[1,2-b] quinoline-3,14(4H,12H) dione hydrochloride trihydrate) | Camptosar | Pharmacia & Upjohn Company |
| Letrozole (4,4'-(1H-1,2,4-Triazol-1-ylmethylene) dibenzonitrile) | Femara | Novartis |
| Leucovorin (L-Glutamic acid, N[4[[(2amino-5-formyl1,4,5,6,7,8 hexahydro4oxo6-pteridinyl)methyl]amino]benzoyl], calcium salt (1:1)) | Wellcovorin, Leucovorin | Immunex, Corp., Seattle, WA |
| Levamisole HCl ((−)-(S)-2,3,5,6-tetrahydro-6-phenylimidazo [2,1-b] thiazole monohydrochloride $C_{11}H_{12}N_2S \cdot HCl$) | Ergamisol | Janssen Research Foundation, Titusville, NJ |
| Lomustine (1-(2-chloro-ethyl)-3-cyclohexyl-1-nitrosourea) | CeeNU | Bristol-Myers Squibb |
| Mechlorethamine, nitrogen mustard (2-chloro-N-(2-chloroethyl)-N-methylethanamine hydrochloride) | Mustargen | Merck |
| Megestrol acetate 17α(acetyloxy)-6-methylpregna-4,6-diene-3,20-dione | Megace | Bristol-Myers Squibb |
| Melphalan, L-PAM (4-[bis(2-chloroethyl) amino]-L-phenylalanine) | Alkeran | GlaxoSmithKline |

TABLE 15-continued

| | | |
|---|---|---|
| Mercaptopurine, 6-MP (1,7-dihydro-6H-purine-6-thione monohydrate) | Purinethol | GlaxoSmithKline |
| Mesna (sodium 2-mercaptoethane sulfonate) | Mesnex | Asta Medica |
| Methotrexate (N-[4-[[(2,4-diamino-6-pteridinyl)methyl]methylamino]benzoyl]-L-glutamic acid) | Methotrexate | Lederle Laboratories |
| Methoxsalen (9-methoxy-7H-furo[3,2-g][1]-benzopyran-7-one) | Uvadex | Therakos, Inc., Way Exton, Pa |
| Mitomycin C | Mutamycin | Bristol-Myers Squibb |
| mitomycin C | Mitozytrex | SuperGen, Inc., Dublin, CA |
| Mitotane (1,1-dichloro-2-(o-chlorophenyl)-2-(p-chlorophenyl) ethane) | Lysodren | Bristol-Myers Squibb |
| Mitoxantrone (1,4-dihydroxy-5,8-bis[[2-[(2-hydroxyethyl)amino]ethyl]amino]-9,10-anthracenedione dihydrochloride) | Novantrone | Immunex Corporation |
| Nandrolone phenpropionate | Durabolin-50 | Organon, Inc., West Orange, NJ |
| Nofetumomab | Verluma | Boehringer Ingelheim Pharma KG, Germany |
| Oprelvekin (IL-11) | Neumega | Genetics Institute, Inc., Alexandria, VA |
| Oxaliplatin (cis-[(1R,2R)-1,2-cyclohexanediamine-N,N'] [oxalato(2-)-O,O'] platinum) | Eloxatin | Sanofi Synthelabo, Inc., NY, NY |
| Paclitaxel (5ß,20-Epoxy-1,2a,4,7ß,10ß,13a-hexahydroxytax-11-en-9-one 4,10-diacetate 2-benzoate 13-ester with (2R,3S)-N-benzoyl-3-phenylisoserine) | TAXOL | Bristol-Myers Squibb |
| Pamidronate (phosphonic acid (3-amino-1-hydroxypropylidene) bis-, disodium salt, pentahydrate, (APD)) | Aredia | Novartis |
| Pegademase ((monomethoxypolyethylene glycol succinimidyl) 11-17-adenosine deaminase) | Adagen (Pegademase Bovine) | Enzon Pharmaceuticals, Inc., Bridgewater, NJ |
| Pegaspargase (monomethoxypolyethylene glycol succinimidyl L-asparaginase) | Oncaspar | Enzon |
| Pegfilgrastim (covalent conjugate of recombinant methionyl human G-CSF (Filgrastim) and monomethoxypolyethylene glycol) | Neulasta | Amgen, Inc |
| Pentostatin | Nipent | Parke-Davis Pharmaceutical Co., Rockville, MD |
| Pipobroman | Vercyte | Abbott Laboratories, Abbott Park, IL |
| Plicamycin, Mithramycin (antibiotic produced by Streptomyces plicatus) | Mithracin | Pfizer, Inc., NY, NY |
| Porfimer sodium | Photofrin | QLT Phototherapeutics, Inc., Vancouver, Canada |
| Procarbazine (N-isopropyl-μ-(2-methylhydrazino)-p-toluamide monohydrochloride) | Matulane | Sigma Tau Pharmaceuticals, Inc., Gaithersburg, MD |
| Quinacrine (6-chloro-9-(1-methyl-4-diethyl-amine) butylamino-2-methoxyacridine) | Atabrine | Abbott Labs |
| Rasburicase (recombinant peptide) | Elitek | Sanofi-Synthelabo, Inc., |
| Rituximab (recombinant anti-CD20 antibody) | Rituxan | Genentech, Inc., South San Francisco, CA |
| Sargramostim (recombinant peptide) | Prokine | Immunex Corp |
| Streptozocin (streptozocin 2-deoxy-2-[[[(methylnitrosoamino)carbonyl]amino]-a(and b)-D-glucopyranose and 220 mg citric acid anhydrous) | Zanosar | Pharmacia & Upjohn Company |

TABLE 15-continued

| | | |
|---|---|---|
| Talc (Mg$_3$Si$_4$O$_{10}$(OH)$_2$) | Sclerosol | Bryan, Corp., Woburn, MA |
| Tamoxifen ((Z)2-[4-(1,2-diphenyl-1-butenyl) phenoxy]-N,N-dimethylethanamine 2-hydroxy-1,2,3-propanetricarboxylate (1:1)) | Nolvadex | AstraZeneca Pharmaceuticals |
| Temozolomide (3,4-dihydro-3-methyl-4-oxoimidazo[5,1-d]-as-tetrazine-8-carboxamide) | Temodar | Schering |
| teniposide, VM-26 (4'-demethylepipodophyllotoxin 9-[4,6-0-(R)-2-thenylidene-(beta)-D-glucopyranoside]) | Vumon | Bristol-Myers Squibb |
| Testolactone (13-hydroxy-3-oxo-13,17-secoandrosta-1,4-dien-17-oic acid [dgr]-lactone) | Teslac | Bristol-Myers Squibb |
| Thioguanine, 6-TG (2-amino-1,7-dihydro-6H-purine-6-thione) | Thioguanine | GlaxoSmithKline |
| Thiotepa (Aziridine, 1,1',1"-phosphinothioylidynetris-, or Tris (1-aziridinyl) phosphine sulfide) | Thioplex | Immunex Corporation |
| Topotecan HCl ((S)-10-[(dimethylamino) methyl]-4-ethyl-4,9-dihydroxy-1H-pyrano[3',4': 6,7] indolizino [1,2-b] quinoline-3,14-(4H,12H)-dione monohydrochloride) | Hycamtin | GlaxoSmithKline |
| Toremifene (2-(p-[(Z)-4-chloro-1,2-diphenyl-1-butenyl]-phenoxy)-N,N-dimethylethylamine citrate (1:1)) | Fareston | Roberts Pharmaceutical Corp., Eatontown, NJ |
| Tositumomab, I 131 Tositumomab (recombinant murine immunotherapeutic monoclonal IgG$_{2a}$ lambda anti-CD20 antibody (I 131 is a radioimmunotherapeutic antibody)) | Bexxar | Corixa Corp., Seattle, WA |
| Trastuzumab (recombinant monoclonal IgG$_1$ kappa anti-HER2 antibody) | Herceptin | Genentech, Inc |
| Tretinoin, ATRA (all-trans retinoic acid) | Vesanoid | Roche |
| Uracil Mustard | Uracil Mustard Capsules | Roberts Labs |
| Valrubicin, N-trifluoroacetyladriamycin-14-valerate ((2S-cis)-2-[1,2,3,4,6,11-hexahydro-2,5,12-trihydroxy-7 methoxy-6,11-dioxo-[[4 2,3,6-trideoxy-3-[(trifluoroacetyl)-amino-α-L-lyxo-hexopyranosyl]oxy]-2-naphthacenyl]-2-oxoethyl pentanoate) | Valstar | Anthra --> Medeva |
| Vinblastine, Leurocristine (C$_{46}$H$_{56}$N$_4$O$_{10}$•H$_2$SO$_4$) | Velban | Eli Lilly |
| Vincristine (C$_{46}$H$_{56}$N$_4$O$_{10}$•H$_2$SO$_4$) | Oncovin | Eli Lilly |
| Vinorelbine (3',4'-didehydro-4'-deoxy-C'-norvincaleukoblastine [R-(R*,R*)-2,3-dihydroxybutanedioate (1:2) (salt)]) | Navelbine | GlaxoSmithKline |
| Zoledronate, Zoledronic acid ((1-Hydroxy-2-imidazol-1-yl-phosphonoethyl) phosphonic acid monohydrate) | Zometa | Novartis |

Anticancer agents further include compounds which have been identified to have anticancer activity. Examples include, but are not limited to, 3-AP, 12-O-tetradecanoyl-phorbol-13-acetate, 17AAG, 852A, ABI-007, ABR-217620, ABT-751, ADI-PEG 20, AE-941, AG-013736, AGRO100, alanosine, AMG 706, antibody G250, antineoplastons, AP23573, apaziquone, APC8015, atiprimod, ATN-161, atrasenten, azacitidine, BB-10901, BCX-1777, bevacizumab, BG00001, bicalutamide, BMS 247550, bortezomib, bryostatin-1, buserelin, calcitriol, CCI-779, CDB-2914, cefixime, cetuximab, CG0070, cilengitide, clofarabine, combretastatin A4 phosphate, CP-675,206, CP-724,714, CpG 7909, curcumin, decitabine, DENSPM, doxercalciferol, E7070, E7389, ecteinascidin 743, efaproxiral, eflornithine, EKB-569, enzastaurin, erlotinib, exisulind, fenretinide, flavopiridol, fludarabine, flutamide, fotemustine, FR901228, G17DT, galiximab, gefitinib, genistein, glufosfamide, GTI-2040, histrelin, HKI-272, homoharringtonine, HSPPC-96, hu14.18-interleukin-2 fusion protein, HuMax-CD4, iloprost, imiquimod, infliximab, interleukin-12, IPI-504, irofulven, ixabepilone, lapatinib, lenalidomide, lestaurtinib, leuprolide, LMB-9 immunotoxin, lonafarnib, luniliximab, mafosfamide, MB07133, MDX-010, MLN2704, monoclonal antibody 3F8, monoclonal antibody J591, motexafin, MS-275, MVA-MUC1-IL2, nilutamide, nitrocamptothecin, nolatrexed dihydrochloride, nolvadex, NS-9, O6-benzylguanine, oblimersen sodium, ONYX-015, oregovomab, OSI-774, panitumumab, paraplatin, PD-0325901, pemetrexed, PHY906, pioglitazone, pirfenidone, pixantrone, PS-341, PSC 833, PXD101, pyrazoloacridine, R115777, RAD001, ranpirnase, rebeccamycin analogue, rhuAngiostatin protein, rhuMab 2C4, rosiglitazone, rubitecan, S-1, S-8184, satraplatin, SB-, 15992, SGN-0010, SGN-40, sorafenib, SR31747A, ST1571, SU011248, suberoylanilide hydroxamic acid, suramin, talabostat, talampanel, tariquidar, temsirolimus, TGFa-PE38 immunotoxin, thalidomide, thymalfasin, tipifarnib, tirapazamine, TLK286, trabectedin, trimetrexate glucuronate, TroVax, UCN-1, valproic acid, vinflunine, VNP40101M, vollociximab, vorinostat, VX-680, ZD1839, ZD6474, zileuton, and zosuquidar trihydrochloride.

For a more detailed description of anticancer agents and other therapeutic agents, those skilled in the art are referred to any number of instructive manuals including, but not limited to, the Physician's Desk Reference and to Goodman and Gilman's "Pharmaceutical Basis of Therapeutics" tenth edition, Eds. Hardman et al., 2002.

The present invention provides methods for administering a compound of the invention with radiation therapy. The invention is not limited by the types, amounts, or delivery and administration systems used to deliver the therapeutic dose of radiation to an animal. For example, the animal may receive photon radiotherapy, particle beam radiation therapy, other types of radiotherapies, and combinations thereof. In some embodiments, the radiation is delivered to the animal using a linear accelerator. In still other embodiments, the radiation is delivered using a gamma knife.

The source of radiation can be external or internal to the animal. External radiation therapy is most common and involves directing a beam of high-energy radiation to a tumor site through the skin using, for instance, a linear accelerator. While the beam of radiation is localized to the tumor site, it is nearly impossible to avoid exposure of normal, healthy tissue. However, external radiation is usually well tolerated by animals. Internal radiation therapy involves implanting a radiation-emitting source, such as beads, wires, pellets, capsules, particles, and the like, inside the body at or near the tumor site including the use of delivery systems that specifically target cancer cells (e.g., using particles attached to cancer cell binding ligands). Such implants can be removed following treatment, or left in the body inactive. Types of internal radiation therapy include, but are not limited to, brachytherapy, interstitial irradiation, intracavity irradiation, radioimmunotherapy, and the like.

The animal may optionally receive radiosensitizers (e.g., metronidazole, misonidazole, intra-arterial Budr, intravenous iododeoxyuridine (IudR), nitroimidazole, 5-substituted-4-nitroimidazoles, 2H-isoindolediones, [[(2-bromoethyl)-amino]methyl]-nitro-1H-imidazole-1-ethanol, nitroaniline derivatives, DNA-affinic hypoxia selective cytotoxins, halogenated DNA ligand, 1,2,4 benzotriazine oxides, 2-nitroimidazole derivatives, fluorine-containing nitroazole derivatives, benzamide, nicotinamide, acridine-intercalator, 5-thiotretrazole derivative, 3-nitro-1,2,4-triazole, 4,5-dinitroimidazole derivative, hydroxylated texaphrins, cisplatin, mitomycin, tiripazamine, nitrosourea, mercaptopurine, methotrexate, fluorouracil, bleomycin, vincristine, carboplatin, epirubicin, doxorubicin, cyclophosphamide, vindesine, etoposide, paclitaxel, heat (hyperthermia), and the like), radioprotectors (e.g., cysteamine, aminoalkyl dihydrogen phosphorothioates, amifostine (WR 2721), IL-1, IL-6, and the like). Radiosensitizers enhance the killing of tumor cells. Radioprotectors protect healthy tissue from the harmful effects of radiation.

Any type of radiation can be administered to an animal, so long as the dose of radiation is tolerated by the animal without unacceptable negative side-effects. Suitable types of radiotherapy include, for example, ionizing (electromagnetic) radiotherapy (e.g., X-rays or gamma rays) or particle beam radiation therapy (e.g., high linear energy radiation). Ionizing radiation is defined as radiation comprising particles or photons that have sufficient energy to produce ionization, i.e., gain or loss of electrons (as described in, for example, U.S. Pat. No. 5,770,581 incorporated herein by reference in its entirety). The effects of radiation can be at least partially controlled by the clinician. In one embodiment, the dose of radiation is fractionated for maximal target cell exposure and reduced toxicity.

In one embodiment, the total dose of radiation administered to an animal is about 0.01 Gray (Gy) to about 100 Gy. In another embodiment, about 10 Gy to about 65 Gy (e.g., about 15 Gy, 20 Gy, 25 Gy, 30 Gy, 35 Gy, 40 Gy, 45 Gy, 50 Gy, 55 Gy, or 60 Gy) are administered over the course of treatment. While in some embodiments a complete dose of radiation can be administered over the course of one day, the total dose is ideally fractionated and administered over several days. Desirably, radiotherapy is administered over the course of at least about 3 days, e.g., at least 5, 7, 10, 14, 17, 21, 25, 28, 32, 35, 38, 42, 46, 52, or 56 days (about 1-8 weeks). Accordingly, a daily dose of radiation will comprise approximately 1-5 Gy (e.g., about 1 Gy, 1.5 Gy, 1.8 Gy, 2 Gy, 2.5 Gy, 2.8 Gy, 3 Gy, 3.2 Gy, 3.5 Gy, 3.8 Gy, 4 Gy, 4.2 Gy, or 4.5 Gy), or 1-2 Gy (e.g., 1.5-2 Gy). The daily dose of radiation should be sufficient to induce destruction of the targeted cells. If stretched over a period, in one embodiment, radiation is not administered every day, thereby allowing the animal to rest and the effects of the therapy to be realized. For example, radiation desirably is administered on 5 consecutive days, and not administered on 2 days, for each week of treatment, thereby allowing 2 days of rest per week. However, radiation can be administered 1 day/week, 2 days/week, 3 days/week, 4 days/week, 5 days/week, 6 days/week, or all 7 days/week, depending on the animal's responsiveness and any potential side effects. Radiation therapy can be initiated at any time in the therapeutic period. In one embodiment, radiation is initiated in week 1 or week 2, and is administered for the remaining duration of the therapeutic period. For example, radiation is administered in weeks 1-6 or in weeks 2-6 of a therapeutic period comprising 6 weeks for treating, for instance, a solid tumor. Alternatively, radiation is administered in weeks 1-5 or weeks 2-5 of a therapeutic period comprising 5 weeks. These exemplary radiotherapy administration schedules are not intended, however, to limit the present invention.

Antimicrobial therapeutic agents may also be used as therapeutic agents in the present invention. Any agent that can kill, inhibit, or otherwise attenuate the function of microbial organisms may be used, as well as any agent contemplated to have such activities. Antimicrobial agents include, but are not limited to, natural and synthetic antibiotics, antibodies, inhibitory proteins (e.g., defensins), antisense nucleic acids, membrane disruptive agents and the like, used alone or in combination. Indeed, any type of antibiotic may be used including, but not limited to, antibacterial agents, antiviral agents, antifungal agents, and the like.

In some embodiments of the present invention, a compound of the invention and one or more therapeutic agents or anticancer agents are administered to an animal under one or more of the following conditions: at different periodicities, at different durations, at different concentrations, by different administration routes, etc. In some embodiments, the compound is administered prior to the therapeutic or anticancer agent, e.g., 0.5, 1, 2, 3, 4, 5, 10, 12, or 18 hours, 1, 2, 3, 4, 5, or 6 days, or 1, 2, 3, or 4 weeks prior to the administration of the therapeutic or anticancer agent. In some embodiments, the compound is administered after the therapeutic or anticancer agent, e.g., 0.5, 1, 2, 3, 4, 5, 10, 12, or 18 hours, 1, 2, 3, 4, 5, or 6 days, or 1, 2, 3, or 4 weeks after the administration of the anticancer agent. In some embodiments, the compound and the therapeutic or anticancer agent are administered concurrently but on different schedules, e.g., the compound is administered daily while the therapeutic or anticancer agent is administered once a week, once every two weeks, once every three weeks, or once every four weeks. In other embodiments, the compound is administered once a week while the therapeutic or anticancer agent is administered daily, once a week, once every two weeks, once every three weeks, or once every four weeks.

Compositions within the scope of this invention include all compositions wherein the compounds of the present invention are contained in an amount which is effective to achieve its intended purpose. While individual needs vary, determination of optimal ranges of effective amounts of each component is within the skill of the art. Typically, the compounds may be administered to mammals, e.g. humans, orally at a dose of 0.0025 to 50 mg/kg, or an equivalent amount of the pharmaceutically acceptable salt thereof, per day of the body weight of the mammal being treated for disorders responsive to induction of apoptosis. In one embodiment, about 0.01 to about 25 mg/kg is orally administered to treat, ameliorate, or prevent such disorders. For intramuscular injection, the dose is generally about one-half of the oral dose. For example, a suitable intramuscular dose would be about 0.0025 to about 25 mg/kg, or from about 0.01 to about 5 mg/kg.

The unit oral dose may comprise from about 0.01 to about 1000 mg, for example, about 0.1 to about 100 mg of the compound. The unit dose may be administered one or more times daily as one or more tablets or capsules each containing from about 0.1 to about 10 mg, conveniently about 0.25 to 50 mg of the compound or its solvates.

In a topical formulation, the compound may be present at a concentration of about 0.01 to 100 mg per gram of carrier. In a one embodiment, the compound is present at a concentration of about 0.07-1.0 mg/ml, for example, about 0.1-0.5 mg/ml, and in one embodiment, about 0.4 mg/ml.

In addition to administering the compound as a raw chemical, the compounds of the invention may be administered as part of a pharmaceutical preparation containing suitable pharmaceutically acceptable carriers comprising excipients and auxiliaries which facilitate processing of the compounds into preparations which can be used pharmaceutically. The preparations, particularly those preparations which can be administered orally or topically and which can be used for one type of administration, such as tablets, dragees, slow release lozenges and capsules, mouth rinses and mouth washes, gels, liquid suspensions, hair rinses, hair gels, shampoos and also preparations which can be administered rectally, such as suppositories, as well as suitable solutions for administration by intravenous infusion, injection, topically or orally, contain from about 0.01 to 99 percent, in one embodiment from about 0.25 to 75 percent of active compound(s), together with the excipient.

The pharmaceutical compositions of the invention may be administered to any patient which may experience the beneficial effects of the compounds of the invention. Foremost among such patients are mammals, e.g., humans, although the invention is not intended to be so limited. Other patients include veterinary animals (cows, sheep, pigs, horses, dogs, cats and the like).

The compounds and pharmaceutical compositions thereof may be administered by any means that achieve their intended purpose. For example, administration may be by parenteral, subcutaneous, intravenous, intramuscular, intraperitoneal, transdermal, buccal, intrathecal, intracranial, intranasal or topical routes. Alternatively, or concurrently, administration may be by the oral route. The dosage administered will be dependent upon the age, health, and weight of the recipient, kind of concurrent treatment, if any, frequency of treatment, and the nature of the effect desired.

The pharmaceutical preparations of the present invention are manufactured in a manner which is itself known, for example, by means of conventional mixing, granulating, dragee-making, dissolving, or lyophilizing processes. Thus, pharmaceutical preparations for oral use can be obtained by combining the active compounds with solid excipients, optionally grinding the resulting mixture and processing the mixture of granules, after adding suitable auxiliaries, if desired or necessary, to obtain tablets or dragee cores.

Suitable excipients are, in particular, fillers such as saccharides, for example lactose or sucrose, mannitol or sorbitol, cellulose preparations and/or calcium phosphates, for example tricalcium phosphate or calcium hydrogen phosphate, as well as binders such as starch paste, using, for example, maize starch, wheat starch, rice starch, potato starch, gelatin, tragacanth, methyl cellulose, hydroxypropylmethylcellulose, sodium carboxymethylcellulose, and/or polyvinyl pyrrolidone. If desired, disintegrating agents may be added such as the above-mentioned starches and also carboxymethyl-starch, cross-linked polyvinyl pyrrolidone, agar, or alginic acid or a salt thereof, such as sodium alginate. Auxiliaries are, above all, flow-regulating agents and lubricants, for example, silica, talc, stearic acid or salts thereof, such as magnesium stearate or calcium stearate, and/or polyethylene glycol. Dragee cores are provided with suitable coatings which, if desired, are resistant to gastric juices. For this purpose, concentrated saccharide solutions may be used, which may optionally contain gum arabic, talc, polyvinyl pyrrolidone, polyethylene glycol and/or titanium dioxide, lacquer solutions and suitable organic solvents or solvent mixtures. In order to produce coatings resistant to gastric juices, solutions of suitable cellulose preparations such as acetylcellulose phthalate or hydroxypropylmethylcellulose phthalate, are used. Dye stuffs or pigments may be added to the tablets or dragee coatings, for example, for identification or in order to characterize combinations of active compound doses.

Other pharmaceutical preparations which can be used orally include push-fit capsules made of gelatin, as well as soft, sealed capsules made of gelatin and a plasticizer such as glycerol or sorbitol. The push-fit capsules can contain the active compounds in the form of granules which may be mixed with fillers such as lactose, binders such as starches, and/or lubricants such as talc or magnesium stearate and, optionally, stabilizers. In soft capsules, the active compounds are in one embodiment dissolved or suspended in suitable liquids, such as fatty oils, or liquid paraffin. In addition, stabilizers may be added.

Possible pharmaceutical preparations which can be used rectally include, for example, suppositories, which consist of a combination of one or more of the active compounds with a suppository base. Suitable suppository bases are, for example, natural or synthetic triglycerides, or paraffin hydrocarbons. In addition, it is also possible to use gelatin rectal capsules which consist of a combination of the active compounds with a base. Possible base materials include, for example, liquid triglycerides, polyethylene glycols, or paraffin hydrocarbons.

Suitable formulations for parenteral administration include aqueous solutions of the active compounds in water-soluble form, for example, water-soluble salts and alkaline solutions. In addition, suspensions of the active compounds as appropriate oily injection suspensions may be administered. Suitable lipophilic solvents or vehicles include fatty oils, for example, sesame oil, or synthetic fatty acid esters, for example, ethyl oleate or triglycerides or polyethylene glycol-400. Aqueous injection suspensions may contain substances which increase the viscosity of the suspension include, for example, sodium carboxymethyl cellulose, sorbitol, and/or dextran. Optionally, the suspension may also contain stabilizers.

The topical compositions of this invention are formulated in one embodiment as oils, creams, lotions, ointments and the like by choice of appropriate carriers. Suitable carriers include vegetable or mineral oils, white petrolatum (white soft paraffin), branched chain fats or oils, animal fats and high molecular weight alcohol (greater than $C_{12}$). The carriers may be those in which the active ingredient is soluble. Emulsifiers, stabilizers, humectants and antioxidants may also be included as well as agents imparting color or fragrance, if desired. Additionally, transdermal penetration enhancers can be employed in these topical formulations. Examples of such enhancers can be found in U.S. Pat. Nos. 3,989,816 and 4,444,762; each herein incorporated by reference in its entirety.

Ointments may be formulated by mixing a solution of the active ingredient in a vegetable oil such as almond oil with warm soft paraffin and allowing the mixture to cool. A typical example of such an ointment is one which includes about 30% almond oil and about 70% white soft paraffin by weight. Lotions may be conveniently prepared by dissolving the active ingredient, in a suitable high molecular weight alcohol such as propylene glycol or polyethylene glycol.

One of ordinary skill in the art will readily recognize that the foregoing represents merely a detailed description of certain preferred embodiments of the present invention. Various modifications and alterations of the compositions and methods described above can readily be achieved using expertise available in the art and are within the scope of the invention.

EXAMPLES

The following examples are illustrative, but not limiting, of the compounds, compositions, and methods of the present invention. Other suitable modifications and adaptations of the variety of conditions and parameters normally encountered in clinical therapy and which are obvious to those skilled in the art are within the spirit and scope of the invention.

Example I

Experiments conducted during the course of developing embodiments for the present invention involved performance of a phenotypic screen of a library of 20,000 small-molecules representing five million compounds. QN519 was identified as a promising hit compound for further analysis based on its novelty, drug-like properties, and in vitro activity profile in a panel of 10 cancer cell lines. Subsequently, a lead optimization campaign was performed to synthesize a series of close analogs. Initially, the 50 analogs were tested in three pancreatic cancer cell lines using MTT assay (Table 1). Sixteen compounds produced $IC_{50}$ values <1 µM in at least one cell line.

TABLE 1

IC50 values of QN compounds in pancreatic cancer cell lines.

| Code | Compound Structure | M.W. | IC50 Values (04) [1] | | |
|---|---|---|---|---|---|
| | | | MiaPaCa-2 | Panc-1 | BxPC-3 |
| Gemcitabine | | | 0.11 ± 0.07 | 0.20 ± 0.10 | 0.05 ± 0.02 |
| *[2] QN519 | 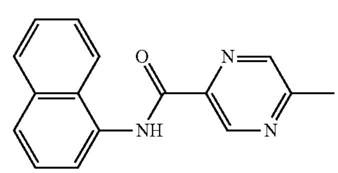 [SMILES: Cc1cnc(C(=O)Nc2cccc3ccccc23)cn1] | 264.28 | 0.50 ± 0.18 | 1.80 ± 0.35 | 9.40 ± 0.51 |
| QN520 | 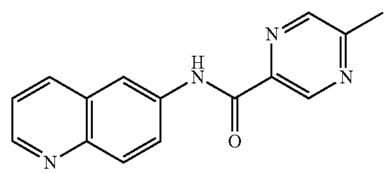 [SMILES: Cc1cnc(C(=O)Nc2ccc3ncccc3c2)cn1] | 264.28 | >10 | >10 | >10 |

TABLE 1-continued

IC50 values of QN compounds in pancreatic cancer cell lines.

| | | | | IC50 Values (04) [1] | |
|---|---|---|---|---|---|
| Code | Compound Structure | M.W. | MiaPaCa-2 | Panc-1 | BxPC-3 |
| QN521 | | 264.28 | >10 | >10 | >10 |
| QN522 | | 263.29 | >10 | >10 | >10 |
| * QN523 | | 250.26 | 0.11 ± 0.03 | 0.50 ± 0.07 | 3.30 ± 0.26 |
| QN524 | | 328.16 | >10 | >10 | >10 |
| QN529 | | 328.16 | 1.83 ± 0.72 | 4.00 ± 0.80 | >10 |
| QN530 | | 328.16 | >10 | >10 | >10 |
| QN532 | | 267.26 | >10 | >10 | >10 |
| QN566 | | 250.26 | 8.50 ± 1.03 | >10 | >10 |

TABLE 1-continued

IC50 values of QN compounds in pancreatic cancer cell lines.

| Code | Compound Structure | M.W. | IC50 Values (04) [1] | | |
|---|---|---|---|---|---|
| | | | MiaPaCa-2 | Panc-1 | BxPC-3 |
| * QN567 | | 250.26 | 0.33 ± 0.06 | >10 | >10 |
| QN571 | | 343.19 | 2.23 ± 0.31 | 6.83 ± 1.73 | >10 |
| QN572 | | 300.31 | >10 | >10 | >10 |
| QN573 | | 284.70 | 7.00 ± 1.30 | 9.30 ± 0.80 | >10 |
| QN608 | | 379.21 | >10 | >10 | >10 |
| QN609 | | 331.32 | >10 | >10 | >10 |
| QN610 | | 389.40 | >10 | >10 | >10 |

TABLE 1-continued

IC50 values of QN compounds in pancreatic cancer cell lines.

| Code | Compound Structure | M.W. | IC50 Values (04) [1] | | |
|---|---|---|---|---|---|
| | | | MiaPaCa-2 | Panc-1 | BxPC-3 |
| * QN618 | | 329.15 | 0.75 ± 0.09 | 7.02 ± 2.92 | 7.51 ± 1.32 |
| QN632 | | 278.31 | >10 | >10 | >10 |
| QN634 | | 264.28 | >10 | >10 | >10 |
| * QN651 | | 268.24 | 0.13 ± 0.06 | 0.67 ± 0.25 | >10 |
| * QN652 | | 282.27 | 0.31 ± 0.16 | 2.12 ± 0.94 | >10 |
| QN655 | | 251.24 | 7.70 ± 1.53 | 6.72 ± 1.02 | 7.22 ± 1.02 |

TABLE 1-continued

IC50 values of QN compounds in pancreatic cancer cell lines.

| | | | IC50 Values (04) [1] | | |
|---|---|---|---|---|---|
| Code | Compound Structure | M.W. | MiaPaCa-2 | Panc-1 | BxPC-3 |
| * QN658 | | 268.24 | 0.30 ± 0.10 | 5.33 ± 1.53 | >10 |
| QN659 | | 307.35 | >10 | >10 | >10 |
| QN660 | | 264.26 | >10 | >10 | >10 |
| * QN663 | | 294.31 | 0.27 ± 0.15 | 0.83 ± 0.21 | 6.70 ± 0.60 |
| QN792 | | 284.70 | 2.83 ± 0.76 | 2.70 ± 0.52 | >10 |
| QN793 | | 298.73 | 1.50 ± 0.50 | 1.77 ± 0.25 | 5.2 ± 0.3 |

TABLE 1-continued

IC50 values of QN compounds in pancreatic cancer cell lines.

| Code | Compound Structure | M.W. | IC50 Values (04) [1] | | |
| --- | --- | --- | --- | --- | --- |
| | | | MiaPaCa-2 | Panc-1 | BxPC-3 |
| * QN794 | | 284.70 | 0.80 ± 0.05 | 4.67 ± 1.53 | >10 |
| * QN107 | | 280.28 | 0.28 ± 0.04 | 0.77 ± 0.21 | 5.53 ± 1.18 |
| QN113 | | 280.28 | 1.30 ± 0.35 | 9.00 ± 1.41 | >10 |
| QN137 | | 379.41 | 1.70 ± 0.52 | 8.17 ± 1.61 | 5.17 ± 1.61 |
| * QN138 | | 393.43 | 0.73 ± 0.15 | 3.50 ± 0.50 | 2.00 ± 0.87 |

TABLE 1-continued

IC50 values of QN compounds in pancreatic cancer cell lines.

| Code | Compound Structure | M.W. | IC50 Values (04) [1] | | |
|---|---|---|---|---|---|
| | | | MiaPaCa-2 | Panc-1 | BxPC-3 |
| QN142 | | 266.25 | >10 | >10 | >10 |
| * QN144 | | 312.29 | 0.37 ± 0.15 | 0.53 ± 0.21 | 4.33 ± 0.76 |
| QN147 | | 337.37 | >10 | >10 | >10 |
| QN148 | | 351.40 | 1.80 ± 0.46 | 4.50 ± 0.50 | 9.67 ± 0.58 |

TABLE 1-continued

IC50 values of QN compounds in pancreatic cancer cell lines.

| Code | Compound Structure | M.W. | IC50 Values (04) [1] | | |
|---|---|---|---|---|---|
| | | | MiaPaCa-2 | Panc-1 | BxPC-3 |
| * QN151 | | 409.17 | 0.87 ± 0.15 | 9.50 ± 0.50 | 9.17 ± 0.76 |
| * QN152 | | 423.19 | 0.67 ± 0.12 | 2.17 ± 0.76 | 3.67 ± 0.76 |
| QN153 | | 409.17 | >10 | >10 | >10 |
| QN154 | | 309.12 | >10 | >10 | >10 |

TABLE 1-continued

IC50 values of QN compounds in pancreatic cancer cell lines.

| Code | Compound Structure | M.W. | IC50 Values (04) [1] | | |
| --- | --- | --- | --- | --- | --- |
| | | | MiaPaCa-2 | Panc-1 | BxPC-3 |
| QN156 | | 323.13 | >10 | >10 | >10 |
| QN159 | | 477.23 | 3.67 ± 1.15 | 9.50 ± 0.50 | 3.33 ± 0.58 |
| QN160 | | 491.25 | 9.00 ± 1.73 | 9.67 ± 0.58 | 9.33 ± 1.15 |

TABLE 1-continued

IC50 values of QN compounds in pancreatic cancer cell lines.

| Code | Compound Structure | M.W. | IC50 Values (04) [1] | | |
| --- | --- | --- | --- | --- | --- |
| | | | MiaPaCa-2 | Panc-1 | BxPC-3 |
| QN161 | 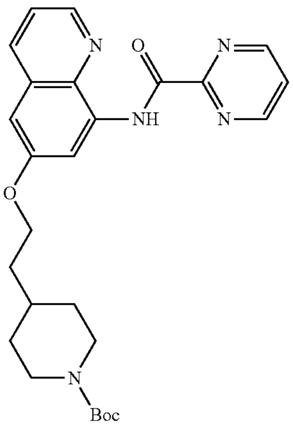 [SMILES: CC(C)(C)OC(=O)N1CCC(CCOc2cc(NC(=O)c3ncccn3)c3ncccc3c2)CC1] | 477.23 | >10 | >10 | >10 |
| QN162 | 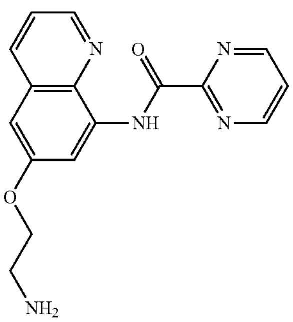 [SMILES: NCCOc1cc(NC(=O)c2ncccn2)c2ncccc2c1] | 309.12 | >10 | >10 | >10 |
| QN163 | 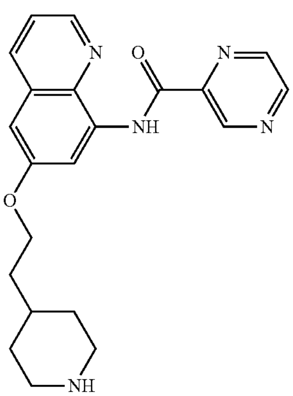 [SMILES: O=C(Nc1cc(OCCC2CCNCC2)cc2cccnc12)c1cnccn1] | 377.18 | >10 | >10 | >10 |
| QN164 | 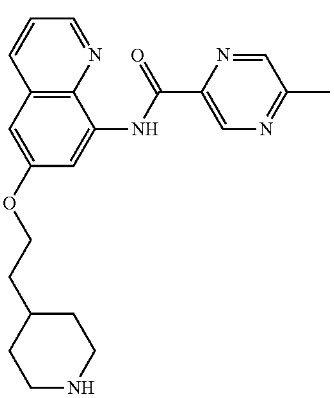 [SMILES: Cc1cnc(C(=O)Nc2cc(OCCC3CCNCC3)cc3cccnc23)cn1] | 391.20 | 6.17 ± 1.04 | >10 | 8.33 ± 1.53 |

TABLE 1-continued

IC50 values of QN compounds in pancreatic cancer cell lines.

| Code | Compound Structure | M.W. | IC50 Values (04) [1] | | |
|------|-------------------|------|----------|--------|--------|
| | | | MiaPaCa-2 | Panc-1 | BxPC-3 |
| QN165 | 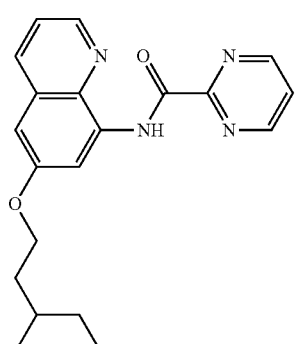 | 377.18 | >10 | >10 | >10 |

[1] Values are represented as Mean ± SD from three independent MTT assay experiments.
[2] Marks for compounds with $IC_{50}$ lower than 1 μM in at least one cell line.

The 6-substituted 3-methyl-pyrazine was found to be important for cytotoxicity of QN519. Changing the 3-methyl-pyrazine group to substituted pyridine (QN522, 524, 532) substantially decreased its cytotoxicity. Removing the methyl group at 3 position of pyrazine resulted in a potent compound QN523, implicating that the additional methyl group is not necessary for compound-target interaction. Changing the heterocyclic group to pyridazine (QN566) largely decreased the activity, while changing to pyrimidine (QN567) only slightly affected the cytotoxicity when the substitution remains on the 6 position of the ring.

The 8-substituted quinoline was also necessary for the activity of QN519. Substitutions on the 5 or 6 position (QN520, 521) of the quinoline decreased activity of the lead compound. Additional side chain on the 2 position of the quinoline also led to loss of activity (QN632, 634, 659, 660). Fluorine (QN651, 652 and 658) or methoxy (QN663, QN107, QN113) substitution on the 6 position improved the activity modestly, suggesting this position as sight for potential modification.

In an effort to investigate this potential modification site, a series of compounds with longer side chains were designed to 1) improve solubility and 2) increase specificity through additional binding sites. Select compound from this round of optimization was intended for linkage with fluorescent or biotin probe for target identification in vitro using biochemistry methods. However, the 18 compounds with different linker side chains do not retain similar cytotoxicity. No further chemical modification was attempted in this series.

Example II

This Example Demonstrates that QN523 Shows Significant Cytotoxicity in Pancreatic Cancer Cell Lines.

In the lead optimization campaign, QN523 was identified as the most potent compound in the series with $IC_{50}$ value of 0.11 μM in MiaPaCa-2 cells, which is comparable to gemcitabine, the current standard of care therapy for pancreatic cancer.

In order to understand its potential selectivity for different types of cancer and choose the best model for further characterization, QN523 was tested in a panel of 12 cancer cell lines with various genetic and pathological backgrounds (Table 2). QN523 showed significant cytotoxicity with $IC_{50}$ values ranging from 0.1 to 5.7 μM across all 12 cell lines. QN523 was potent in the pancreatic cancer cell line MiaPaCa-2, leukemia cell line Jurkat and colorectal cancer cell line HCT116, with $IC_{50}$ value around 0.1 μM. Because of remarkable potency of QN-523 in pancreatic cancer in-depth preclinical studies in this disease model were performed.

TABLE 2

$IC_{50}$ values of QN523 in a panel of cancer cell lines.

| | PDAC cell lines | | | HCC cell lines | | | | | | Other cancer cell lines | |
|---|---|---|---|---|---|---|---|---|---|---|---|
| | Mia PaCa-2 | Panc-1 | BxPC-3 | HepG2 | Hep3B | SNU398 | SNU387 | SNU449 | SNU475 | Ovcar 8 | Jurkat | HCT116 p53+/+ |
| QN523 | 0.11 ± 0.03 | 0.50 ± 0.07 | 3.30 ± 0.26 | 0.50 ± 0.10 | 0.21 ± 0.09 | 1.90 ± 0.60 | 5.73 ± 0.46 | 0.40 ± 0.15 | 2.67 ± 0.84 | 0.30± 0.12 | 0.10 ± 0.04 | 0.10 ± 0.03 |

[1] Values are represented as Mean ± SD from three independent MTT assay experiments.

Example III

This example demonstrates that QN523 is cytotoxic in pancreatic cancer cell lines. The cytotoxicity of QN523 was further evaluated in three pancreatic cancer cell lines using colony formation assay. Using numbers and sizes of colonies as the experimental readout, this long-term assay estimates both anti-proliferative and cytotoxic effect. QN523 showed more potent activity in colony formation assay than in MTT assay (FIG. 1A). Complete inhibition of colony formation was observed in all three cell lines at 1 µM. At 0.1 µM QN523 treatment, a complete suppression of MiaPaCa-2 colonies was observed, suggesting further evaluation is warranted.

To test the durability of treatment, MiaPaCa-2 cells were treated with QN523 for 1, 4, 8, 24, 48, 72 h, washed with PBS, and assayed 72 hrs later. A time dependent cytotoxicity effect was observed for QN523 treatment (FIG. 1A) suggesting a delayed onset for activity.

Example IV

This example demonstrates that QN523 exhibits anti-cancer activity in in vivo pancreatic cancer xenograft model. To further evaluate the therapeutic potentials of QN523 in pancreatic cancer, MiaPaCa-2 xenograft were implanted in NOD/SCID mice. When tumor size reached 100 mm$^3$, mice were randomized to either vehicle control (n=5) or QN523 treatment (n=5) group. QN523 was initially given at 10 mg/kg with intraperitoneal administration. Since no significant delay in tumor growth was observed in the QN523 treatment group from day 1 to day 9, dose of QN523 was increased to 20 mg/kg from day 10 and continued until day 44.

Figure 2:
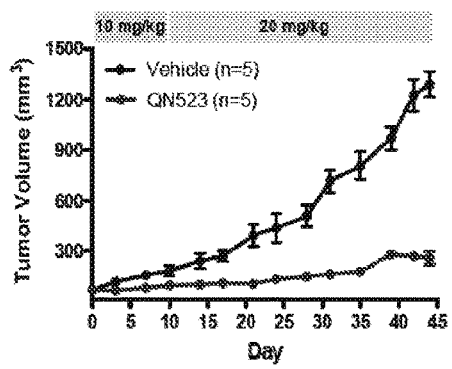
FIG. 2A-E: QN523 inhibits tumor growth of MiaPaCa-2 xenograft without systemic cytotoxicity. A) Tumor volume of MiaPaCa-2 xenograft of vehicle or QN523 treated mice. MiaPaCa-2 xenograft was established in NOD/SCID mice. When tumor size reached 100 mm$^3$, mice were randomized into vehicle control group (n=5) or treatment group (n=5). QN523 was given by i.p. injection five times a week at 10 mg/kg from day 1 to day 9, then at 20 mg/kg from day 10 to day 44. B) Body weight of vehicle of QN523 treated mice. Representative micrographs of hematoxylin and eosin (H&E)-stained organ sections. Images were taken with Olympus IX83 inverted microscope at 20× magnification. In histopathology study, no major microscopic changes were detected in major organs after QN523 treatment. C) H&E stained organ sections of liver, kidney, heart, lung, spleen and pancreas did not reveal major histopathological changes, further confirming the safety of the treatment. D) Tumor volumes of study continued after data shown in panel A. QN523 was given at 20 mg/kg five times a week until day 44. Three mice from each group were euthanized for tissue analysis. Two mice remained in each group after day 44 and QN523 dose was increased to 30 mg/kg from day 45, then to 40 mg/kg from day 51 to day 60. E) Body weight of engrafted mice was not affected by QN523 treatment at 10-40 mg/kg. Error bars indicate Mean±SEM.
Figure 2:
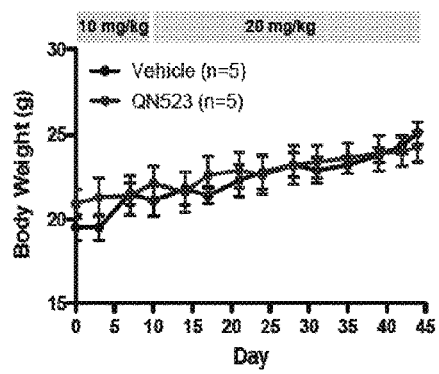
Figure 2:
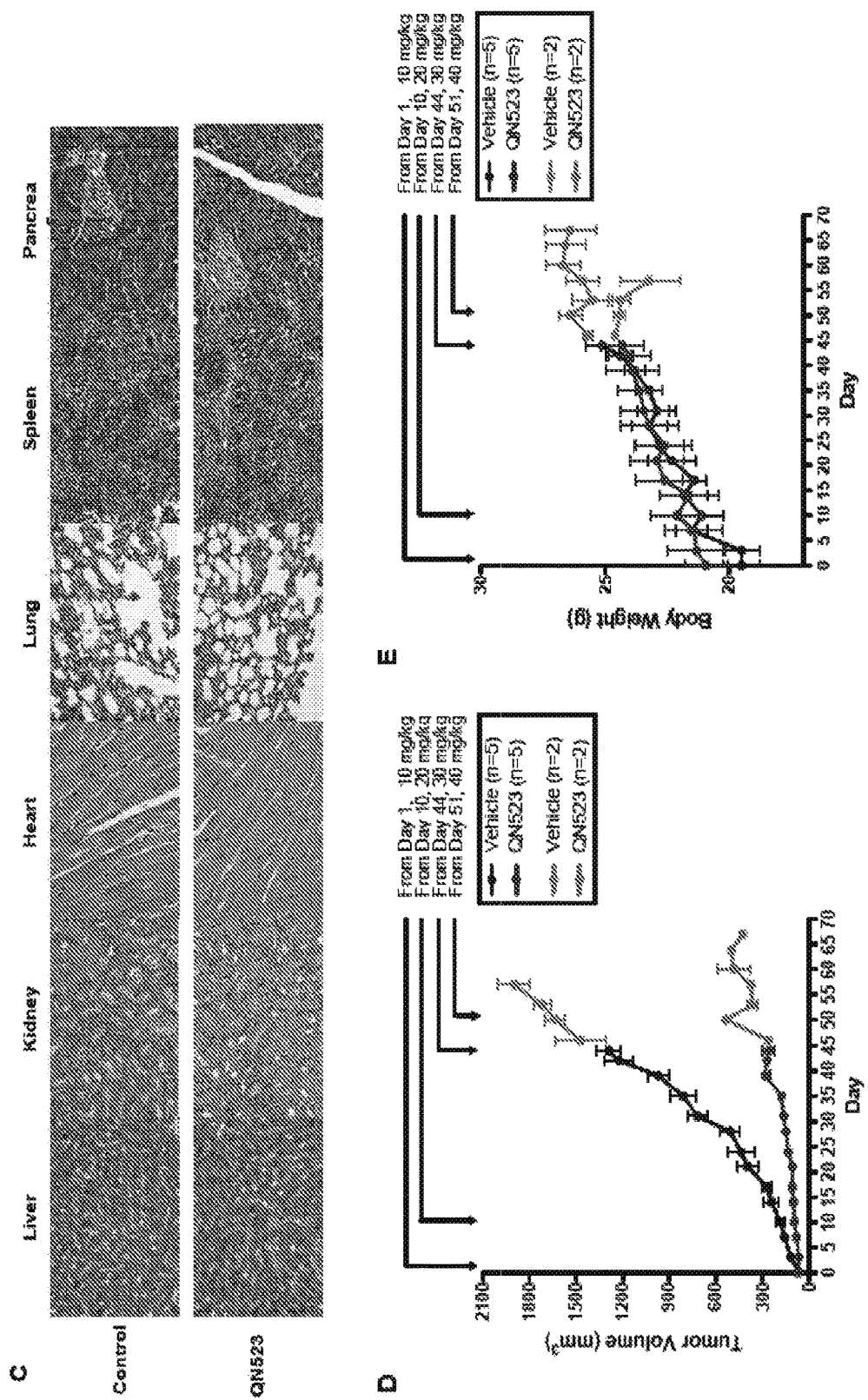
Figure 3:
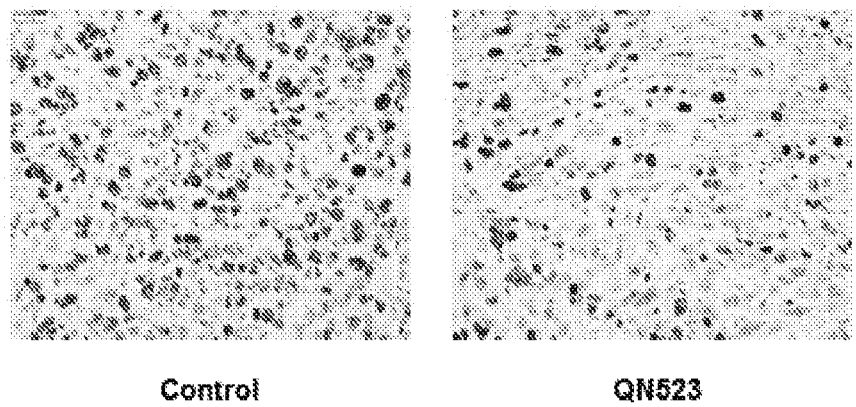
FIG. 3A-B: QN523 inhibits tumor cell proliferation in MiaPaCa-2 xenograft. A) Representative immunohistochemistry images for Ki67 staining of MiaPaCa-2 xenograft sections. B) QN523 decreased Ki67 index (percentage of Ki67 positive cells in the field) of treated tumors. Quantification of Ki67 positive cells were performed with image J on three fields of each sample, three samples were tested for each treatment group. Data represents Mean±SD. P values were calculated using student's t-test, **** indicates p<0.0001.
Figure 3:
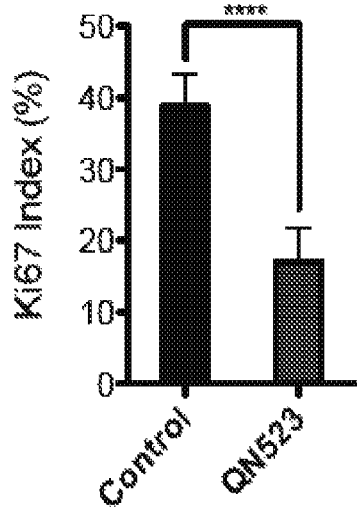

QN523 treatment delayed growth of the MiaPaCa-2 xenograft starting from day 17 ($p<0.01$). On day 44, when mean tumor volume of the vehicle control group reached 1291±72 mm$^3$, mean tumor volume of the QN523 treatment group was only 259±38 mm$^3$ ($p<0.0001$) indicating 80% inhibition of tumor growth (FIG. 2A). No symptoms of gross toxicity such as weakness, weight loss or lethargy were observed in the QN523 treatment group (FIG. 2B). H&E stained organ sections of liver, kidney, heart, lung, spleen and pancreas did not reveal major histopathological changes, further confirming the safety of the treatment (FIG. 2C). Following the 44-day treatment, two mice were kept on each group to evaluate efficacy and safety of QN523 at higher doses. While tumors in the control group exhibited rapid growth, QN523 treatment was able to delay growth of the tumors, and no systemic toxicity was observed at doses as high as 40 mg/kg (FIGS. 2D&E). In line with the tumor growth inhibition, QN523 treatment decreased Ki67 levels in tumor tissues, suggesting inhibition of cell proliferation (FIG. 3). Taken together, in vivo studies in MiaPaCa-2 xenograft model suggests promising anti-cancer activity and safety profile of QN523, supporting further characterization of the compound as drug candidate for the treatment of pancreatic cancer.

Example V

This example demonstrates that Bru-seq analysis identified stress signaling and autophagy as major cellular responses to treatment with QN523. In order to understand the mechanism of action for QN523 in pancreatic cancer, Bru-seq was performed to evaluate global changes in gene synthesis after QN523 treatment. Preliminary observations suggest that QN series of compounds require a minimum of 24 hours to exert significant pharmacological effects. During this time, the cells begin initiating cascade of pharmacological events unique to these compounds. However, cell death pathways will be initiated at later time points well beyond 24 hrs. Therefore, the Bru-seq experiments were performed after 24 hrs drug (1 µM) exposure. Using RPKM>0.5, gene size >300 bp as the cut off values to eliminate background noises, there were totally 8521 expressed genes in the QN523 and DMSO control samples out of around 22,000 genes in the reference genome. 275 genes were significantly unregulated more than two fold with QN523, and 123 genes were downregulated by the treatment.

Example VI

Figure 4:
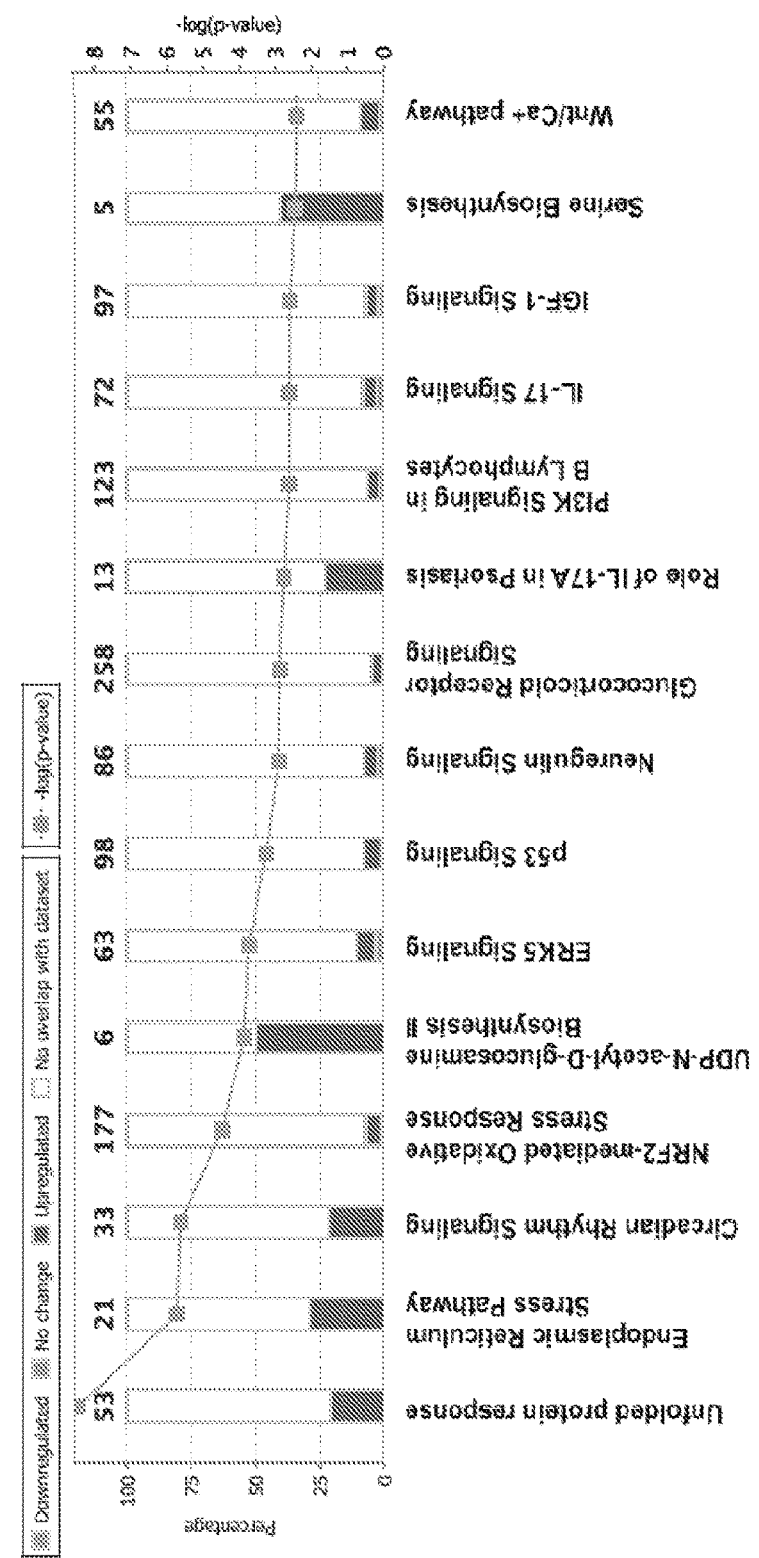
FIG. 4: QN523 induces stress responses in MiaPaCa-2 cells as revealed by Ingenuity Pathway Analysis. Top 20 canonical pathways regulated by QN523. Histogram represents percentage of genes regulated in the pathway; numbers on the histogram are total numbers of genes in the specific pathway. Red color stands for up-regulated genes, and green color stands for down-regulated genes. Orange line represents statistical significance in regulation of the indicated pathway.

The example demonstrates that IPA and DAVID analysis revealed QN523-induced stress responses in MiaPaCa-2. For general understanding of cellular functions and pathways regulated by QN523 treatment, the up and downregulated gene lists were analyzed by Ingenuity Pathway Analysis (IPA). Induction of unfolded protein response, ER stress pathway and circadian rhythm signaling were most significant with QN523 treatment, where about 25% of genes in these pathways were up-regulated, suggesting activation of stress signaling in MiaPaCa-2 cells (FIG. 4).

Figure 5:
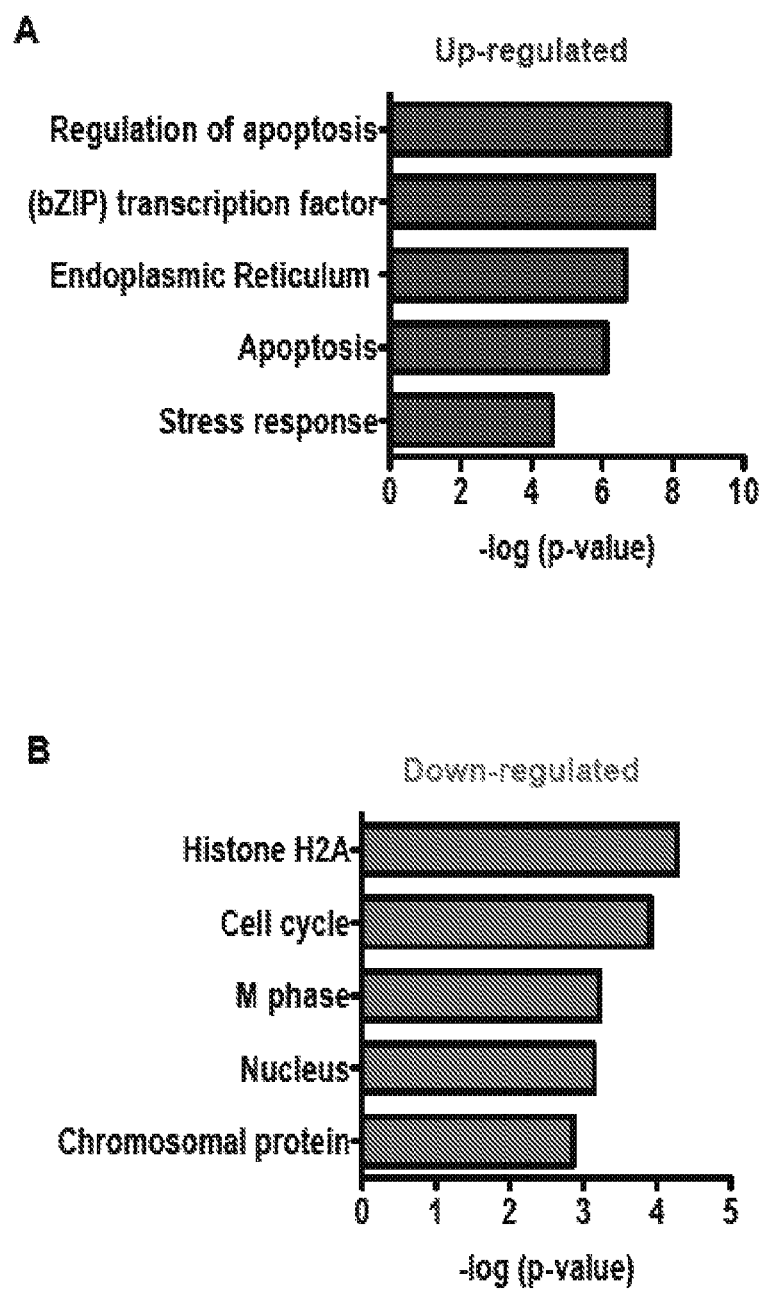
FIG. 5A-B: QN523 induces apoptosis and stress responses in MiaPaCa-2 cells as revealed DAVID analysis. A) Top 5 biological themes in genes upregulated by QN523 treatment. B) Top 5 biological themes in genes downregulated by QN523 treatment. Histogram represents statistical significance in regulation of the indicated theme.

The lists were also analyzed by Database for Annotation, Visualization and Integrated Discovery (DAVID), which identify enriched biological themes with particular focus on gene ontology terms, as well as functional-related gene groups (see, e.g., Huang da W, Sherman B T, Lempicki R A (2009) Nature protocols 4(1): 44-57; Huang da W, Sherman B T, Lempicki R A (2009) Nucleic acids research 37(1): 1-13). Apoptosis, (bZIP) transcription factors, ER related genes and stress responses were unregulated by QN523, while chromosomal proteins and cell cycle genes were downregulated by the treatment (FIG. 5). These results again suggest activation of stress responses by QN523 as shown with IPA analysis. In addition, induction of apoptosis and disruption of cell cycle might be important cellular events contributing to cytotoxicity of QN523.

Example VII

This example demonstrates that GSEA suggested inverse correlation with estradiol-regulated transcription. Gene Set Enrichment Analysis (GSEA) was also applied to the pre-ranked list of all expressed genes to discover gene sets potentially affected by QN523 treatment, and identified a list of gene sets enriched in the top or bottom of the pre-ranked list, suggesting correlation of these functional groups of genes with QN523 treatment. The top 20 up or downregulated gene sets are listed in Tables 3 and 4.

TABLE 3

Top 20 gene sets upregulated with QN523 treatment

| | NAME | SIZE | NES | FDR q-val |
|---|---|---|---|---|
| 1 | PODAR_RESPONSE_TO_ADAPHOSTIN_UP | 104 | 3.0437453 | <10E−6 |
| 2 | TIEN_INTESTINE_PROBIOTICS_24HR_DN | 183 | 2.8273673 | <10E−6 |
| 3 | BLUM_RESPONSE_TO_SALIRASIB_UP | 204 | 2.774138 | <10E−6 |
| 4 | HELLER_SILENCED_BY_METHYLATION_DN | 58 | 2.770397 | <10E−6 |
| 5 | ZHANG_RESPONSE_TO_IKK_INHIBITOR_AND_TNF_UP | 112 | 2.7220533 | <10E−6 |
| 6 | NAGASHIMA_NRG1_SIGNALING_UP | 116 | 2.7184274 | <10E−6 |
| 7 | BOQUEST_STEM_CELL_CULTURED_VS_FRESH_UP | 159 | 2.6981082 | <10E−6 |
| 8 | DUTERTRE_ESTRADIOL_RESPONSE_24HR_DN | 244 | 2.6971843 | <10E−6 |
| 9 | BILD_HRAS_ONCOGENIC_SIGNATURE | 142 | 2.6907232 | <10E−6 |
| 10 | KRIGE_RESPONSE_TO_TOSEDOSTAT_24HR_UP | 472 | 2.6795332 | <10E−6 |
| 11 | GROSS_HYPOXIA_VIA_ELK3_DN | 102 | 2.6527967 | <10E−6 |
| 12 | ONDER_CDH1_TARGETS_1_UP | 66 | 2.6429064 | <10E−6 |
| 13 | GARGALOVIC_RESPONSE_TO_OXIDIZED_PHOSPHOLIPIDS_BLUE_UP | 107 | 2.640958 | <10E−6 |
| 14 | PICCALUGA_ANGIOIMMUNOBLASTIC_LYMPHOMA_DN | 102 | 2.6376972 | <10E−6 |
| 15 | KAN_RESPONSE_TO_ARSENIC_TRIOXIDE | 66 | 2.624026 | <10E−6 |
| 16 | ADDYA_ERYTHROID_DIFFERENTIATION_BY_HEMIN | 45 | 2.602759 | <10E−6 |
| 17 | CONCANNON_APOPTOSIS_BY_EPOXOMICIN_UP | 149 | 2.5632482 | <10E−6 |
| 18 | ELVIDGE_HYPOXIA_BY_DMOG_UP | 67 | 2.5623298 | <10E−6 |
| 19 | ELVIDGE_HYPOXIA_UP | 88 | 2.5620668 | <10E−6 |
| 20 | GARGALOVIC_RESPONSE_TO_OXIDIZED_PHOSPHOLIPIDS_TURQUOISE_UP | 65 | 2.5583937 | <10E−6 |

TABLE 4

Top 20 gene sets downregulated with QN523 treatment

| | NAME | SIZE | NES | FDR q-val |
|---|---|---|---|---|
| 1 | ROSTY_CERVICAL_CANCER_PROLIFERATION_CLUSTER | 128 | −2.8185263 | <10E−6 |
| 2 | GARGALOVIC_RESPONSE_TO_OXIDIZED_PHOSPHOLIPIDS_TURQUOISE_DN | 44 | −2.6491916 | <10E−6 |
| 3 | ZHAN_MULTIPLE_MYELOMA_PR_UP | 42 | −2.5831153 | <10E−6 |
| 4 | AMUNDSON_GAMMA_RADIATION_RESPONSE | 37 | −2.5632613 | <10E−6 |
| 5 | BURTON_ADIPOGENESIS_PEAK_AT_24HR | 35 | −2.5429745 | <10E−6 |
| 6 | LEE_EARLY_T_LYMPHOCYTE_UP | 78 | −2.5337672 | <10E−6 |
| 7 | CROONQUIST_IL6_DEPRIVATION_DN | 86 | −2.531633 | <10E−6 |
| 8 | DUTERTRE_ESTRADIOL_RESPONSE_24HR_UP | 257 | −2.5003061 | <10E−6 |
| 9 | CROONQUIST_NRAS_SIGNALING_DN | 65 | −2.4969666 | <10E−6 |
| 10 | WHITEFORD_PEDIATRIC_CANCER_MARKERS | 101 | −2.4715047 | <10E−6 |
| 11 | ISHIDA_E2F_TARGETS | 50 | −2.4621954 | <10E−6 |
| 12 | MORI_LARGE_PRE_BII_LYMPHOCYTE_UP | 78 | −2.457367 | <10E−6 |
| 13 | GRAHAM_CML_DIVIDING_VS_NORMAL_QUIESCENT_UP | 140 | −2.4507458 | <10E−6 |
| 14 | KANG_DOXORUBICIN_RESISTANCE_UP | 51 | −2.4243076 | <10E−6 |
| 15 | SOTIRIOU_BREAST_CANCER_GRADE_1_VS_3_UP | 148 | −2.4237332 | <10E−6 |
| 16 | ZHOU_CELL_CYCLE_GENES_IN_IR_RESPONSE_6HR | 80 | −2.3799622 | <10E−6 |
| 17 | BLUM_RESPONSE_TO_SALIRASIB_DN | 276 | −2.3799057 | <10E−6 |
| 18 | ZHOU_CELL_CYCLE_GENES_IN_IR_RESPONSE_24HR | 113 | −2.3664784 | <10E−6 |
| 19 | PID_PLK1_PATHWAY | 43 | −2.3617427 | <10E−6 |
| 20 | GOBERT_OLIGODENDROCYTE_DIFFERENTIATION_UP | 463 | −2.3504372 | <10E−6 |

Except for the frequently enriched large gene sets associated with adaphostin, salirasib, tosedostat and oxidized phospholipids treatments, which show low specificity and were often found in the analysis with other compounds, there are several highly enriched gene sets that are of particular interests. Induction of apoptosis and inhibition on cell cycle were observed among the enriched gene sets, which are in agreement with the discovery with DAVID analysis. Similar transcription profiles with IKK inhibitor plus TNF treatment, neuregulin (NRG) treatment and hypoxia were observed, suggesting potential involvement or similarity with these treatment-related signaling profiles.

Interestingly, the transcription profile of QN523 in MiaPaCa-2 showed inverse correlation with that of estradiol treatment in MCF7. While the role of estrogen and its receptor is not well characterized in pancreatic cancer, it is a major promoting factor that induces cell proliferation in breast cancer cases. Estrogen-regulated genes identified in breast cancer models contribute to cell motility and cell cycle regulations (see, e.g., Dutertre M, et al., (2010) Cancer research 70(9): 3760-3770). Although the cellular context might be different in breast cancer and pancreatic cancer cells, potential phenotypic simulation of estrogen inhibition by QN523 in pancreatic cancer implies that the anti-proliferative activity of QN523 might involve estrogen-regulated genes. This result also supports evaluation of QN523 in estrogen dependent breast cancer models for validation and further characterization of the compound and putative therapeutic effects.

Example VIII

Figure 6:
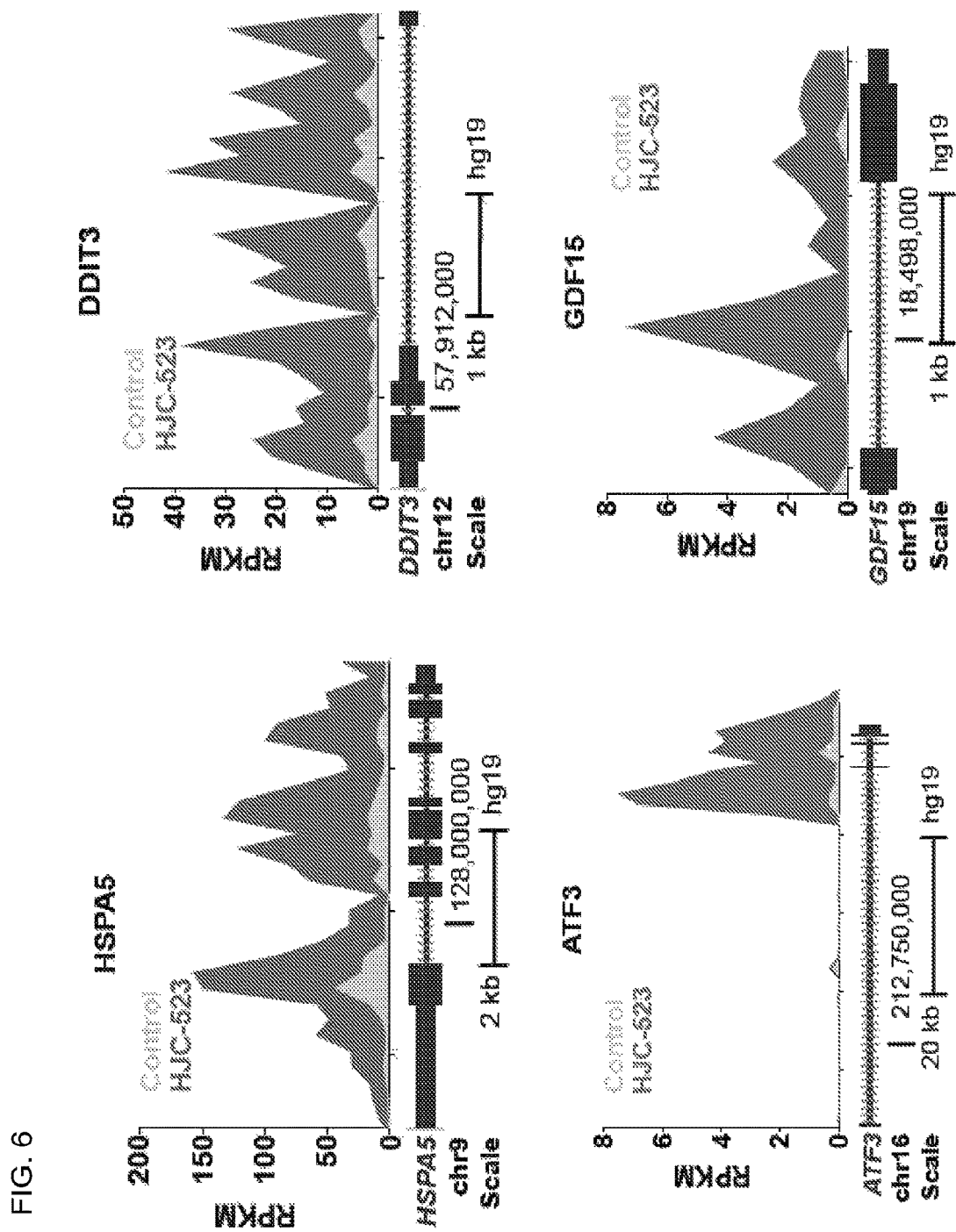
FIG. 6: QN523 induces transcription of stress responsive genes.

The example pertains to the top genes regulated by QN523 treatment. While bioinformatics studies of the differentially expressed gene lists provide information on functional regulation of the QN523 treatment, it is also important to identify cellular responders that correlate with QN523 activity and might contribute to its cytotoxicity. Such selected genes could serve as markers for mechanistic studies in vitro, and as pharmacodynamics markers for future in vivo applications. Robust and significant regulation by the treatment is required for potential biomarkers, so we chose the top genes regulated by QN523 as candidates. The top 20 genes up or downregulated by QN523 are reported here and further studied for their cellular function (Tables 5 and 6).

and thus would serve as robust marker for stress signaling. GDF15 and ATF3 RNA synthesis was highly upregulated by QN523, with >20 fold increase (FIG. 6). Interestingly, these two genes are also found to be stress-related (see, e.g., Hai T, Hartman M G (2001) Gene 273(1): 1-11; Vanhara P, Hampl A, Kozubik A, Soucek K (2012) Prostate cancer and

TABLE 5

Top 20 genes upregulated by QN523 treatment

| Rank | ID | Fold Change | Entrez Gene Name | Location | Type(s) |
|---|---|---|---|---|---|
| 1 | GDF15 | 42.8 | growth differentiation factor 15 | Extracellular Space | growth factor |
| 2 | ATF3 | 22.1 | activating transcription factor 3 | Nucleus | transcription regulator |
| 3 | UPP1 | 18.4 | uridine phosphorylase 1 | Cytoplasm | enzyme |
| 4 | LOC344887 | 16.7 | NmrA-like family domain containing 1 pseudogene | Other | other |
| 5 | FAM129A | 16.0 | family with sequence similarity 129, member A | Cytoplasm | other |
| 6 | WIPI1 | 15.3 | WD repeat domain, phosphoinositide interacting 1 | Cytoplasm | other |
| 7 | TRIB3 | 14.3 | tribbles pseudokinase 3 | Nucleus | kinase |
| 8 | HMOX1 | 13.6 | heme oxygenase (decycling) 1 | Cytoplasm | enzyme |
| 9 | CXCL3 | 11.1 | chemokine (C—X—C motif) ligand 3 | Extracellular Space | cytokine |
| 10 | DDIT3 | 10.7 | DNA-damage-inducible transcript 3 | Nucleus | transcription regulator |
| 11 | SLFN5 | 10.1 | schlafen family member 5 | Nucleus | enzyme |
| 12 | HERPUD1 | 10.0 | homocysteine-inducible, endoplasmic reticulum stress-inducible, ubiquitin-like domain member 1 | Cytoplasm | other |
| 13 | GABARAPL1 | 8.2 | GABA(A) receptor-associated protein like 1 | Cytoplasm | other |
| 14 | OSGIN1 | 8.0 | oxidative stress induced growth inhibitor 1 | Other | growth factor |
| 15 | HSPA5 | 7.9 | heat shock 70 kDa protein 5 (glucose-regulated protein, 78 kDa) | Cytoplasm | enzyme |
| 16 | DNAJB9 | 7.8 | DnaJ (Hsp40) homolog, subfamily B, member 9 | Nucleus | other |
| 17 | SAT1 | 7.2 | spermidine/spermine N1-acetyltransferase 1 | Cytoplasm | enzyme |
| 18 | MAP1LC3B | 6.9 | microtubule-associated protein 1 light chain 3 beta | Cytoplasm | other |
| 19 | CCNG2 | 6.6 | cyclin G2 | Nucleus | other |
| 20 | CD55 | 6.3 | CD55 molecule, decay accelerating factor for complement (Cromer blood group) | Plasma Membrane | other |

TABLE 6

Top 20 genes upregulated by QN523 treatment

| Rank | ID | Fold Change | Entrez Gene Name | Location | Type(s) |
|---|---|---|---|---|---|
| 1 | C17orf62 | −2.5 | chromosome 17 open reading frame 62 | Other | other |
| 2 | C9orf140 | −2.5 | suppressor APC domain containing 2 | Nucleus | other |
| 3 | THAP11 | −2.5 | THAP domain containing 11 | Nucleus | other |
| 4 | NAT14 | −2.4 | N-acetyltransferase 14 (GCN5-related, putative) | Extracellular Space | other |
| 5 | FASN | −2.4 | fatty acid synthase | Cytoplasm | enzyme |
| 6 | SEMA6B | −2.4 | sema domain, transmembrane domain (TM), and cytoplasmic domain, (semaphorin) 6B | Plasma Membrane | other |
| 7 | CCDC85C | −2.4 | coiled-coil domain containing 85C | Plasma Membrane | other |
| 8 | HPDL | −2.4 | 4-hydroxyphenylpyruvate dioxygenase-like | Other | other |
| 9 | ZDHHC12 | −2.4 | zinc finger, DHHC-type containing 12 | Other | enzyme |
| 10 | TERC | −2.4 | telomerase RNA component | Other | other |
| 11 | SCARNA10 | −2.4 | small Cajal body-specific RNA 10 | Other | other |
| 12 | SLC37A4 | −2.3 | solute carrier family 37 (glucose-6-phosphate transporter), member 4 | Cytoplasm | transporter |
| 13 | RANGRF | −2.3 | RAN guanine nucleotide release factor | Plasma Membrane | transporter |
| 14 | MXD3 | −2.3 | MAX dimerization protein 3 | Nucleus | transcription regulator |
| 15 | C19orf60 | −2.3 | chromosome 19 open reading frame 60 | Other | other |
| 16 | RPL23AP32 | −2.3 | ribosomal protein L23a pseudogene 32 | Other | other |
| 17 | PRKCDBP | −2.3 | protein kinase C, delta binding protein | Cytoplasm | other |
| 18 | AURKAIP1 | −2.3 | aurora kinase A interacting protein 1 | Nucleus | enzyme |
| 19 | C19orf76 | −2.3 | adrenomedullin 5 (putative) | Other | other |
| 20 | RNASEH2C | −2.3 | ribonuclease H2, subunit C | Other | other |

Example IX

This example demonstrates that QN523 induces transcription of stress responsive genes. The unfold protein response genes DDIT3 and HSPA5 are among the top 20 upregulated genes, where DDIT3 synthesis was increased by 10.7 fold and HSPA5 by 7.9 fold (FIG. 6). Induction of these two genes accounts for ER stress and activation of unfolded protein responses as revealed by IPA and DAVID analysis, prostatic diseases 15(4): 320-328), which correlates with the results from bioinformatics analysis.

GDF15/NAG-1 is a TGF-beta family member that can be induced by non-steroidal anti-inflammatory drugs (NSAID) such as sulindac sulfide. It is proposed to inhibit inflammatory cytokine production. Transgenic mice expressing human NAG-1/GDF15 (NAG-1$^{Tg/Lox}$) are leaner with lower body weight and are resistant to chemically or genetically induced intestinal tumors (see, e.g., Kim J M, et al., (2013)

Mediators of inflammation 2013: 641851). GDF15 is also identified as a p53 target gene and inhibits prostate carcinoma cell growth through TGF-beta signaling pathway (see, e.g., Tan M, Wang Y, Guan K, Sun Y (2000) Proceedings of the National Academy of Sciences of the United States of America 97(1): 109-114). Induction of DNA damage and p53 overexpression triggers growth arrest and apoptosis in breast cancer cells through GDF15 expression (see, e.g., Li P X, Wong J, Ayed A, Ngo D, Brade A M, Arrowsmith C, et al. (2000) The Journal of biological chemistry 275(26): 20127-20135).

Importance of GDF15 for inhibition of tumor growth and metastasis has been well explored in the context of prostate cancer; however, its cellular receptor is still unknown (see, e.g., Vanhara P, Hampl A, Kozubik A, Soucek K (2012) Prostate cancer and prostatic diseases 15(4): 320-328). GDF15 expression is increased by TPA (10 ng/mL for 1.5-24 h) in prostate cancer cell line LNCaP, and its induced expression could be abolished by pretreatment with PKC inhibitor (GF109230x) but not other kinase inhibitors. Forced expression of constitutively active PKC-alpha or PKC-theta could upregulate basal expression of GDF15 as well, suggesting PKC as a direct regulator of GDF15 expression in LNCaP. Inhibition of GDF15 expression by siRNA partially blocks the TPA induced apoptosis in LNCaP cells, further confirming GDF15 as an inducer of growth arrest/apoptosis (see, e.g., Shim M, Eling T E (2005) The Journal of biological chemistry 280(19): 18636-18642). In DU-145 cells, treatment with GDF15 also shows antitumor effect by inhibiting cell migration and inducing apoptosis (see, e.g., Liu T, et al., (2003) Cancer research 63(16): 5034-5040).

ATF3 is a member of the bZIP family transcription factor and recognized as a tumor suppressor (see, e.g., Hai T, Hartman M G (2001) Gene 273(1): 1-11). For anti-cancer effect of the folate antimetabolite pemetrexed in NSCLC, induction of ATF3 is necessary for NOXA-mediated apoptosis (see, e.g., Yan J, Zhong N, Liu G, Chen K, Liu X, Su L, et al. (2014) Cell death & disease 5: e1316). GDF15 and ATF3 are co-induced by several compounds, including indole-3-carbinol, 5F-203 and sulindac (see, e.g., Bottone F G, Jr., Martinez J M, Collins J B, Afshari C A, Eling T E (2003) The Journal of biological chemistry 278(28): 25790-25801; Baek S J, et al., (2004) Carcinogenesis 25(12): 2425-2432; Lee S H, et al., (2005) Biochemical and biophysical research communications 328(1): 63-69; Monks A, et al., (2003) Molecular pharmacology 63(3): 766-772). Possessing the C/EBP binding site at its promoter region, GDF15 transcription is activated upon association with C/EBPβ and ATF3 in HCT-116 model (see, e.g., Lee S H, Krisanapun C, Baek S J (2010) Carcinogenesis 31(4): 719-728). The study on conjugated linoleic acid (CLA, 50 µM, 24 h) further revealed AKT/GSK3b/ATF3 dependent expression of GDF15 in colon cancer cells (HCT-116 and HT-29) in p53-independent manner as compared with all the above agents. Constitutively active β-catenin construct increased cyclin D1 promoter activity, but not GDF15 transcription. In this study, ATF3 expression precedes GDF15 expression as early as 3 hrs after treatment, and is responsible for GDF15 promoter activity (luciferase reporter construct) as confirmed by drug induced ATF3 and plasmid mediated overexpression of ATF3. siRNA of GDF15 can partially block CLA induced apoptosis (see, e.g., Lee S H, et al., (2006) Carcinogenesis 27(5): 972-981).

Example X

Figure 7:
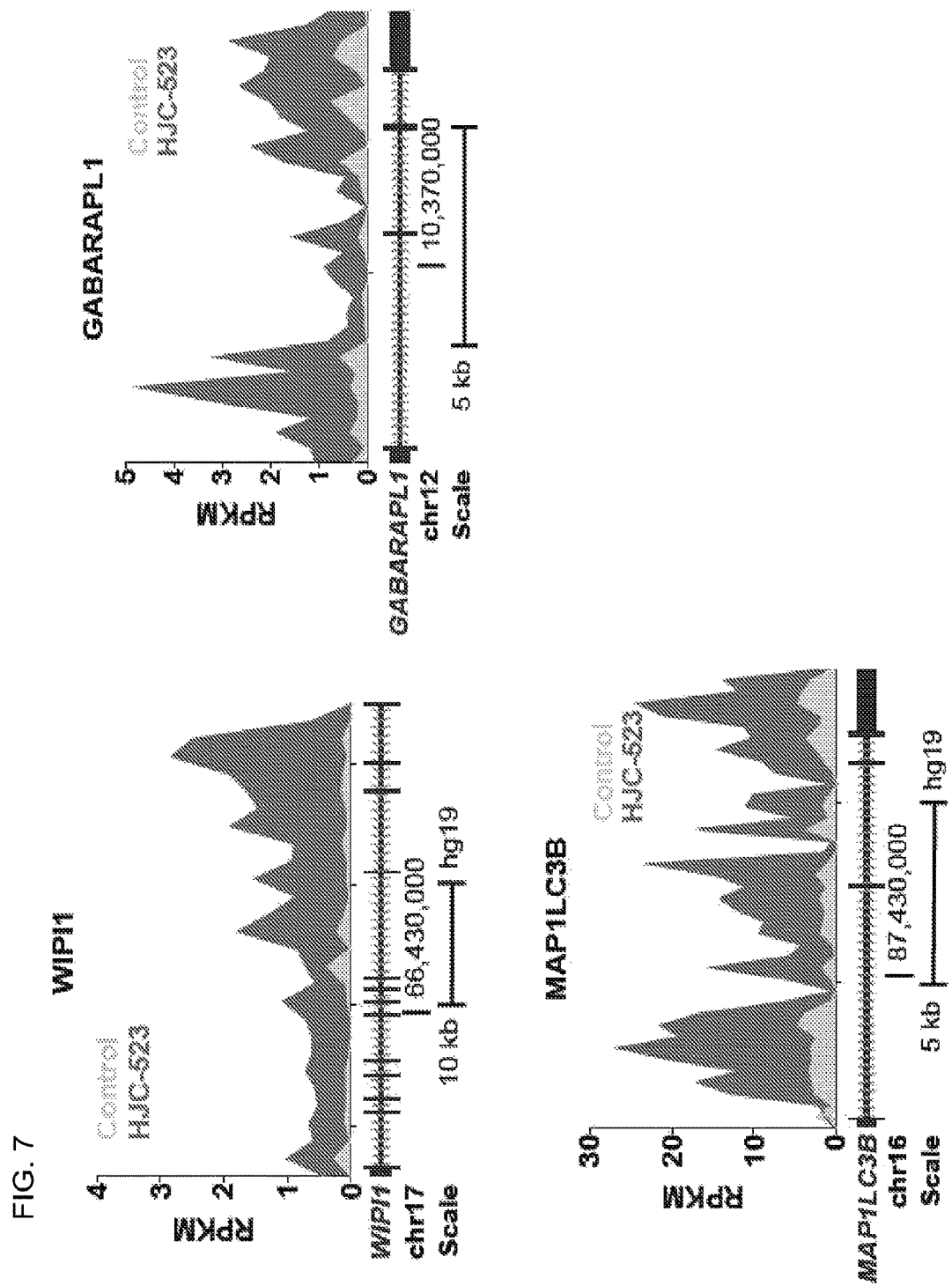
FIG. 7: QN523 induces transcription of autophagy related genes.

This example demonstrates that QN523 induces transcription of autophagy related genes. Interestingly, characterization of the up-regulated gene list revealed three autophagy related genes among the top 20 (FIG. 7). WIPI1, GABA-RAPL1 and MAP1LC3B are all reported as autophagy component proteins (see, e.g., Deretic V, Saitoh T, Akira S (2013) Nature reviews. Immunology 13(10): 722-737; Yang J, Carra S, Zhu W G, Kampinga H H (2013) International journal of biological sciences 9(10): 1121-1133). However, this functional group of genes was not identified by bioinformatics analysis, suggesting lack of autophagy characterization in the current bioinformatics databases. The concurrent induction of autophagic markers strongly suggests involvement of autophagy in QN523 cellular activity, and warrants further studies using these markers.

Autophagy is a cellular process for repositioning and recycling building blocks, representing a central component of the integrated stress response (see, e.g., Kroemer G, Marino G, Levine B (2010) Molecular cell 40(2): 280-293). It starts by forming double-layer-membrane vesicles from intracellular organelles like ER. Autophagy proteins accumulate on the vesicles and the vesicles (which can be detected by puncta formation by GFP-LC3B) are then fuse with lysosome to form autolysosome and trigger degradation and reuse of the vesicle contents. Protein levels of LC3B, the MAP1LC3B gene product, are often taken as a marker for autophagy activation.

QN523 induced upregulation of MAP1LC3B, GABA-RAPL1 and WIPI1. In gene ontology, these genes fall into two major functional groups that are crucial for autophagy. MAP1LC3A, MAP1LC3B, MAP1LC3C, GABARAP, GABARAPL1, and GABARAPL2 are yeast ATG8 orthologs, and WIPI (WD repeat protein interacting with phosphoinositides) family members including WIPI1, WIPI2, WDR45B and WDR45 are yeast ATG18 orthologs.

WIPI1 was identified as a marker of autophagosome formation across a wide range of cell lines following thapsigargin and C2-ceramide treatment (see, e.g., Tsuyuki S, et al., (2014) Autophagy 10(3): 497-513). Thapsigargin and tunicamycin are ER stress inducers with similar temporal changes in expression profile of genes with unfolded protein response element (UPRE) and ER stress element (ERSE) (see, e.g., Dombroski B A, et al., (2010) American journal of human genetics 86(5): 719-729). In HeLa cells, 0.5 µM thapsigargin or 2 µg/mL tunicamycin treatment for 8 h induced cellular stress including autophagy and ER stress by increasing cellular calcium ion concentration; and induced WIPI1 mRNA transcription was associated with ER-stress related autophagy (see, e.g., Ogata M, et al., (2006) Molecular and cellular biology 26(24): 9220-9231; Sakaki K, Wu J, Kaufman R J (2008) The Journal of biological chemistry 283(22): 15370-15380). As a sensitive marker for formation of autophagosome, WIPI1 serves as the back up preparation for protein synthesis after autophagy, and is eventually degraded in the autolysosome (see, e.g., Tsuyuki S, et al., (2014) Autophagy 10(3): 497-513).

Interestingly, NSAIDs are also associated with activation of autophagy. Aspirin inhibits mTOR signaling in colorectal cancer cells by inhibiting S6K1(p-Thr389), S6 (p-Ser235) and 4EBP1(p-Ser65) at 5 mM 8-16 h treatment, activated AMPK, and induces autophagy as shown with LC3B accumulation (see, e.g., Din F V, et al., (2012) Gastroenterology 142(7): 1504-1515 e1503). Sulindac sulfide induces autophagic death in gastric epithelial cells, where pretreatment with autophagy inhibitors 3-methyladenine and chloroquine inhibits autophagy as well as cell death associated with Sulindac treatment. Celecoxib (80-120 µM, 48 h) also induces both apoptosis and autophagy in HT-29 and HCT-116. However, inhibition of autophagy increases the celecoxib-induced apoptosis in this model (see, e.g., Huang S, Sinicrope F A (2010) Autophagy 6(2): 256-269). These previous studies show that cellular stress induced by NSAIDs could trigger activation of the autophagy program, however, cell fate determination might be context or condition-dependent.

Example XI

This example describes proposed markers for cytotoxicity of QN523. Considering the similarity in stressed-associated transcription profiles of QN523 and NSAIDs, it was proposed that activation of stress signaling program and autophagy might be the major mechanisms for QN523 cytotoxicity. The four highly unregulated stress responsive genes HSPA5, DDIT3, ATF3 and GDF15, and the three autophagic markers WIPI1, GABARAPL1 and MAP1LC3B could serve as markers as well as potential drivers for QN523 anti-cancer activity. Their roles in cytotoxicity of QN523 warrant further investigation.

Figure 8:
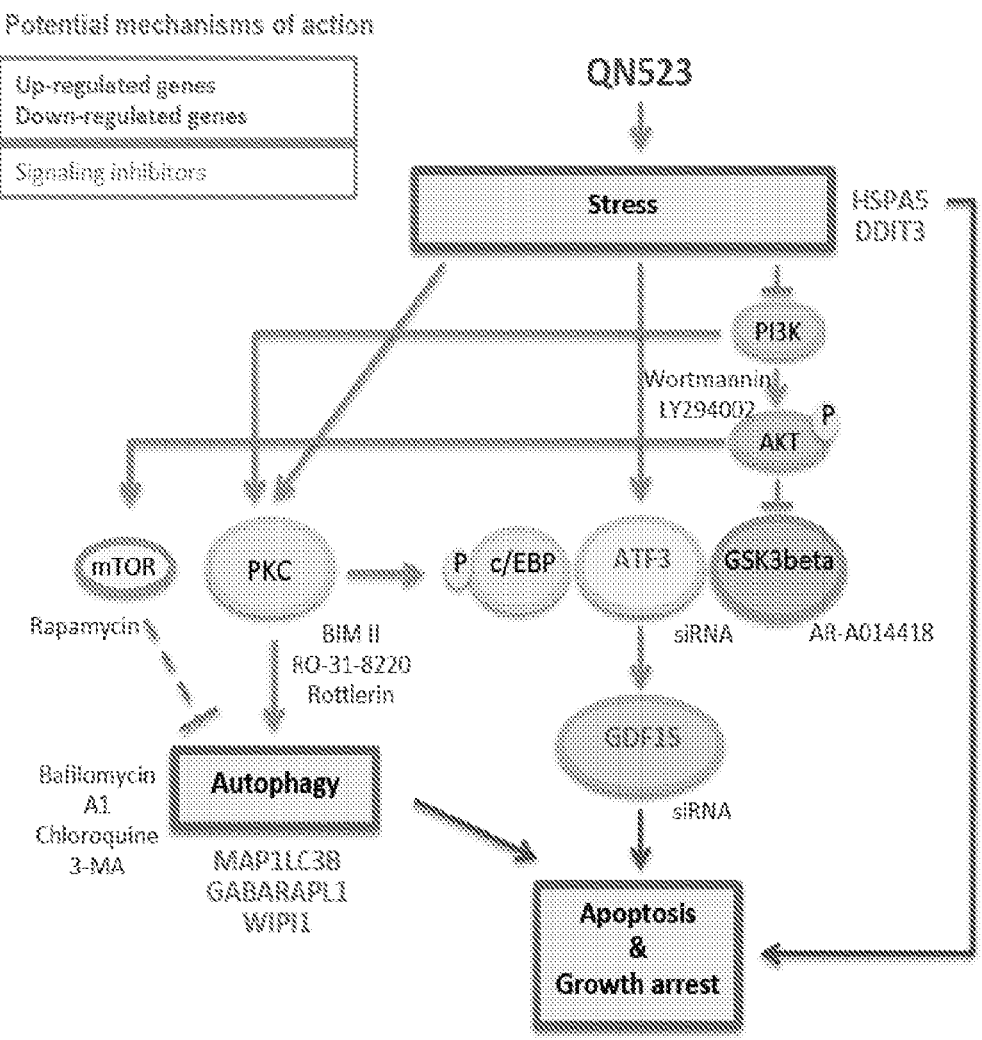
FIG. 8: Proposed model for mechanisms of action of QN523. Reagents in purple represent potential pharmacological or genetic tools that can be used for characterization of QN523 activity and validation of the model.

On the basis of cellular regulatory networks characterized with our preliminary data and studies mentioned above, a stress associated mechanistic model of QN523 (FIG. 8) was proposed, where QN523 triggers specific stress signaling pathways to activate autophagy, growth arrest and apoptosis. The application of signaling inhibitors and genetic modulators in validation process was investigated so as to understand the role of each cellular responder or pathway in the context of QN523 anti-cancer activity.

Example XII

This example describes the discovery of compounds showing similar activity with QN523. The similar transcriptional regulation on stress responsive genes and autophagy-related genes of QN523 and NSAIDs prompted investigation of whether there are other compounds that triggers similar transcriptional profiles as QN523. Identification of such compounds will not only help to understand QN523's mechanisms of action, but might also inspire positioning of this compound as chemical tool or treatment for diseases besides cancer.

Example XIII

This example describes the use of NextBio analysis. Application of the NextBio database allows for discovery of compounds regulating the gene of interest. Here the top 20 compounds regulating expression of our seven marker genes HSPA5, DDIT3, ATF3, GDF15, WIPI1, GABARAPL1 and MAP1LC3B (Tables 7 to 13) are reported. Distinct lists were obtained for each marker. A correlation score of 50 was used as selection criteria and compared the lists for different markers. While no compound up-regulated all markers at the same time, the liver X receptor non-steroidal agonist GW 3965 could concurrently upregulate HSPA5, DDIT3, ATF3, GDF15, WIPI1 and MAP1LC3B. The compound was reported to inhibit development of atherosclerosis in mice (see, e.g., Joseph S B, et al., (2002) Proceedings of the National Academy of Sciences of the United States of America 99(11): 7604-7609) and reduce angiotentsin II-mediated vasopressor responses in rats (see, e.g., Leik C E, et al., (2007) British journal of pharmacology 151(4): 450-456). On the other hand, the natural steroid lactone withaferin A upregulates the six markers except HSPA5. Withaferin A displays anti-inflammatory and antitumor activity by inhibiting IKKβ and NF-κB activation (see, e.g., Kaileh M, et al., (2007) The Journal of biological chemistry 282(7): 4253-4264). It is also a potent inhibitor of angiogenesis (see, e.g., Mohan R, et al., (2004) Angiogenesis 7(2): 115-122).

TABLE 7

Top 20 compounds affecting HSPA5 expression in NextBio

| | compounds | compounds score | compounds group | # Studies | Effect on Query |
|---|---|---|---|---|---|
| 1 | mebhydroline | 100 | Neurotransmitter Agents | 1 | up-regulated |
| 2 | Protriptyline | 91.82152794 | Neurotransmitter Agents | 1 | up-regulated |
| 3 | Trifluoperazine | 84.55492451 | Neurotransmitter Agents | 1 | up-regulated |
| 4 | Arecoline | 84.42716643 | Neurotransmitter Agents | 1 | up-regulated |
| 5 | Procyclidine | 80.4707731 | Neurotransmitter Agents | 1 | up-regulated |
| 6 | Dextromethorphan | 80.4707731 | Neurotransmitter Agents | 1 | up-regulated |
| 7 | Propafenone | 80.4707731 | Unclassified Mechanisms of Action | 1 | up-regulated |
| 8 | butoconazole | 78.30004229 | Unclassified Mechanisms of Action | 1 | up-regulated |
| 9 | Tunicamycin | 76.40694171 | Unclassified Mechanisms of Action | 12 | up-regulated |
| 10 | Nefopam | 76.02398954 | Unclassified Mechanisms of Action | 1 | up-regulated |
| 11 | AICA ribonucleotide | 75.07220517 | Unclassified Mechanisms of Action | 1 | down-regulated |
| 12 | Coumarins | 75.02173008 | Unclassified Mechanisms of Action | 1 | down-regulated |
| 13 | Mycophenolic Acid | 74.0440831 | Enzyme Inhibitors | 2 | down-regulated |
| 14 | Doxycycline | 69.19710395 | Unclassified Mechanisms of Action | 4 | up-regulated |
| 15 | 1-(5-Isoquinolinesulfonyl)-2-Methylpiperazine | 69.14055065 | Enzyme Inhibitors | 1 | down-regulated |
| 16 | Hexetidine | 66.58030963 | Unclassified Mechanisms of Action | 1 | up-regulated |
| 17 | GW 3965 | 65.54187446 | Unclassified Mechanisms of Action | 2 | up-regulated |
| 18 | bacterial lysate | 65.2288713 | Unclassified Mechanisms of Action | 1 | up-regulated |
| 19 | versipelostatin | 64.70946821 | Enzyme Inhibitors | 1 | up-regulated |
| 20 | chlorcyclizine | 63.88901118 | Neurotransmitter Agents | 1 | up-regulated |

TABLE 8

Top 20 compounds affecting DDIT3 expression in NextBio

| | compounds | compounds score | compounds group | # Studies | Effect on Query |
|---|---|---|---|---|---|
| 1 | 2-tert-butyl-9-fluoro-3,6-dihydro-7H-benz(h)imidazo(4,5-f)isoquinoline-7-one | 100 | Enzyme Inhibitors | 1 | up-regulated |
| 2 | Gossypol | 96.06378595 | Unclassified Mechanisms of Action | 1 | up-regulated |
| 3 | Ethionamide | 95.21587961 | Antimetabolites | 3 | up-regulated |
| 4 | Thapsigargin | 95.0460866 | Enzyme Inhibitors | 4 | up-regulated |
| 5 | rottlerin | 93.59798309 | Enzyme Inhibitors | 1 | up-regulated |
| 6 | tyrphostin AG 1478 | 93.01833575 | Enzyme Inhibitors | 1 | up-regulated |
| 7 | GW 3965 | 90.46613224 | Unclassified Mechanisms of Action | 2 | up-regulated |
| 8 | Tunicamycin | 90.2571037 | Unclassified Mechanisms of Action | 11 | up-regulated |
| 9 | halofuginone | 87.67104908 | Enzyme Inhibitors | 2 | up-regulated |
| 10 | Hypericum extract LI 160 | 86.99050969 | Unclassified Mechanisms of Action | 1 | up-regulated |
| 11 | Lasalocid | 84.14299 | Membrane Transport Modulators | 1 | up-regulated |
| 12 | cyclobenzaprine | 84.01944622 | Unclassified Mechanisms of Action | 1 | up-regulated |
| 13 | lactacystin | 82.75915967 | Enzyme Inhibitors | 2 | up-regulated |
| 14 | withaferin A | 82.75362316 | Unclassified Mechanisms of Action | 2 | up-regulated |
| 15 | syrosingopine | 81.16394084 | Unclassified Mechanisms of Action | 1 | up-regulated |
| 16 | Dequalinium | 81.08332783 | Unclassified Mechanisms of Action | 1 | up-regulated |
| 17 | benzyloxycarbonylleucyl-leucyl-leucine aldehyde | 80.37611397 | Enzyme Inhibitors | 4 | up-regulated |
| 18 | BW B70C | 80.33532353 | Enzyme Inhibitors | 1 | up-regulated |
| 19 | Deoxycholic Acid | 79.13922935 | Unclassified Mechanisms of Action | 2 | up-regulated |
| 20 | Monensin | 78.72961707 | Membrane transport modulator | 1 | up-regulated |

TABLE 9

Top 20 compounds affecting ATF3 expression in NextBio

| | compounds | compounds score | compounds group | # Studies | Effect on Query |
|---|---|---|---|---|---|
| 1 | 1,3-dichloro-2-propanol | 100 | Unclassified Mechanisms of Action | 1 | up-regulated |
| 2 | BW B70C | 95.75439152 | Enzyme Inhibitors | 1 | up-regulated |
| 3 | 1-hydroxycholecalciferol | 95.34075062 | Unclassified Mechanisms of Action | 4 | up-regulated |
| 4 | ferulic acid | 94.93951628 | Antioxidants | 2 | up-regulated |
| 5 | Hexetidine | 93.18846827 | Unclassified Mechanisms of Action | 1 | up-regulated |
| 6 | geraniol | 93.05269705 | Unclassified Mechanisms of Action | 4 | up-regulated |
| 7 | Acyclovir | 91.58587069 | Unclassified Mechanisms of Action | 4 | up-regulated |
| 8 | Astemizole | 91.07344824 | Neurotransmitter Agents | 1 | up-regulated |
| 9 | Ethionamide | 90.78306743 | Antimetabolites | 2 | up-regulated |
| 10 | pyrvinium | 89.52931316 | Unclassified Mechanisms of Action | 2 | up-regulated |
| 11 | Bepridil | 89.23207495 | Membrane Transport Modulators | 1 | up-regulated |
| 12 | bromperidol | 88.94271426 | Unclassified Mechanisms of Action | 1 | up-regulated |
| 13 | cyanoginosin LR | 88.56272774 | Enzyme Inhibitors | 3 | up-regulated |
| 14 | cetraxate | 88.28387843 | Unclassified Mechanisms of Action | 2 | up-regulated |
| 15 | azacyclonol | 87.77912444 | Unclassified Mechanisms of Action | 1 | up-regulated |
| 16 | Proadifen | 87.77912444 | Enzyme Inhibitors | 1 | up-regulated |
| 17 | eperisone | 87.3855813 | Membrane Transport Modulators | 2 | up-regulated |
| 18 | Vanadates | 87.24961305 | Membrane Transport Modulators | 2 | up-regulated |
| 19 | Cinnarizine | 87.16163703 | Membrane Transport Modulators | 3 | up-regulated |
| 20 | Deoxycholic Acid | 86.64258625 | Unclassified Mechanisms of Action | 3 | up-regulated |

TABLE 10

Top 20 compounds affecting GDF15 expression in NextBio

| | compounds | compounds score | compounds group | # Studies | Effect on Query |
|---|---|---|---|---|---|
| 1 | 4-amino-6-hydrazino-7-beta-D-ribofuranosyl-7H-pyrrolo(2,3-d)-pyrimidine-5-carboxamide | 100 | Enzyme Inhibitors | 1 | up-regulated |
| 2 | Mitomycin | 95.7056062 | Alkylating Agents | 5 | up-regulated |
| 3 | Ethyl Methanesulfonate | 94.3983552 | Alkylating Agents | 1 | up-regulated |
| 4 | Deoxycholic Acid | 86.51680945 | Unclassified Mechanisms of Action | 1 | up-regulated |
| 5 | Potassium Dichromate | 74.69238994 | Unclassified Mechanisms of Action | 1 | up-regulated |
| 6 | Demecolcine | 73.59595293 | Mitosis Modulators | 1 | up-regulated |
| 7 | Papaverine | 73.13980763 | Enzyme Inhibitors | 3 | up-regulated |
| 8 | lactacystin | 72.84717128 | Enzyme Inhibitors | 2 | up-regulated |
| 9 | methixene | 69.39413606 | Unclassified Mechanisms of Action | 1 | up-regulated |

TABLE 10-continued

Top 20 compounds affecting GDF15 expression in NextBio

| compounds | compounds score | compounds group | # Studies | Effect on Query |
|---|---|---|---|---|
| 10 2,2'-(hydroxynitrosohydrazono)bis-ethanamine | 69.37492206 | Nitric Oxide Donors | 1 | up-regulated |
| 11 Lasalocid | 68.90592316 | Membrane Transport Modulators | 1 | up-regulated |
| 12 pyrvinium | 65.98164722 | Unclassified Mechanisms of Action | 2 | up-regulated |
| 13 Monensin | 65.88926271 | Membrane Transport Modulators | 1 | up-regulated |
| 14 securinine | 65.1400566 | Neurotransmitter Agents | 1 | up-regulated |
| 15 1,3-dichloro-2-propanol | 64.2813855 | Unclassified Mechanisms of Action | 1 | up-regulated |
| 16 Amodiaquine | 64.0301516 | Unclassified Mechanisms of Action | 1 | up-regulated |
| 17 GW 3965 | 62.91015204 | Unclassified Mechanisms of Action | 2 | up-regulated |
| 18 Danazol | 62.90351426 | Unclassified Mechanisms of Action | 8 | up-regulated |
| 19 naftifine | 60.86658033 | Unclassified Mechanisms of Action | 1 | up-regulated |
| 20 Niclosamide | 60.73935532 | Unclassified Mechanisms of Action | 1 | up-regulated |

TABLE 11

Top 20 compounds affecting WIPI1 expression in NextBio

| compounds | compounds score | compounds group | # Studies | Effect on Query |
|---|---|---|---|---|
| 1 Desipramine | 100 | Enzyme Inhibitors | 1 | up-regulated |
| 2 Methiothepin | 96.66027784 | Neurotransmitter Agents | 2 | up-regulated |
| 3 monastrol | 93.30234878 | Unclassified Mechanisms of Action | 3 | up-regulated |
| 4 Trimipramine | 88.69696304 | Neurotransmitter Agents | 5 | up-regulated |
| 5 Flupenthixol | 88.38301982 | Neurotransmitter Agents | 6 | up-regulated |
| 6 Lidoflazine | 87.51725941 | Membrane Transport Modulators | 7 | up-regulated |
| 7 dimethisoquin | 87.4829848 | Unclassified Mechanisms of Action | 8 | up-regulated |
| 8 Lasalocid | 85.51468732 | Membrane Transport Modulators | 9 | up-regulated |
| 9 Trifluoperazine | 83.4783669 | Neurotransmitter Agents | 10 | up-regulated |
| 10 homochlorocyclizine | 83.37332255 | Neurotransmitter Agents | 11 | up-regulated |
| 11 Prochlorperazine | 82.95354155 | Neurotransmitter Agents | 12 | up-regulated |
| 12 bafilomycin A | 82.57299728 | Enzyme Inhibitors | 13 | up-regulated |
| 13 Clopenthixol | 81.04285669 | Neurotransmitter Agents | 14 | up-regulated |
| 14 Bufexamac | 80.91397366 | Unclassified Mechanisms of Action | 15 | up-regulated |
| 15 acetorphan | 80.25373028 | Enzyme Inhibitors | 16 | up-regulated |
| 16 isocorydine | 80.25373028 | Unclassified Mechanisms of Action | 18 | up-regulated |
| 17 Aclarubicin | 79.9799851 | Unclassified Mechanisms of Action | 19 | up-regulated |
| 18 Monensin | 79.38144581 | Membrane Transport Modulators | 20 | up-regulated |
| 19 Nicergoline | 79.00912279 | Neurotransmitter Agents | 21 | up-regulated |
| 20 Chenodeoxycholic Acid | 78.56708322 | Unclassified Mechanisms of Action | 22 | up-regulated |

TABLE 12

Top 20 compounds affecting GABARAPL1 expression in NextBio

| compounds | compounds score | compounds group | # Studies | Effect on Query |
|---|---|---|---|---|
| 1 clemizole | 100 | Neurotransmitter Agents | 1 | down-regulated |
| 2 Oxyphenbutazone | 94.54340488 | Unclassified Mechanisms of Action | 1 | up-regulated |
| 3 Streptomycin | 91.97135628 | Enzyme Inhibitors | 1 | up-regulated |
| 4 Xylazine | 90.57377267 | Neurotransmitter Agents | 1 | down-regulated |
| 5 butoconazole | 86.61005582 | Unclassified Mechanisms of Action | 1 | up-regulated |
| 6 Ampicillin | 86.51099014 | Unclassified Mechanisms of Action | 1 | up-regulated |
| 7 PI103 | 77.34687372 | Enzyme Inhibitors | 1 | up-regulated |
| 8 Trioxsalen | 74.89571659 | Unclassified Mechanisms of Action | 1 | up-regulated |
| 9 fenbufen | 71.04088548 | Enzyme Inhibitors | 1 | down-regulated |
| 10 Acetohexamide | 70.92962897 | Unclassified Mechanisms of Action | 1 | up-regulated |
| 11 acetylleucine | 70.46435417 | Unclassified Mechanisms of Action | 1 | down-regulated |
| 12 Apazone | 70.46435417 | Unclassified Mechanisms of Action | 1 | up-regulated |
| 13 Pantothenic Acid | 70.46435417 | Unclassified Mechanisms of Action | 1 | up-regulated |
| 14 bortezomib | 67.93989966 | Enzyme Inhibitors | 7 | up-regulated |
| 15 N-benzyladenine | 64.24225268 | Unclassified Mechanisms of Action | 1 | up-regulated |
| 16 Meclofenoxate | 64.08969585 | Unclassified Mechanisms of Action | 1 | down-regulated |
| 17 butamben | 64.06215313 | Unclassified Mechanisms of Action | 1 | down-regulated |
| 18 Cefoperazone | 63.81543286 | Unclassified Mechanisms of Action | 1 | down-regulated |
| 19 Pentolinium Tartrate | 63.01565541 | Neurotransmitter Agents | 1 | down-regulated |
| 20 pimethixene | 62.85661086 | Neurotransmitter Agents | 1 | up-regulated |

TABLE 13

Top 20 compounds affecting MAP1LC3B expression in NextBio

| | compounds | compounds score | compounds group | # Studies | Effect on Query |
|---|---|---|---|---|---|
| 1 | Ethoxyquin | 100 | Antioxidants | 1 | up-regulated |
| 2 | trimethylcolchicinic acid | 75.96088895 | Unclassified Mechanisms of Action | 1 | up-regulated |
| 3 | Cymarine | 70.55146591 | Unclassified Mechanisms of Action | 1 | up-regulated |
| 4 | Acetylmuramyl-Alanyl-Isoglutamine | 68.31431976 | Unclassified Mechanisms of Action | 1 | down-regulated |
| 5 | carbetapentane | 68.01648238 | Unclassified Mechanisms of Action | 1 | down-regulated |
| 6 | Gossypol | 66.313867 | Unclassified Mechanisms of Action | 1 | up-regulated |
| 7 | Chorionic Gonadotropin | 66.21053244 | Unclassified Mechanisms of Action | 4 | up-regulated |
| 8 | Hydroxyzine | 62.14316764 | Neurotransmitter Agents | 1 | down-regulated |
| 9 | monobenzone | 61.02261463 | Unclassified Mechanisms of Action | 1 | up-regulated |
| 10 | GW 3965 | 60.68424478 | Unclassified Mechanisms of Action | 2 | up-regulated |
| 11 | rottlerin | 60.39782588 | Enzyme Inhibitors | 1 | up-regulated |
| 12 | Clioquinol | 59.01263647 | Unclassified Mechanisms of Action | 1 | up-regulated |
| 13 | Histidinol | 57.00502349 | Enzyme Inhibitors | 1 | up-regulated |
| 14 | pioglitazone | 56.88519534 | Unclassified Mechanisms of Action | 3 | up-regulated |
| 15 | Phenoxybenzamine | 56.78538959 | Neurotransmitter Agents | 1 | up-regulated |
| 16 | Spiperone | 56.71940139 | Neurotransmitter Agents | 1 | up-regulated |
| 17 | piperlonguminine | 56.58188398 | Enzyme Inhibitors | 1 | up-regulated |
| 18 | Fendiline | 56.58108686 | Membrane Transport Modulators | 1 | up-regulated |
| 19 | Nerve Growth Factors | 55.97089611 | Unclassified Mechanisms of Action | 1 | down-regulated |
| 20 | withaferin A | 55.29247785 | Unclassified Mechanisms of Action | 2 | up-regulated |

Figure 9:
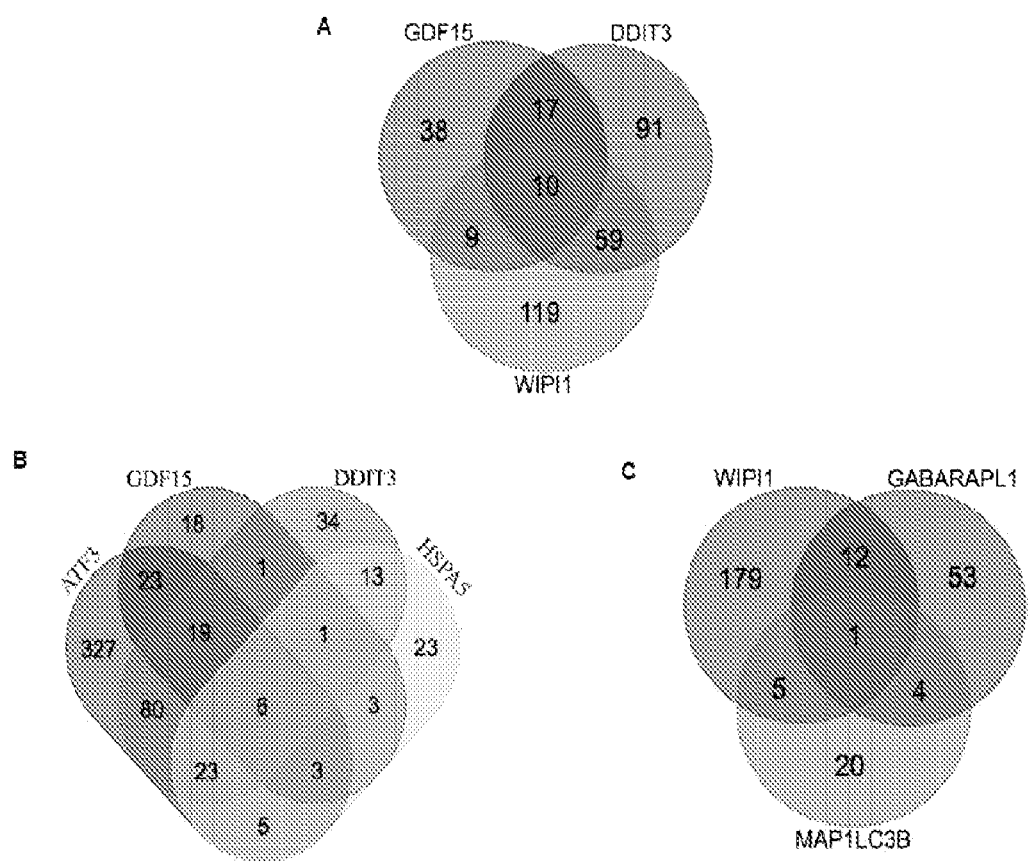
FIG. 9A-C: Venn diagrams for comparison of compounds regulating potential marker genes (compound correlation score >50). A) Comparison of GDF15, DDIT3 and WIPI1. B) Comparison of stress responsive genes HSPA5, DDIT3, ATF3 and GDF15. C) Comparison of autophagy related genes WIPI1, GABARAPL1 and MAP1LC3B.

Using GDF15 as a marker for stress target genes, DDIT3 for unfolded protein response, and WIPI1 for autophagy related signaling, there are 10 compounds concurrently activating these three pathways, but clear correlation in cellular functions of these compounds were not observed (FIG. 9A). For the lists of the four stress related genes, there are 6 compounds in common, namely niclosamide, loperamide, GW 3965, lasalocid, doxycycline and homochlorocyclizine (FIG. 9B). For the three autophagy-related genes, withaferin A is the only compound that shows concurrent up-regulation.

Example XIV

This examples describes the use of MAP analysis. Besides using the most highly regulated genes as key transcription signatures as described with NextBio analysis discussed above, comparison of the overall transcription profile serve as another approach to identify compounds with similar cellular activity. The up and downregulated gene lists were used to query the CMAP database for overall transcription profiles of in-house perturbagens. The top 20 perturbagens (compounds) correlating with QN523 transcription profile is reported here (Table 14). Five adrenergic or dopamine receptor antagonists were identified in the list. Although these compounds require systemic administration for their therapeutic benefits, similarity of transcription profiles with these compounds suggests potential correlation in mechanisms of action. Also two Hsp90 inhibitors geldanamycin and 17-AAG are identified as showing similar transcription profiles with QN523, suggesting the involvement of stress responses.

TABLE 14

Top 20 compounds correlating with QN523 transcription profile n connectivity map

| rank | cmap name | mean | n | enrichment | p | specificity | percent non-null | note |
|---|---|---|---|---|---|---|---|---|
| 1 | phenoxybenzamine | 0.795 | 4 | 0.972 | 0 | 0.0891 | 100 | A non-selective, irreversible alpha antagonist |
| 2 | puromycin | 0.754 | 4 | 0.966 | 0 | 0.0393 | 100 | An antibiotic that inhibits translation |
| 3 | GW-8510 | -0.599 | 4 | -0.946 | 0 | 0.0687 | 100 | An inhibitor of cyclin kinase 2 (CDK2) |
| 4 | geldanamycin | 0.619 | 15 | 0.83 | 0 | 0.0054 | 100 | A benzoquinone ansamycin antibiotic that inhibits Hsp90 |
| 5 | thioridazine | 0.683 | 20 | 0.755 | 0 | 0.0091 | 100 | An antipsychotic binding D2, M1, alpha1 and 5-HT |
| 6 | 15-delta prostaglandin J2 | 0.632 | 15 | 0.7 | 0 | 0.0447 | 86 | Selective PPARγ agonist |
| 7 | trifluoperazine | 0.594 | 16 | 0.698 | 0 | 0.0048 | 93 | An antipsychotic binding D1, D2 and adrenergic receptors |
| 8 | prochlorperazine | 0.561 | 16 | 0.619 | 0 | 0.0437 | 87 | A dopamine (D2) receptor antagonist |
| 9 | tanespimycin | 0.484 | 62 | 0.567 | 0 | 0.0259 | 83 | 17-AAG, a derivative of the antibiotic geldanamycin |
| 10 | trichostatin A | 0.464 | 182 | 0.518 | 0 | 0.2654 | 82 | Selective inhibitor for class I and II HDAC |
| 11 | anisomycin | 0.683 | 4 | 0.938 | 0.00002 | 0.0412 | 100 | Inhibits peptidyl transferase or the 80S ribosome system |
| 12 | astemizole | 0.798 | 5 | 0.923 | 0.00002 | 0.019 | 100 | A histamine H1-receptor antagonist |
| 13 | gossypol | 0.639 | 6 | 0.839 | 0.00002 | 0 | 100 | Inhibitor for several dehydrogenase enzymes |
| 14 | thapsigargin | 0.8 | 3 | 0.981 | 0.00004 | 0.0573 | 100 | A non-competitive inhibitor of the sarco/ER $Ca^{2+}$ ATPase |
| 15 | valinomycin | 0.661 | 4 | 0.925 | 0.00004 | 0.0174 | 100 | A dodecadepsipeptide antibiotic |
| 16 | LY-294002 | 0.278 | 61 | 0.283 | 0.00004 | 0.3893 | 63 | Inhibitor for PI3Ks |
| 17 | fluphenazine | 0.434 | 18 | 0.515 | 0.00006 | 0.0622 | 77 | A antipsychotic binding the dopamine D2 receptors |
| 18 | terfenadine | 0.762 | 3 | 0.963 | 0.00008 | 0.0197 | 100 | An antihistamine |
| 19 | pyrvinium | 0.721 | 6 | 0.815 | 0.00008 | 0.0279 | 100 | An anthelmintic effective for pinworms |
| 20 | 6-bromoindirubin-3'-oxime | -0.506 | 7 | -0.763 | 0.00008 | 0.0047 | 85 | BIO, a potent inibitor of GSK3α/β |

Figure 10:
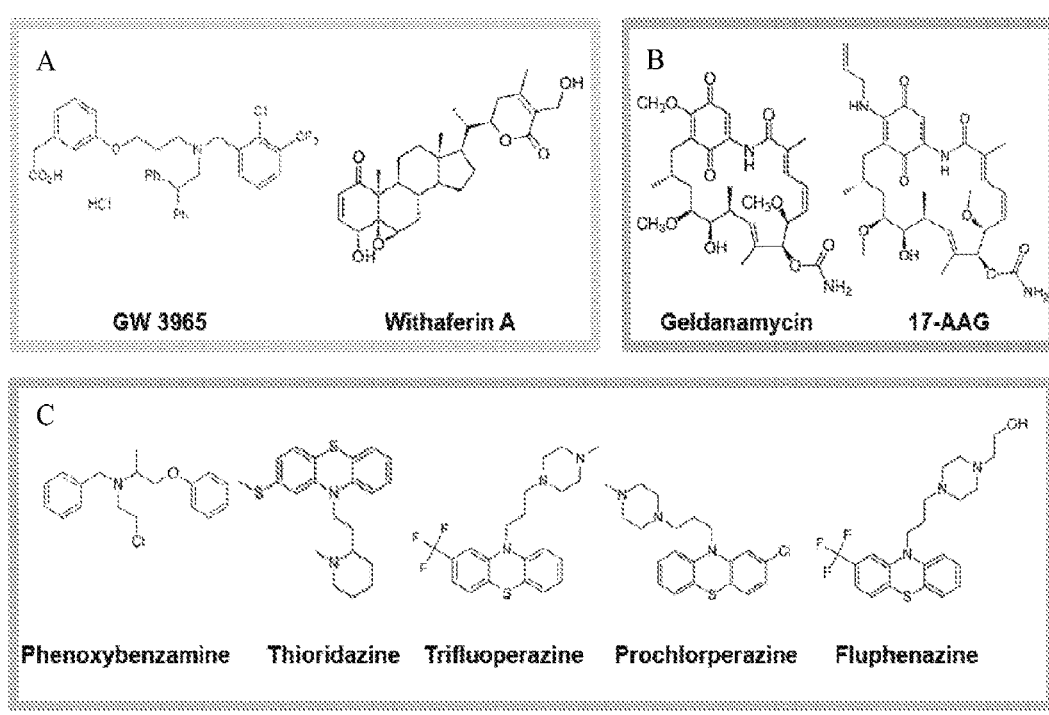
FIG. 10A-C: Compounds exhibiting similar transcription signatures with QN523. A) Compounds identified by Next-Bio analysis. B) HSP90 inhibitors identified by connectivity map (CMAP) C) Alpha or dopamine receptor antagonists identified by CMAP.

Compounds identified by NextBio or CMAP do not show significant structural similarity with QN523 (FIG. 10). However, correlation of these compounds hints on potential mechanisms QN523 activity, and application of these compounds as tools for comparison might be a plausible approach to further characterize QN523 in different biological systems.

Example XV

Figure 11:
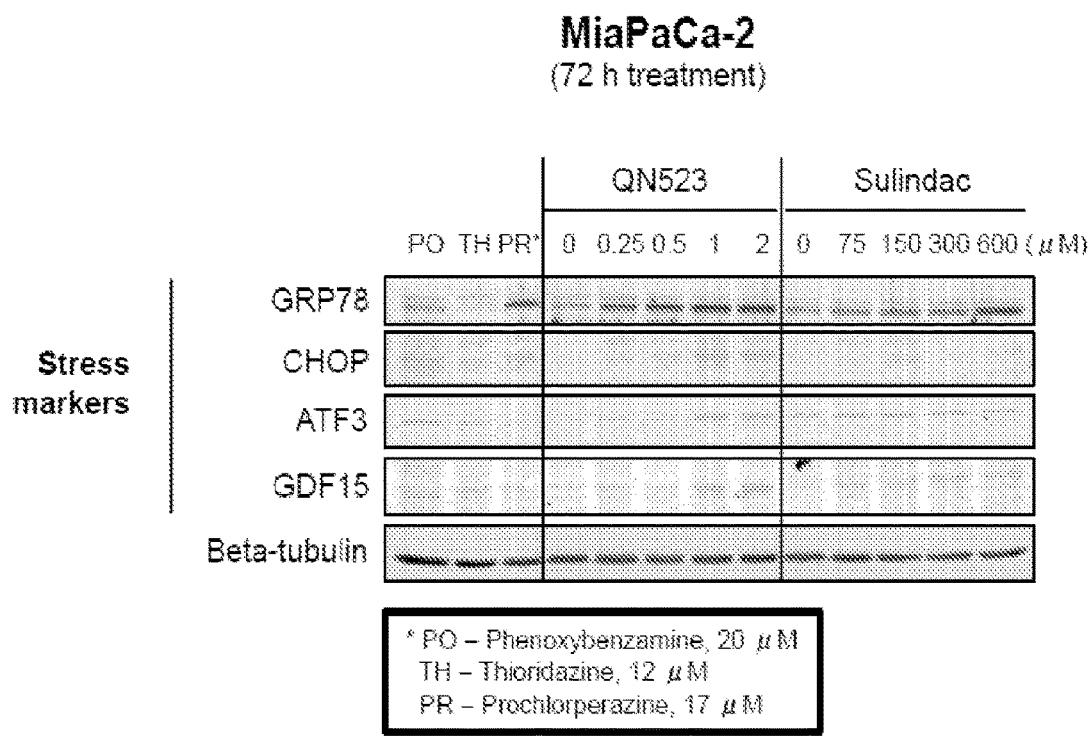
FIG. 11: QN523 induces protein expression of stress markers dose-dependently. MiaPaCa-2 cells were treated by QN523, Sulindac, phenoxybenzamine, thioridazine or prochlorperazine for 72 h and subjected to western blotting analysis of stress responsive proteins GRP78, CHOP, ATF3, GDF15.

This example describes the validation of biomarkers GDF15, ATF3, DDIT3, HSPA5, WIPI1, GABARAPL1 and MAP1LC3B in pancreatic cancer cell lines. To validate the findings from bioinformatics analysis basing on Bru-seq experiments, the proposed biomarkers were further tested in pancreatic cancer cell lines. In MiaPaCa-2, dose dependent upregulation was observed in protein levels of the stress responsive genes HSPA5, DDIT3, ATF3 and GDF15 (FIG. 11), suggesting that the regulation in RNA synthesis was further translated into changes in protein levels, which are essential for actual functional regulations in the cancer cells. The stress responsive markers were also induced by Sulindac treatment, in agreement with literature in other cancer models mentioned above. However, the potency of Sulindac is much lower than that of QN523, with $IC_{50}$ of 300 μM in MiaPaCa-2.

Three select compounds from CMAP analysis were also tested. The adrenergic antagonist pheoxybenzamine was not cytotoxic in MiaPaCa-2 ($IC_{50}$>30 μM), while the phenothiazine dopamine receptor antagonists thioridazine ($IC_{50}$=12 μM) and prochlorperazine ($IC_{50}$=17 μM) induced inhibition of cell proliferation. When tested at their $IC_{50}$ values (except for non-cytotoxic phenoxybenzamine), the three compounds exhibits induction of the stress responsive markers. Among them, prochlorperazine showed most robust induction of GRP78 and CHOP.

Figure 12:
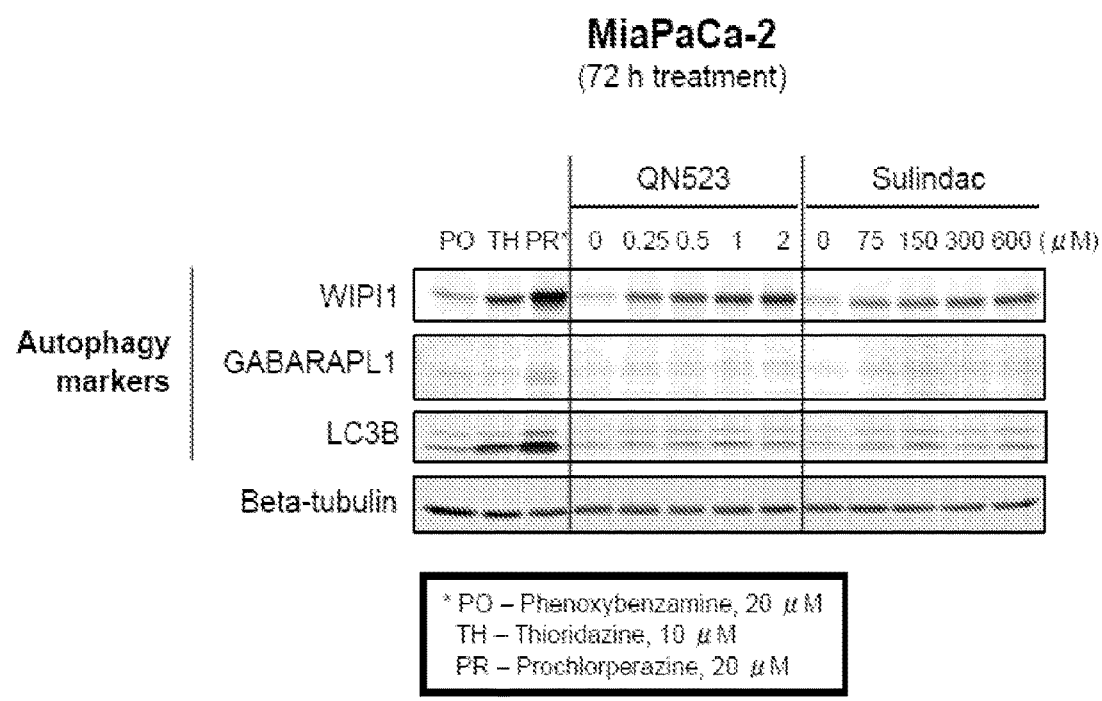
FIG. 12: QN523 induces protein expression of autophagy markers dose-dependently. MiaPaCa-2 cells were treated by QN523, Sulindac, phenoxybenzamine, thioridazine or prochlorperazine for 72 h and subjected to western blotting analysis of autophagy related proteins WIPI1, GABA-RAPL1 and LC3B.

Accumulation of autophagy-related markers WIPI1, GABARAPL1 and LC3B was also observed with QN523 and Sulindac in MiaPaCa-2 upon 72 h treatment (FIG. 12). Accumulation of these proteins indicated activation of autophagy in the protein level, hence validating the discovery by analysis of nascent RNA transcriptome. Among the three markers, WIPI1 showed the most significant dose-dependent induction by QN523 treatment. Significant induction of the protein was detected at concentrations as low as 0.25 μM.

Interestingly, the phenothiazine antipsychotic compounds thioridazine and prochlorperazine displayed robust activation of autophagy at their $IC_{50}$ values. Autophagy activation by the phenothiazine trifluoroperazine was identified in human glioblastoma cell line H4 through an image-based screening by detecting LC3-GFP accumulation on autophagosomal membrane (see, e.g., Zhang L, et al., (2007) Proceedings of the National Academy of Sciences of the United States of America 104(48): 19023-19028). These findings suggest a potential shared mechanism of autophagy induction by phenothiazines.

The induction of stress responses and autophagy at the protein level was successfully validated. Using Sulindac as a positive control for the proposed markers, the highly potent cellular activity of QN523 in MiaPaCa-2 was demonstrated. In addition, it was shown that the FDA-approved compounds identified by CMAP exhibited similar activation of cellular events with QN325. Collectively, such bioinformatics findings have so far demonstrated robust translation in the pancreatic cancer cell line MiaPaCa-2, supporting further evaluation of the hypothesis generated from the Bru-seq analysis.

Example XVI

This example describes the materials and methods utilized in Examples I-XV.

Compounds.

For in vitro studies, compounds were dissolved in DMSO at 10 mM as stock solutions and stored at −20° C. For in vivo studies, QN523 was dissolved in a vehicle containing 5% DMSO, 35% propylene glycol and 60% saline, and administered at 100 uL through intraperitoneal injections.

Western Blotting.

In addition, primary antibodies for LC3B, survivin, cyclin D1, Stat3 and phosphorylated Stat3 (Y705) are from Cell Signaling Technology.

Bioinformatics Analysis.

Bru-seq data from QN523 treatment (1 uM, 24 h) and vehicle controls in MiaPaCa-2 was processed by filtering for genes with RPKM>0.5, gene size >300 bp. Expressed genes were then preranked according to fold change comparing to control and subjected to analysis.

For DAVID analysis, lists of genes upregulated or downregulated by at least 2 fold with QN523 were generated, and subjected to identification of common biological themes in each list. Top functional terms identified by DAVID are reported.

For NextBio analysis, the seven marker genes were searched independently for pharmaco atlas. The top 20 correlated compounds are reported. Compounds with correlation score higher than 50 in each list were subjected to comparison among lists of the seven markers.

For connectivity map analysis, same lists for DAVID analysis were used as a pair of description for QN523 treatment and queried the CMAP database. Top 20 enriched compounds are reported.

Example XVII

This example describes synthesis techniques for generating compounds as disclosed herein.

Synthesis of Key Intermediates

8-Nitro-quinolin-6-ol (NY-1-31)

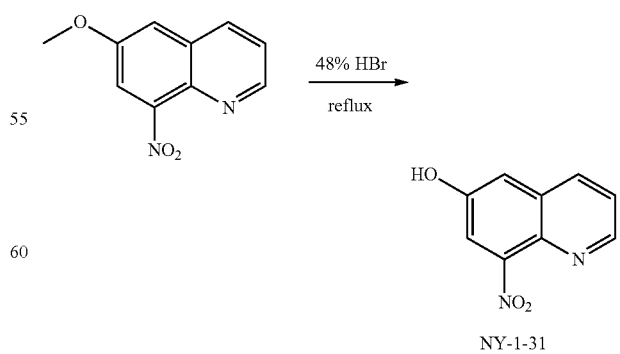

NY-1-31

6-Methoxy-8-nitro-quinoline (2.0 g) was dissolved in a mixed solution of 48% aq. HBr in HOAc (v/v 3:2) and then the reaction was refluxed at 130° C. for 2 days. The mixture was cooled to rt and filtered to provide a yellow solid, which was then dispensed in sat. NaHCO$_3$ solution (aq.) for 1 h, filtered again and dried over Na$_2$SO$_4$ to afford the desired compound NY-1-31 (1.38 g, 74%) as a light yellow solid. $^1$H NMR (300 MHz, DMSO-d$_6$) δ 10.80 (s, 1H), 8.78 (dd, J=4.2, 1.6 Hz, 1H), 8.35 (dd, J=8.5, 1.6 Hz, 1H), 7.80 (d, J=2.6 Hz, 1H), 7.59 (dd, J=8.4, 4.2 Hz, 1H), 7.45 (d, J=2.6 Hz, 1H).

6-Methoxy-quinolin-8-ylamine (NY-1-33)

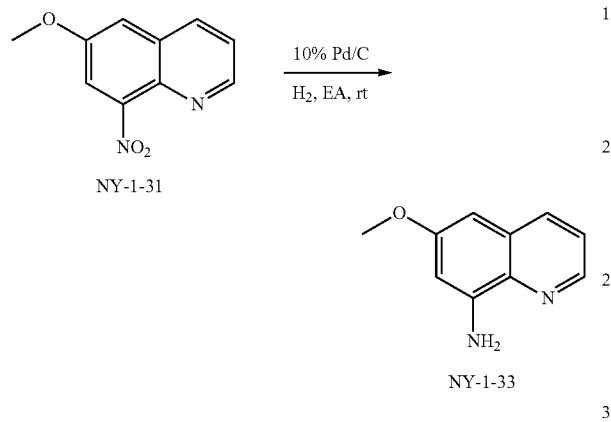

To a solution of 6-Methoxy-8-nitro-quinoline NY-1-31 (204 mg) in ethyl acetate (EA) was added 10% Pd/C (40 mg). The mixture was hydrogenated with H$_2$ under a pressure of 1.5 psi for 2 h. The mixture was filtered through a plug of celite, and the filtrate was concentrated to give the crude amine NY-1-33 (168 mg, 96%), which was directly used for the next step without further purification. $^1$H NMR (300 MHz, CDCl$_3$) δ 8.62 (dd, J=4.2, 1.7 Hz, 1H), 7.96 (dd, J=8.3, 1.6 Hz, 1H), 7.33 (dd, J=8.3, 4.2 Hz, 1H), 6.60 (d, J=2.6 Hz, 1H), 6.50 (d, J=2.6 Hz, 1H), 5.01 (s, 2H), 3.90 (d, J=0.6 Hz, 3H).

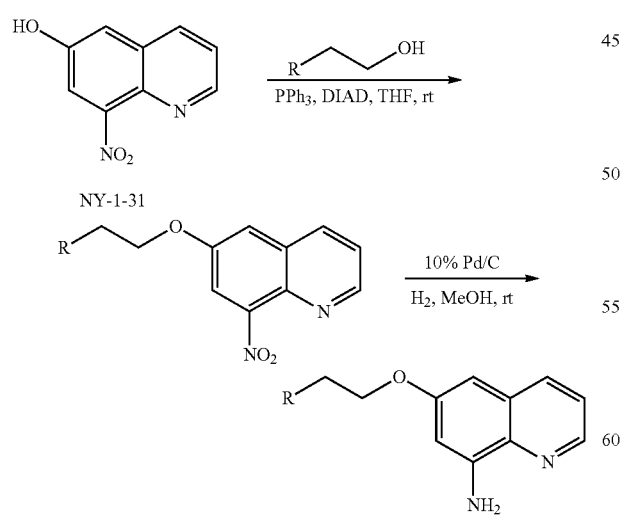

General Mitsunobu Reaction Procedure

To a solution of 8-nitro-quinolin-6-ol NY-1-31 (1.0 eq) and PPh$_3$ (1.8 eq) in THF (10 mL) was added the corresponding ethanol (1.8 eq) and DIAD (1.8 eq). The mixture was stirred at r.t. overnight. The mixture was partitioned between EtOAc (50 mL) and H$_2$O (20 mL). The organic layer was washed with brine (10 mL) and dried over Na$_2$SO$_4$, and concentrated to give the crude product. This residue was purified with silica gel column (Hexane/EtOAc) to obtain the corresponding alkylated product.

General Hydrogenation Procedure

To the solution of the corresponding alkylated product in MeOH was added 10% Pd/C. The mixture was hydrogenated with hydrogen under a pressure of 1.5 psi for 2 h. The mixture was filtered through a plug of celite, and the filtrate was concentrated to give the crude amine which was directly used for the next step without further purification.

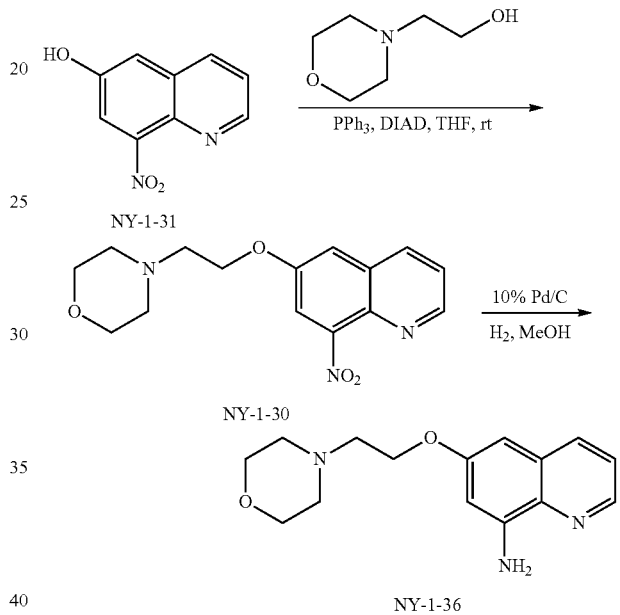

6-(2-Morpholin-4-yl-ethoxy)-8-nitro-quinoline (NY-1-30)

The title compound was prepared by reaction of 8-nitro-quinolin-6-ol NY-1-31 (50 mg, 0.26 mmol) and 2-morpholin-4-yl-ethanol (62 mg, 0.47 mmol) according to the described general Mitsunobu reaction procedure. Purification by a silica gel column (EtOAc/hexane=4:1) afforded the desired compound NY-1-30 (64 mg, yield 81%) as a colorless oil. $^1$H NMR (300 MHz, CDCl$_3$) δ 8.92 (dd, J=4.2, 1.6 Hz, 1H), 8.13 (dd, J=8.4, 1.7 Hz, 1H), 7.75 (d, J=2.7 Hz, 1H), 7.50 (dd, J=8.4, 4.2 Hz, 1H), 7.31 (d, J=2.7 Hz, 1H), 4.28 (t, J=5.6 Hz, 2H), 3.79-3.73 (m, 4H), 2.90 (t, J=5.6 Hz, 2H), 2.67-2.59 (m, 4H).

6-(2-Morpholin-4-yl-ethoxy)-quinolin-8-ylamine (NY-1-36)

The title compound was prepared by reduction of NY-1-30 (64 mg, 0.21 mmol) according to the described general hydrogenation procedure to afford the crude amine (60 mg, approximately quantitative yield) as a red oil.

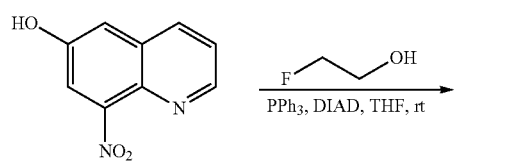

NY-1-31

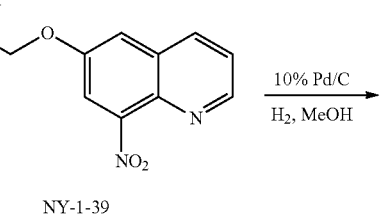

NY-1-39

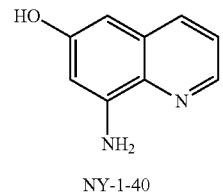

NY-1-40

The title compound was prepared by the reduction of NY-1-29 (64 mg, 0.20 mmol) according to the general hydrogenated procedure to afford the crude amine NY-1-40 (56 mg, 85%) as a red oil. $^1$H NMR (300 MHz, CDCl$_3$) δ 8.60 (dd, J=4.2, 1.7 Hz, 1H), 7.91 (dd, J=8.4, 1.6 Hz, 1H), 7.32 (dd, J=8.3, 4.2 Hz, 1H), 6.56 (d, J=2.5 Hz, 1H), 6.49 (d, J=2.6 Hz, 1H), 5.12 (s, 1H), 1.69 (s, 1H).

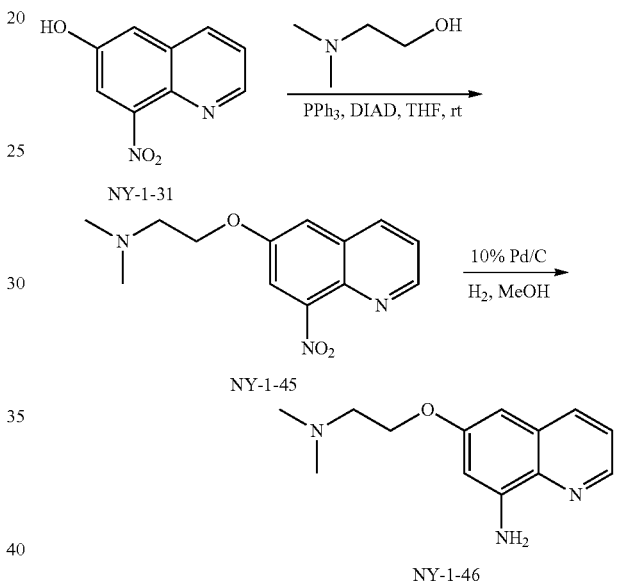

NY-1-31

NY-1-45

NY-1-46

NY-1-41

Fluoro-ethoxy)-8-nitro-quinoline (NY-1-39)

The title compound was prepared by reaction of 8-nitro-quinolin-6-ol NY-1-31 (50 mg, 0.26 mmol) and 2-fluoro-ethanol (31 mg, 0.47 mmol) according to the general Mitsunobu reaction procedure. Purification by a silica gel column (EtOAc/hexane=1:3) afforded the desired compound NY-1-39 (47 mg, 76%) as a pale yellow solid. $^1$H NMR (300 MHz, CDCl$_3$) δ 8.80 (dd, J=4.3, 1.7 Hz, 1H), 8.09 (dd, J=8.5, 1.7 Hz, 1H), 7.68 (d, J=2.8 Hz, 1H), 7.44 (dd, J=8.4, 4.2 Hz, 1H), 7.28 (d, J=2.9 Hz, 1H), 4.91-4.82 (m, 1H), 4.75-4.67 (m, 1H), 4.44-4.34 (m, 1H), 4.33-4.26 (m, 1H).

6-(2-Fluoro-ethoxy)-quinolin-8-yl amine (NY-1-41)

The title compound was prepared by reduction of NY-1-39 (47 mg, 0.20 mmol) according to the general hydrogenation procedure to afford the crude amine NY-1-41 (38 mg, 93%) as a pale yellow solid. $^1$H NMR (300 MHz, CDCl$_3$) δ 8.63 (dd, J=4.2, 1.6 Hz, 1H), 7.95 (dd, J=8.3, 1.7 Hz, 1H), 7.33 (dd, J=8.3, 4.2 Hz, 1H), 6.64 (d, J=2.5 Hz, 1H), 6.48 (d, J=2.6 Hz, 1H), 5.04 (s, 2H), 4.92-4.85 (m, 1H), 4.77-4.69 (m, 1H), 4.40-4.31 (m, 1H), 4.30-4.22 (m, 1H).

8-Amino-quinolin-6-ol (NY-1-40)

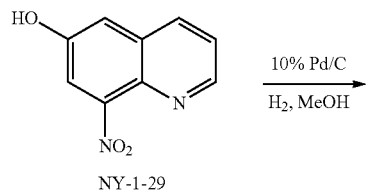

NY-1-29

Dimethyl-[2-(8-nitro-quinolin-6-yloxy)-ethyl]-amine (NY-1-45)

The title compound was prepared by the reaction of 8-nitro-quinolin-6-ol NY-1-31 (80 mg, 0.42 mmol) and 2-dimethylamino-ethanol (86 mg, 0.76 mmol) according to the general Mitsunobu reaction procedure. Purification by a silica gel column (EtOAc/hexane=4:1) afforded the desired compound NY-1-45 (88 mg, yield 81%) as a yellow oil. $^1$H NMR (300 MHz, CDCl$_3$) δ 8.87 (dd, J=4.2, 1.7 Hz, 1H), 8.11 (dd, J=8.4, 1.7 Hz, 1H), 7.73 (d, J=2.7 Hz, 1H), 7.46 (dd, J=8.4, 4.2 Hz, 1H), 7.29 (d, J=2.7 Hz, 1H), 4.22 (t, J=5.5 Hz, 2H), 2.81 (t, J=5.5 Hz, 2H), 2.36 (s, 6H).

6-(2-Dimethylamino-ethoxy)-quinolin-8-ylamine (NY-1-46)

The title compound was prepared by the reduction of NY-1-45 (88 mg, 0.33 mmol) according to general hydrogenation procedure to afford the crude amine (69 mg, yield 88%) as a brown oil.

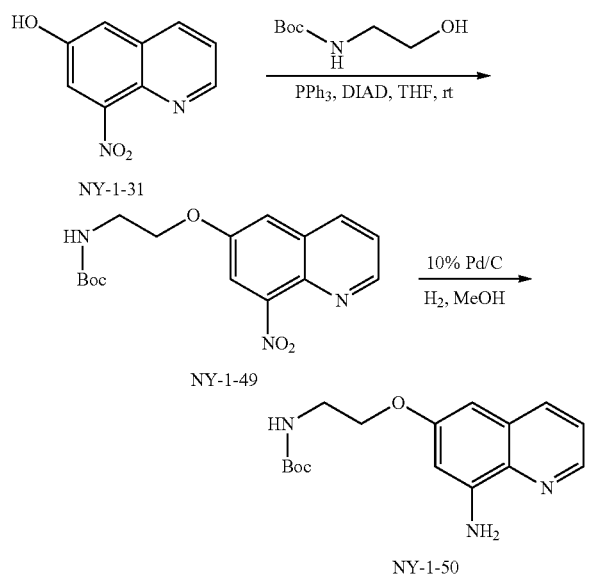

NY-1-31

NY-1-49

NY-1-50

[2-(8-Nitro-quinolin-6-yloxy)-ethyl]carbamic acid tert-butyl ester (NY-1-49)

The title compound was prepared by the reaction of 8-nitro-quinolin-6-ol NY-1-31 (150 mg, 0.79 mmol) and (2-hydroxy-ethyl)carbamic acid tert-butyl ester (258 mg, 1.59 mmol) according to the general Mitsunobu reaction procedure. Purification by a silica gel column (EtOAc/hexane=1:2) afforded the desired compound NY-1-49 (255 mg, yield 97%) as a light yellow oil. NMR (300 MHz, CDCl$_3$) δ 8.91 (s, 1H), 8.13 (d, J=8.3 Hz, 1H), 7.71 (s, 1H), 7.50 (s, 1H), 7.29 (d, J=4.1 Hz, 1H), 5.05 (s, 3H), 4.20 (t, J=4.8 Hz, 2H), 3.62 (d, J=5.0 Hz, 2H), 1.45 (s, 9H). $^{13}$C NMR (75 MHz, CDCl$_3$) δ 166.60, 155.10, 150.17, 134.94, 129.98, 123.06, 116.76, 110.20, 79.63, 43.18, 39.85, 28.36.

[2-(8-Aminoquinolin-6-yloxy)ethyl]carbamic acid tert-butyl ester (NY-1-50)

The title compound was prepared by the reduction of NY-1-49 (210 mg, 0.63 mmol) according to the general hydrogenation procedure to afford the crude amine (225 mg, yield 96%) as a yellow oil. $^1$H NMR (300 MHz, CDCl$_3$) δ 8.61 (s, 1H), 7.95 (d, J=8.4 Hz, 1H), 7.33 (s, 1H), 6.59 (s, 1H), 6.47 (s, 1H), 5.01 (s, 3H), 4.12 (s, 2H), 3.58 (s, 2H).

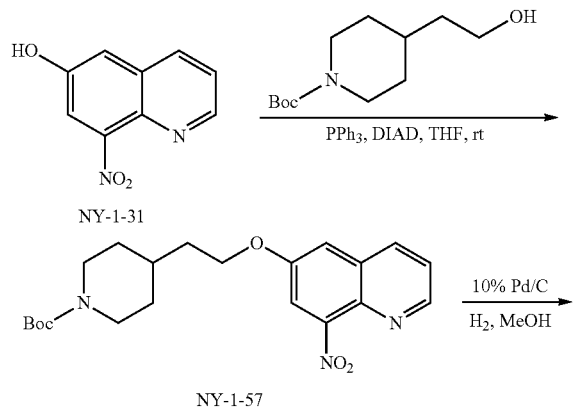

NY-1-31

NY-1-57

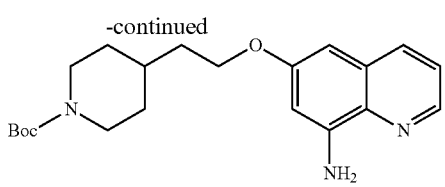

NY-1-58

4-[2-(8-Nitro-quinolin-6-yloxy)ethyl]piperidine-1-carboxylic acid tert-butyl ester (NY-1-57)

The title compound was prepared by the reaction of 8-nitro-quinolin-6-ol NY-1-31 (150 mg, 0.79 mmol) and 4-(2-hydroxyethyl)piperidine-1-carboxylic acid tert-butyl ester (325 mg, 1.42 mmol) according to the general Mitsunobu reaction procedure. Purification by a silica gel column (EtOAc/hexane=1:2) afforded the desired compound NY-1-57 (300 mg, yield 95%) as a yellow oil. $^1$H NMR (300 MHz, CDCl$_3$) δ 8.91 (dd, J=3.8, 2.0 Hz, 1H), 8.13 (dd, J=8.8, 1.9 Hz, 1H), 7.71 (d, J=2.7 Hz, 1H), 7.53-7.46 (m, 1H), 7.28 (q, J=1.6 Hz, 1H), 4.23-4.07 (m, 4H), 2.74 (t, J=13.0 Hz, 2H), 1.85-1.71 (m, 4H), 1.47 (s, 9H), 1.25 (m, 3H). $^{13}$C NMR (75 MHz, CDCl$_3$) δ 167.73, 155.48, 154.81, 149.99, 135.43, 134.78, 130.03, 122.98, 116.79, 110.05, 79.36, 66.56, 35.47, 32.95, 32.04, 28.46, 21.94.

4-[2-(8-Aminoquinolin-6-yloxy)ethyl]piperidine-1-carboxylic acid tert-butyl ester (NY-1-58)

The title compound was prepared by the reduction of NY-1-57 (300 mg, 0.75 mmol) according to general hydrogenation procedure to afford the crude amine (350 mg, approximately quantitative yield) as a brown oil. $^1$H NMR (300 MHz, CDCl$_3$) δ 8.60 (t, J=3.0 Hz, 1H), 7.97-7.90 (m, 1H), 7.36-7.30 (m, 1H), 6.58 (d, J=2.3 Hz, 1H), 6.47 (d, J=2.6 Hz, 1H), 5.09-4.91 (m, 2H), 4.11 (m, 4H), 2.71 (m, 2H), 1.80-1.72 (m, 4H), 1.48 (s, 9H), 1.30-1.26 (m, 3H). $^{13}$C NMR (75 MHz, CDCl$_3$) δ 166.60, 158.13, 154.86, 145.08, 144.98, 135.37, 134.66, 129.86, 121.78, 101.83, 95.28, 79.26, 65.33, 35.73, 33.07, 32.10, 28.47, 21.94.

General Procedure for Amidation

To a solution of the corresponding acid (1.0 to 2.0 equiv) and amine (1.0 equiv) in CH$_2$Cl$_2$ was added DIPEA (3.0 equiv). HBTU (2.0 equiv) was added at 0° C. The resulting mixture was stirred at r.t. for 24 h. The reaction mixture was diluted with CH$_2$Cl$_2$ and washed with water. The organic layer was separated and dried over anhydrous Na$_2$SO$_4$. The solution was concentrated to give a crude product, which was purified with a silica gel column (EtOAc/hexane) to obtain the desired product.

5-Methylpyrazine-2-carboxylic acid quinolin-6-ylamide (HJC-5-20)

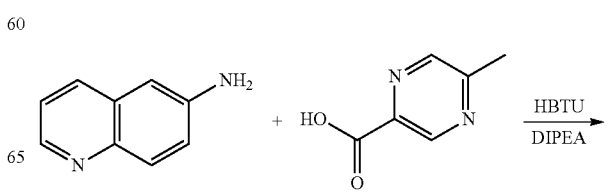

-continued

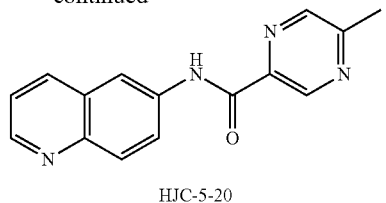

HJC-5-20

The title compound was prepared by the reaction of 5-methylpyrazine-2-carboxylic acid (69 mg, 0.5 mmol) and quinolin-6-ylamine (72 mg, 0.5 mmol) according to general procedure. Purification by a silica gel column (EtOAc/hexane=2:1) afforded the desired compound (90 mg, yield 68%) as a pale brown solid (mp 206-207° C.). HPLC purity 99.8% ($t_R$=16.97 min). $^1$H NMR (600 MHz, DMSO-$d_6$) δ 10.99 (s, 1H), 9.21 (s, 1H), 8.82 (dd, 1H, J=4.2 Hz, J=1.2 Hz), 8.73 (s, 1H), 8.64 (d, 1H, J=1.8 Hz), 8.32 (d, 1H, J=7.8 Hz), 8.19 (dd, 1H, J=9.0 Hz, J=2.4 Hz), 8.01 (d, 1H, J=9.0 Hz), 7.51 (dd, 1H, J=7.8 Hz, J=4.2 Hz), 2.65 (s, 3H). $^{13}$C NMR (150 MHz, DMSO-$d_6$) δ 162.3, 157.4, 149.5, 145.1, 143.1, 142.8, 142.2, 136.2, 135.7, 129.3, 128.1, 124.4, 121.8, 116.7, 21.5. HRMS (ESI) calcd for $C_{15}H_{13}N_4O$ 265.1084 (M+H)$^+$, found 265.1047.

5-Methylpyrazine-2-carboxylic acid quinolin-5-ylamide (HJC-5-21)

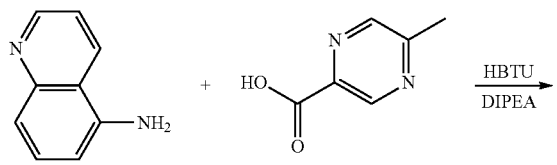

HJC-5-21

The title compound was prepared by the reaction of 5-methylpyrazine-2-carboxylic acid (69 mg, 0.5 mmol) and quinolin-5-ylamine (72 mg, 0.5 mmol) according to the general procedure. Purification by a silica gel column (EtOAc/hexane=1:1) afforded the desired compound (95 mg, yield 72%) as a pale gray solid (mp 190-191° C.). HPLC purity 99.9% ($t_R$=15.83 min). $^1$H NMR (600 MHz, DMSO-$d_6$) δ 10.99 (s, 1H), 9.18 (d, 1H, J=1.2 Hz), 8.94 (dd, 1H, J=4.2 Hz, J=1.8 Hz), 8.76 (d, 1H, J=0.6 Hz), 8.64 (d, 1H, J=8.4 Hz), 7.97 (dd, 1H, J=7.2 Hz, J=1.8 Hz), 7.19-7.83 (m, 2H), 7.56 (dd, 1H, J=8.4 Hz, J=4.2 Hz), 2.67 (s, 3H). $^{13}$C NMR (150 MHz, DMSO-$d_6$) δ 162.8, 157.4, 150.6, 148.1, 143.0, 142.9, 142.1, 133.4, 131.8, 129.0, 127.2, 123.9, 123.2, 121.2, 21.5. HRMS (ESI) calcd for $C_{15}H_{13}N_4O$ 265.1084 (M+H)$^+$, found 265.1083.

6-Methyl-N-quinolin-8-yl-nicotinamide (HJC-5-22)

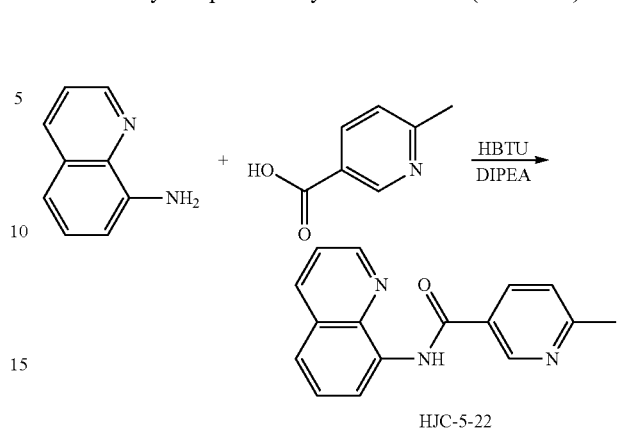

HJC-5-22

The title compound was prepared by the reaction of 6-methylnicotinic acid (69 mg, 0.5 mmol) and quinolin-8-ylamine (72 mg, 0.5 mmol) according to general procedure. Purification by a silica gel column (EtOAc/hexane=1:1) afforded the desired compound (90 mg, yield 68%) as a pale gray solid (mp 128-129° C.). HPLC purity 99.9% ($t_R$=19.88 min). $^1$H NMR (600 MHz, CDCl$_3$) δ 10.75 (s, 1H), 9.22 (d, 1H, J=2.4 Hz), 8.90 (dd, 1H, J=7.2 Hz, J=1.2 Hz), 8.84 (dd, 1H, J=7.2 Hz, J=1.2 Hz), 8.26 (dd, 1H, J=8.4 Hz, J=2.4 Hz), 8.20 (dd, 1H, J=8.4 Hz, J=1.8 Hz), 7.56-7.61 (m, 2H), 7.49 (dd, 1H, J=7.8 Hz, J=4.8 Hz), 7.33 (d, 1H, J=7.8 Hz), 2.67 (s, 3H). $^{13}$C NMR (150 MHz, CDCl$_3$) δ 163.9, 162.3, 148.5, 148.2, 138.8, 136.6, 135.6, 134.4, 128.2, 128.1, 127.6, 123.4, 122.1, 122.0, 116.8, 24.8. HRMS (ESI) calcd for $C_{16}H_{14}N_3O$ 264.1131 (M+H)$^+$, found 264.1181.

Pyrazine-2-carboxylic acid quinolin-8-ylamide (HJC-5-23)

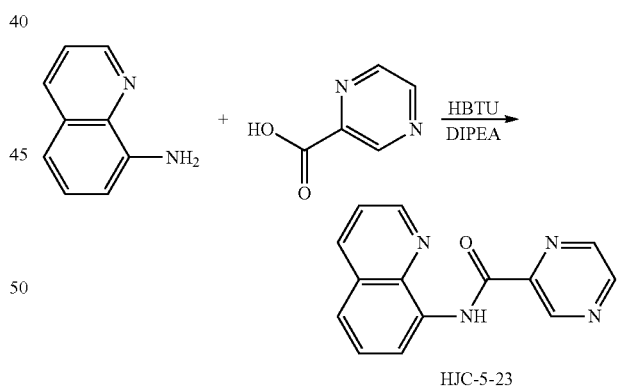

HJC-5-23

The title compound was prepared by the reaction of pyrazine-2-carboxylic acid (62 mg, 0.5 mmol) and quinolin-8-ylamine (72 mg, 0.5 mmol) according to general procedure. Purification by silica gel column (EtOAc/hexane=1:1) afforded the desired compound (88 mg, yield 70%) as a pale yellow solid (mp 189-190° C.). HPLC purity 99.4% ($t_R$=19.83 min). $^1$H NMR (600 MHz, CDCl$_3$) δ 12.06 (s, 1H), 9.57 (d, 1H, J=1.2 Hz), 8.99 (dd, 1H, J=6.6 Hz, J=1.8 Hz), 8.95 (dd, 1H, J=4.2 Hz, J=1.8 Hz), 8.82 (d, 1H, J=2.4 Hz), 8.75 (dd, 1H, J=2.4 Hz, J=1.8 Hz), 8.20 (dd, 1H, J=8.4 Hz, J=1.8 Hz), 7.59-7.64 (m, 2H), 7.50 (dd, 1H, J=8.4 Hz, J=4.2 Hz). $^{13}$C NMR (150 MHz, CDCl$_3$) δ 161.4, 149.0, 147.5, 145.4, 144.8, 143.0, 139.4, 136.5, 134.1, 128.3, 127.5, 122.7, 121.9, 117.2. HRMS (ESI) calcd for $C_{14}H_{11}N_4O$ 251.0927 (M+H)⁺, found 251.0935.

6-Bromo-N-quinolin-8-yl-nicotinamide (HJC-5-24)

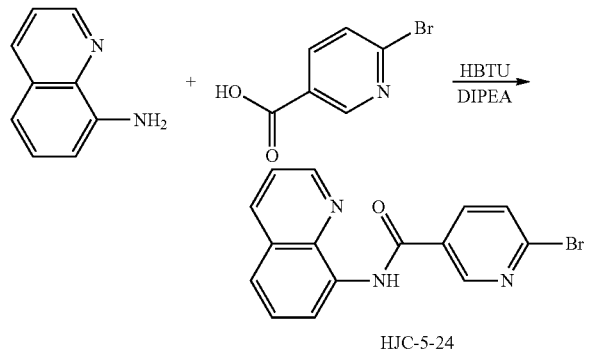

HJC-5-24

The title compound was prepared by reaction of 6-bromonicotinic acid (101 mg, 0.5 mmol) and quinolin-8-ylamine (72 mg, 0.5 mmol) according to the general procedure. Purification by a silica gel column (EtOAc/hexane/CH₂Cl₂=1:3:1) afforded the desired compound (50 mg, yield 31%) as a pale gray solid (mp 168-169° C.). HPLC purity 98.9% ($t_R$=21.22 min). ¹H NMR (600 MHz, CDCl₃) δ 10.76 (s, 1H), 9.07 (d, 1H, J=2.4 Hz), 8.85-8.88 (m, 2H), 8.21-8.23 (m, 2H), 7.68 (d, 1H, J=3.6 Hz), 7.59-7.63 (m, 2H), 7.51 (dd, 1H, J=8.4 Hz, J=4.2 Hz). ¹³C NMR (150 MHz, CDCl₃) δ 162.7, 149.1, 148.7, 145.7, 138.8, 137.6, 136.7, 134.0, 130.3, 128.5, 128.1, 127.6, 122.6, 122.1, 117.0. HRMS (ESI) calcd for $C_{15}H_{11}BrN_3O$ 328.0080 (M+H)⁺, found 328.0091.

5-Bromopyridine-2-carboxylic acid quinolin-8-ylamide (HJC-5-29)

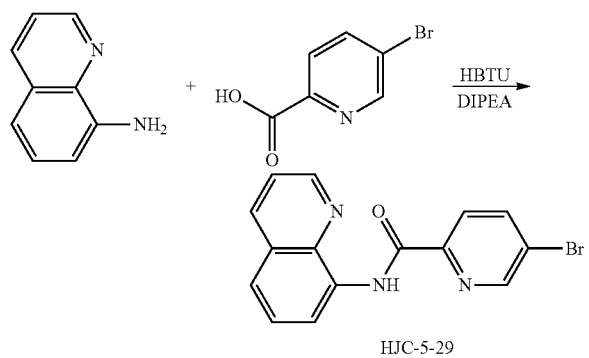

HJC-5-29

The title compound was prepared by the reaction of 5-bromopyridine-2-carboxylic acid (152 mg, 0.75 mmol) and quinolin-8-ylamine (72 mg, 0.5 mmol) according to the general procedure. Purification by a silica gel column (EtOAc/hexane/CH₂Cl₂=1:3:1) afforded the desired compound (120 mg, yield 73%) as a pale yellow solid (mp 170-171° C.). HPLC purity 98.9% ($t_R$=23.43 min). ¹H NMR (600 MHz, CDCl₃) δ 12.14 (s, 1H), 8.95-8.98 (m, 2H), 8.84 (d, 1H, J=2.4 Hz), 8.24 (d, 1H, J=8.4 Hz), 8.19 (dd, 1H, J=8.4 Hz, J=1.8 Hz), 8.06 (dd, 1H, J=8.4 Hz, J=2.4 Hz), 7.57-7.62 (m, 2H), 7.49 (dd, 1H, J=7.8 Hz, J=3.6 Hz). ¹³C NMR (150 MHz, CDCl₃) δ 162.1, 149.9, 149.2, 148.9, 140.3, 139.4, 136.4, 134.4, 128.3, 127.4, 124.3, 124.0, 122.4, 121.9, 117.0. HRMS (ESI) calcd for $C_{15}H_{11}BrN_3O$ 328.0080 (M+H)⁺, found 328.0079.

6-Bromopyridine-2-carboxylic acid quinolin-8-ylamide (HJC-5-30)

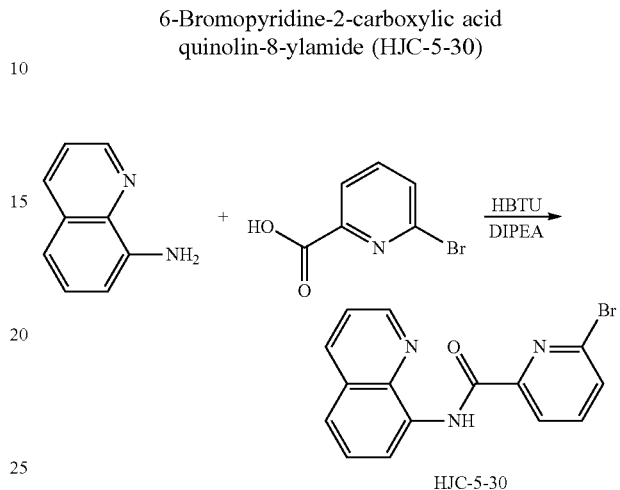

HJC-5-30

The title compound was prepared by the reaction of 6-bromopyridine-2-carboxylic acid (152 mg, 0.75 mmol) and quinolin-8-ylamine (72 mg, 0.5 mmol) according to the general procedure. Purification by a silica gel column (EtOAc/hexane=1:1) afforded the desired compound (125 mg, yield 76%) as a pale yellow solid (mp 135-136° C.). HPLC purity 99.1% ($t_R$=22.96 min). ¹H NMR (600 MHz, CDCl₃) δ 12.05 (s, 1H), 8.94-8.98 (m, 2H), 8.30 (d, 1H, J=7.2 Hz), 8.18 (dd, 1H, J=8.4 Hz, J=1.2 Hz), 7.78 (t, 1H, J=7.8 Hz), 7.69 (d, 1H, J=7.8 Hz), 7.56-7.61 (m, 2H), 7.49 (dd, 1H, J=8.4 Hz, J=4.2 Hz). ¹³C NMR (150 MHz, CDCl₃) δ 161.3, 151.8, 149.0, 141.0, 139.9, 139.5, 136.3, 134.3, 131.1, 128.2, 127.3, 122.5, 121.9, 121.6, 117.1. HRMS (ESI) calcd for $C_{15}H_{11}BrN_3O$ 328.0080 (M+H)⁺, found 328.0093.

6-Fluoro-N-quinolin-8-yl-nicotinamide (HJC-5-32)

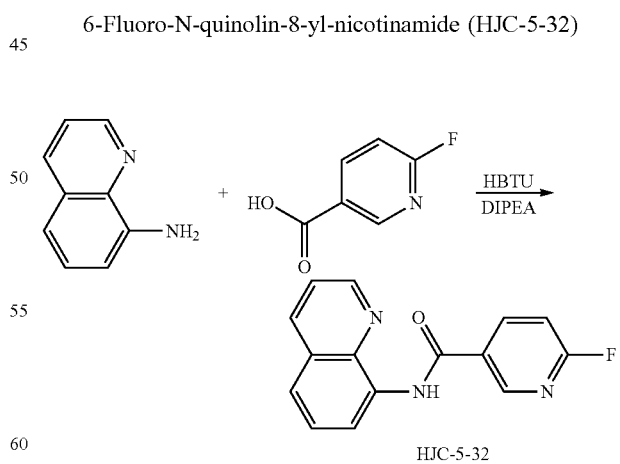

HJC-5-32

The title compound was prepared by the reaction of 6-fluoronicotinic acid (106 mg, 0.75 mmol) and quinolin-8-ylamine (72 mg, 0.5 mmol) according to general procedure. Purification by a silica gel column (EtOAc/hexane=1:3) afforded the desired compound (70 mg, yield 52%) as a pale gray solid (mp 133-134° C.). HPLC purity 95.3% ($t_R$=19.99 min). $^1$H NMR (600 MHz, CDCl$_3$) δ 10.69 (s, 1H), 8.93 (d, 1H, J=2.4 Hz), 8.81-8.85 (m, 2H), 8.44-8.47 (m, 1H), 8.17 (dd, 1H, J=8.4 Hz, J=1.8 Hz), 7.54-7.58 (m, 2H), 7.47 (dd, 1H, J=8.4 Hz, J=4.2 Hz), 7.08 (dd, 1H, J=8.4 Hz, J=2.4 Hz). $^{13}$C NMR (150 MHz, CDCl$_3$) δ 165.3 (d, J=242.6 Hz), 162.4, 148.6, 147.5 (d, J=15.9 Hz), 140.9 (d, J=8.9 Hz), 138.7, 136.6, 134.0, 129.2 (d, J=4.5 Hz), 128.0, 127.4, 122.4, 122.0, 116.8, 110.0 (d, J=37.4 Hz). HRMS (ESI) calcd for C$_{15}$H$_{11}$FN$_3$O 268.0881 (M+H)$^+$, found 268.0882.

Pyridazine-3-carboxylic acid quinolin-8-ylamide (HJC-5-66)

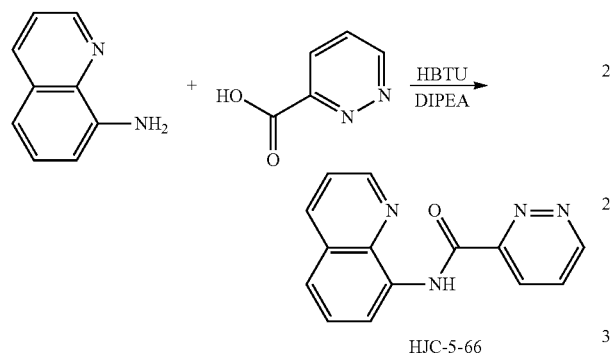

The title compound was prepared by the reaction of pyridazine-3-carboxylic acid (62 mg, 0.5 mmol) and quinolin-8-ylamine (72 mg, 0.5 mmol) according to the general procedure. Purification by a silica gel column (EtOAc/hexane=1:1) afforded the desired compound (100 mg, yield 80%) as a white solid (mp 181-182° C.). HPLC purity 98.8% ($t_R$=19.24 min). $^1$H NMR (600 MHz, CDCl$_3$) δ 12.47 (s, 1H), 9.38 (d, 1H, J=4.2 Hz), 8.96-8.98 (m, 2H), 8.48 (dd, 1H, J=8.4 Hz, J=1.2 Hz), 8.20 (d, 1H, J=8.4 Hz), 7.75 (dd, 1H, J=8.4 Hz, J=4.8 Hz), 7.61-7.62 (m, 2H), 7.50 (dd, 1H, J=7.8 Hz, J=4.8 Hz). $^{13}$C NMR (150 MHz, CDCl$_3$) δ 160.8, 153.4, 152.9, 148.9, 139.3, 136.1, 134.1, 128.1, 127.7, 127.2, 125.8, 122.7, 121.9, 117.1. HRMS (ESI) calcd for C$_{14}$H$_{11}$N$_4$O 251.0927 (M+H)$^+$, found 251.0936.

Pyrimidine-2-carboxylic acid quinolin-8-ylamide (HJC-5-67)

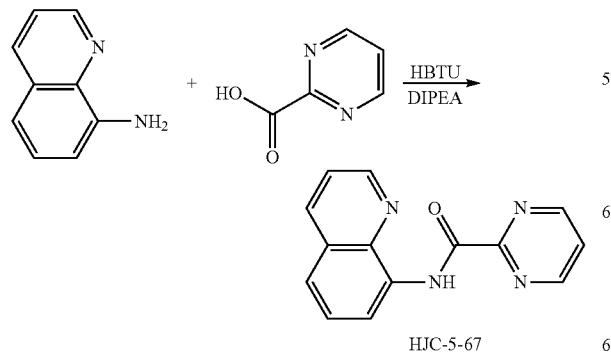

The title compound was prepared by the reaction of pyrimidine-2-carboxylic acid (62 mg, 0.5 mmol) and quinolin-8-ylamine (72 mg, 0.5 mmol) according to the general procedure. Purification by a silica gel column (EtOAc/hexane=1:1) afforded the desired compound (90 mg, yield 72%) as a pale yellow solid (mp 213-214° C.). HPLC purity 98.8% ($t_R$=18.17 min). $^1$H NMR (600 MHz, CDCl$_3$) δ 12.25 (s, 1H), 9.08 (dd, 1H, J=4.8 Hz, J=1.2 Hz), 9.03 (t, 1H, J=4.8 Hz), 8.94 (dd, 1H, J=4.2 Hz, J=1.2 Hz), 8.20 (dd, 1H, J=8.4 Hz, J=1.2 Hz), 7.58-7.64 (m, 2H), 7.48-7.52 (m, 2H). $^{13}$C NMR (150 MHz, CDCl$_3$) δ 160.3, 158.4, 157.9, 148.9, 139.3, 136.5, 134.3, 128.2, 127.6, 122.7, 122.6, 121.8, 117.5. HRMS (ESI) calcd for C$_{14}$H$_{11}$N$_4$O 251.0927 (M+H)$^+$, found 251.0927.

5-Methylpyrazine-2-carboxylic acid (5-bromoquinolin-8-yl)amide (HJC-5-71)

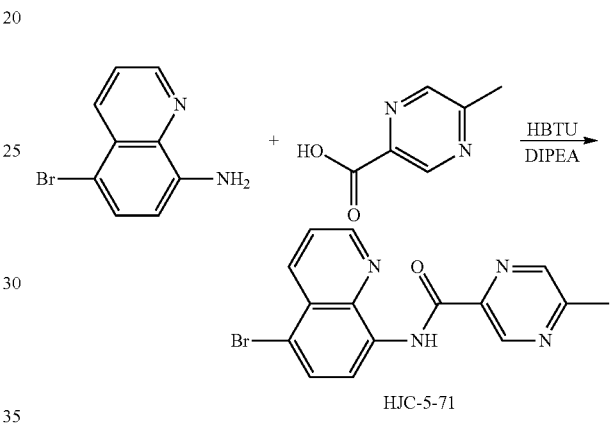

The title compound was prepared by the reaction of 5-methylpyrazine-2-carboxylic acid (25 mg, 0.18 mmol) and 5-bromoquinolin-8-ylamine (40 mg, 0.18 mmol) according to the general procedure. Purification by a silica gel column (EtOAc/hexane=1:3) afforded the desired compound (40 mg, yield 65%) as a pale gray solid (mp 218-219° C.). HPLC purity 99.4% ($t_R$=23.74 min). $^1$H NMR (600 MHz, CDCl$_3$) δ 11.98 (s, 1H), 9.41 (d, 1H, J=1.2 Hz), 8.96 (dd, 1H, J=3.6 Hz, J=1.2 Hz), 8.87 (d, 1H, J=8.4 Hz), 8.59 (s, 1H), 8.56 (dd, 1H, J=8.4 Hz, J=1.2 Hz), 7.87 (d, 1H, J=8.4 Hz), 7.60 (dd, 1H, J=8.4 Hz, J=4.8 Hz), 2.71 (s, 3H). $^{13}$C NMR (150 MHz, CDCl$_3$) δ 161.9, 157.5, 149.3, 143.8, 142.8, 142.4, 140.0, 136.1, 134.2, 131.0, 127.5, 122.9, 117.5, 115.3, 22.1. HRMS (ESI) calcd for C$_{15}$H$_{12}$BrN$_4$O 343.0189 (M+H)$^+$, found 343.0137.

Quinoxaline-2-carboxylic acid quinolin-8-ylamide (HJC-5-72)

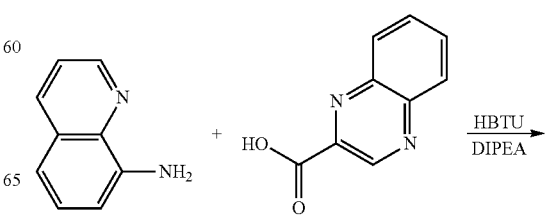

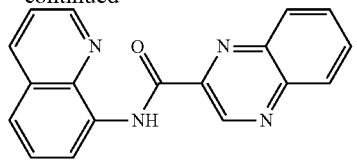

HJC-5-72

The title compound was prepared by the reaction of quinoxaline-2-carboxylic acid (44 mg, 0.25 mmol) and quinolin-8-ylamine (36 mg, 0.25 mmol) according to the general procedure. Purification by a silica gel column (EtOAc/hexane=1:7) afforded the desired compound (45 mg, yield 60%) as a yellow solid (mp 190-191° C.). HPLC purity 97.8% ($t_R$=23.18 min). $^1$H NMR (600 MHz, CDCl$_3$) δ 12.24 (s, 1H), 9.83 (s, 1H), 9.03 (dd, 1H, J=7.8 Hz, J=1.2 Hz), 9.00 (dd, 1H, J=4.2 Hz, J=1.2 Hz), 8.38-8.40 (m, 1H), 8.21-8.24 (m, 1H), 7.90-7.93 (m, 2H), 7.60-7.66 (m, 2H), 7.52 (dd, 1H, J=8.4 Hz, J=4.2 Hz). $^{13}$C NMR (150 MHz, CDCl$_3$) δ 161.8, 149.0, 144.3, 144.1, 140.6, 139.5, 136.5, 134.3, 131.9, 131.0, 130.4, 129.6, 128.3, 127.5, 122.7, 121.9, 117.3. HRMS (ESI) calcd for $C_{18}H_{13}N_4O$ 301.1084 (M+H)$^+$, found 301.1069.

5-Chloropyrazine-2-carboxylic acid quinolin-8-ylamide (HJC-5-73)

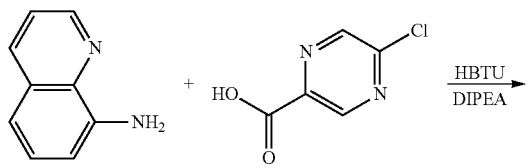

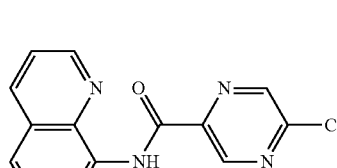

HJC-5-73

The title compound was prepared by the reaction of 5-chloropyrazine-2-carboxylic acid (40 mg, 0.25 mmol) and quinolin-8-ylamine (36 mg, 0.25 mmol) according to the general procedure. Purification by a silica gel column (EtOAc/hexane=1:7) afforded the desired compound (50 mg, yield 70%) as a white solid (mp 186-187° C.). HPLC purity 99.8% ($t_R$=22.03 min). $^1$H NMR (600 MHz, CDCl$_3$) δ 11.94 (s, 1H), 9.32 (d, 1H, J=1.2 Hz), 8.96 (dd, 1H, J=6.0 Hz, J=2.4 Hz), 8.94 (dd, 1H, J=4.2 Hz, J=1.8 Hz), 8.73 (d, 1H, J=1.2 Hz), 8.21 (dd, 1H, J=8.4 Hz, J=1.8 Hz), 7.60-7.63 (m, 2H), 7.51 (dd, 1H, J=8.4 Hz, J=4.2 Hz). $^{13}$C NMR (150 MHz, CDCl$_3$) δ 160.5, 152.3, 149.0, 144.4, 143.6, 143.0, 139.3, 136.5, 133.9, 128.3, 127.4, 122.9, 122.0, 117.3. HRMS (ESI) calcd for $C_{14}H_{10}ClN_4O$ 285.0538 (M+H)$^+$, found 285.0537.

Pyrazine-2-carboxylic acid (5-bromoquinolin-8-yl)amide (HJC-6-18)

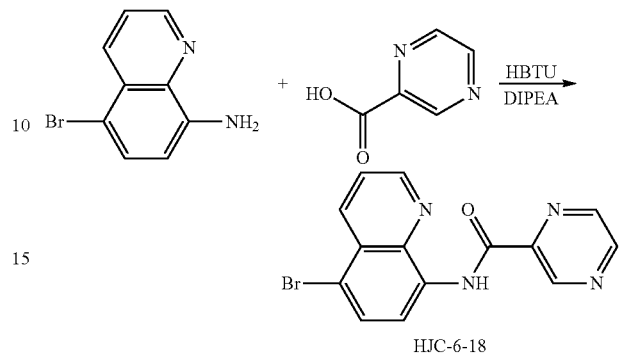

HJC-6-18

The title compound was prepared by the reaction of pyrazine-2-carboxylic acid (37 mg, 0.3 mmol) and 5-bromoquinolin-8-ylaminene (56 mg, 0.25 mmol) according to the general procedure. Purification by a silica gel column (EtOAc/hexane=1:1) afforded the desired compound (50 mg, yield 61%) as a yellow solid (mp 215-216° C.). HPLC purity 96.7% ($t_R$=22.86 min). $^1$H NMR (600 MHz, CDCl$_3$) δ 12.04 (s, 1H), 9.56 (d, 1H, J=0.6 Hz), 8.97 (dd, 1H, J=4.2 Hz, J=1.2 Hz), 8.88 (d, 1H, J=8.4 Hz), 8.83 (d, 1H, J=2.4 Hz), 8.74 (dd, 1H, J=2.4 Hz, J=1.2 Hz), 8.56 (dd, 1H, J=2.4 Hz, J=1.2 Hz), 7.88 (d, 1H, J=9.0 Hz), 7.61 (dd, 1H, J=9.0 Hz, J=4.2 Hz). $^{13}$C NMR (150 MHz, CDCl$_3$) δ 161.5, 149.4, 147.6, 145.1, 144.9, 143.1, 140.0, 136.1, 134.1, 131.0, 127.6, 123.0, 117.6, 115.5. HRMS (ESI) calcd for $C_{14}H_{10}BrN_4O$ 329.0032 (M+H)$^+$, found 329.0051.

5-Methylpyrazine-2-carboxylic acid (2-methylquinolin-8-yl)amide (HJC-6-32)

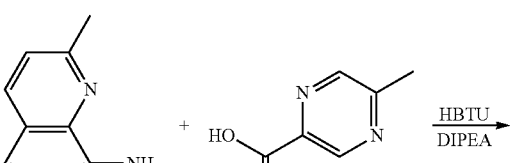

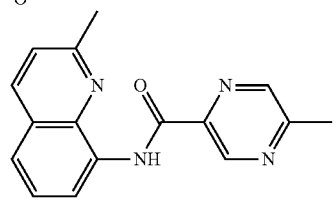

HJC-6-32

The title compound was prepared by the reaction of 5-methylpyrazine-2-carboxylic acid (38 mg, 0.28 mmol) and 2-methylquinolin-8-ylamine (36 mg, 0.25 mmol) according to the general procedure. Purification by a silica gel column (EtOAc/hexane=1:3) afforded the desired compound (60 mg, yield 86%) as a pale yellow solid (mp 168-169° C.). HPLC purity 99.2% ($t_R$=21.90 min). $^1$H NMR (600 MHz, CDCl$_3$) δ 12.04 (s, 1H), 9.42 (s, 1H), 8.94 (dd, 1H, J=5.4 Hz, J=3.6 Hz), 8.59 (s, 1H), 8.06 (d, 1H, J=8.4 Hz), 7.53 (d, 1H, J=3.6 Hz), 7.35 (d, 1H, J=8.4 Hz), 2.82 (s, 3H), 2.70 (s, 3H). $^{13}$C NMR (150 MHz, CDCl$_3$) δ 161.8, 157.8, 157.2, 143.8, 142.9, 142.8, 138.7, 136.5, 133.7, 126.4, 126.3, 122.7, 122.2, 117.1, 25.6, 22.0. HRMS (ESI) calcd for C$_{16}$H$_{15}$N$_4$O 279.1240 (M+H)$^+$, found 279.1267.

Pyrazine-2-carboxylic acid (2-methylquinolin-8-yl)amide (HJC-6-34)

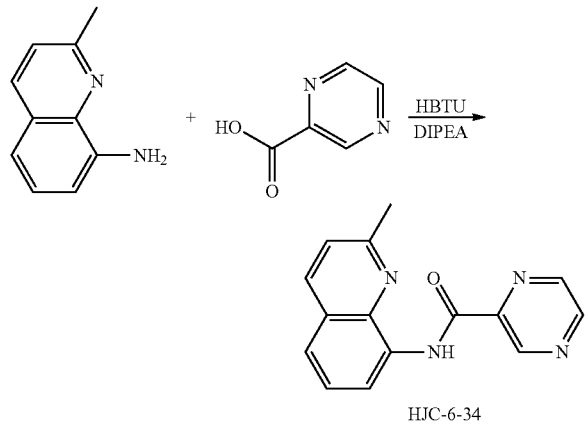

HJC-6-34

The title compound was prepared by the reaction of pyrazine-2-carboxylic acid (74 mg, 0.6 mmol) and 2-methylquinolin-8-ylamine (80 mg, 0.5 mmol) according to the general procedure. Purification by a silica gel column (EtOAc/hexane=1:1) afforded the desired compound (128 mg, yield 97%) as a pale yellow solid (mp 140-141° C.). HPLC purity 98.6% (t$_R$=21.10 min). $^1$H NMR (600 MHz, CDCl$_3$) δ 12.08 (s, 1H), 9.55 (s, 1H), 8.93-8.94 (m, 1H), 8.80 (d, 1H, J=0.6 Hz), 8.71-8.72 (m, 1H), 8.05 (d, 1H, J=3.6 Hz), 7.52 (d, 2H, J=4.2 Hz), 7.34 (d, 1H, J=8.4 Hz), 2.82 (s, 3H). $^{13}$C NMR (150 MHz, CDCl$_3$) δ 161.4, 157.8, 147.3, 145.5, 144.8, 143.0, 138.7, 136.5, 133.5, 126.3, 122.7, 122.4, 117.2, 25.6. HRMS (ESI) calcd for C$_{15}$H$_{13}$N$_4$O 265.1084 (M+H)$^+$, found 265.1083.

Pyrazine-2-carboxylic acid (6-fluoro-quinolin-8-yl)amide (HJC-6-51)

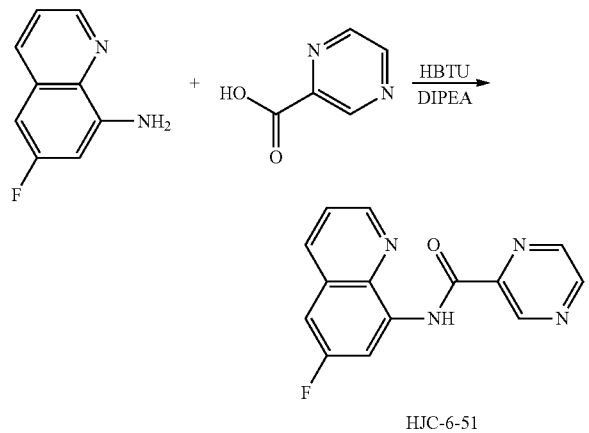

HJC-6-51

The title compound was prepared by the reaction of pyrazine-2-carboxylic acid (23 mg, 0.19 mmol) and 6-fluoroquinolin-8-ylamine (see, e.g., Gershon, H.; et al., Monatshefte fuer Chemie 2002, 133, 1437-1442) (20 mg, 0.12 mmol) according to the general procedure. Purification by a silica gel column (EtOAc/hexane=1:3) afforded the desired compound (22 mg, yield 66%) as a white solid (mp 184-185° C.). HPLC purity 99.9% (t$_R$=21.00 min). $^1$H NMR (600 MHz, CDCl$_3$) δ 12.07 (s, 1H), 9.56 (d, 1H, J=1.2 Hz), 8.89 (dd, 1H, J=4.2 Hz, J=1.2 Hz), 8.83 (d, 1H, J=2.4 Hz), 8.81 (dd, 1H, J=10.8 Hz, J=2.4 Hz), 8.75 (dd, 1H, J=2.4 Hz, J=1.8 Hz), 8.13 (dd, 1H, J=8.4 Hz, J=1.2 Hz), 7.51 (dd, 1H, J=8.4 Hz, J=4.2 Hz), 7.20 (dd, 1H, J=9.0 Hz, J=2.4 Hz). $^{13}$C NMR (150 MHz, CDCl$_3$) δ 161.7, 161.6, 160.1, 148.0, 147.7, 144.9, 143.1, 136.6, 136.0, 128.8, 128.7, 122.8, 108.1 107.9, 105.5, 105.3. HRMS (ESI) calcd for C$_{14}$H$_{10}$FN$_4$O 269.0833 (M+H)$^+$, found 269.0842.

5-Methylpyrazine-2-carboxylic acid (6-fluoroquinolin-8-yl)amide (HJC-6-52)

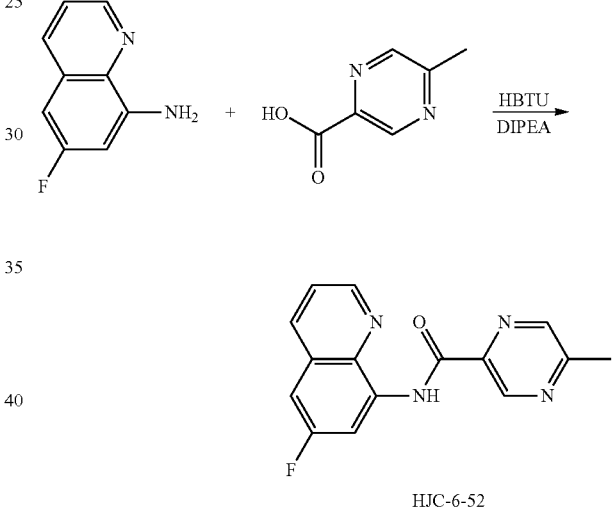

HJC-6-52

The title compound was prepared by the reaction of 5-methylpyrazine-2-carboxylic acid (26 mg, 0.19 mmol) and 6-fluoroquinolin-8-ylamine (20 mg, 0.12 mmol) according to the general procedure. Purification by a silica gel column (EtOAc/hexane=1:3) afforded the desired compound (25 mg, yield 74%) as a yellow solid (mp 183-184° C.). HPLC purity 98.1% (t$_R$=21.76 min). $^1$H NMR (600 MHz, CDCl$_3$) δ 12.00 (s, 1H), 9.40 (d, 1H, J=1.2 Hz), 8.87 (dd, 1H, J=4.2 Hz, J=1.2 Hz), 8.80 (dd, 1H, J=5.4 Hz, J=2.4 Hz), 8.58 (dd, 1H, J=1.8 Hz, J=0.6 Hz), 8.11 (dd, 1H, J=8.4 Hz, J=1.8 Hz), 7.49 (dd, 1H, J=7.8 Hz, J=4.2 Hz), 7.17 (dd, 1H, J=8.4 Hz, J=2.4 Hz), 2.70 (s, 3H). $^{13}$C NMR (150 MHz, CDCl$_3$) δ 162.0, 161.8, 160.1, 157.7, 147.9, 143.8, 142.8, 142.2, 136.6, 136.0, 135.9, 135.8, 135.8, 128.7, 128.6, 122.8, 107.9, 107.7, 105.2, 105.1, 22.1. HRMS (ESI) calcd for C$_{15}$H$_{12}$FN$_4$O 283.0990 (M+H)$^+$, found 283.1000.

Pyrazine-2-carboxylic acid [1,7]naphthyridin-8-ylamide (HJC-6-55)

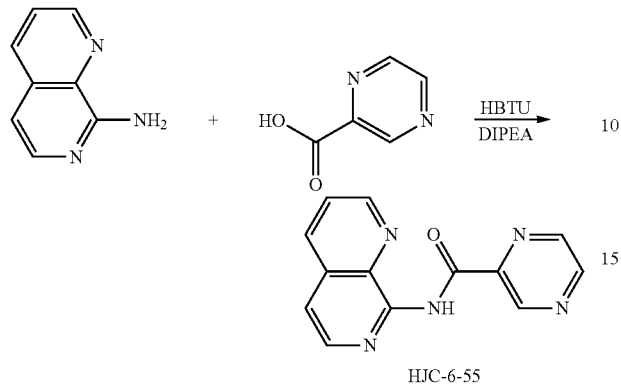

HJC-6-55

The title compound was prepared by the reaction of pyrazine-2-carboxylic acid (74 mg, 0.6 mmol) and [1,7]naphthyridin-8-ylamine (44 mg, 0.3 mmol) according to the general procedure. Purification by a silica gel column (EtOAc/hexane=1:1) afforded the desired compound (60 mg, yield 80%) as a gray solid (mp 241-242° C.). HPLC purity 99.4% ($t_R$=15.51 min). $^1$H NMR (600 MHz, CDCl$_3$) δ 12.33 (s, 1H), 9.64 (s, 1H), 9.03 (dd, 1H, J=4.2 Hz, J=1.2 Hz), 8.87 (d, 1H, J=2.4 Hz), 8.77 (dd, 1H, J=3.6 Hz, J=1.2 Hz), 8.55 (d, 1H, J=5.4 Hz), 8.20 (d, 2H, J=8.4 Hz), 7.70 (dd, 1H, J=8.4 Hz, J=4.2 Hz), 7.44 (d, 1H, J=6.0 Hz), 2.67 (s, 3H). $^{13}$C NMR (150 MHz, CDCl$_3$) δ 160.3, 150.3, 149.9, 147.8, 145.4, 145.0, 142.9, 142.7, 135.3, 134.7, 131.8, 126.0, 115.9. HRMS (ESI) calcd for C$_{13}$H$_{10}$N$_5$O 252.0880 (M+H)$^+$, found 252.0889.

Pyrimidine-2-carboxylic acid (6-fluoroquinolin-8-yl)amide (HJC-6-58)

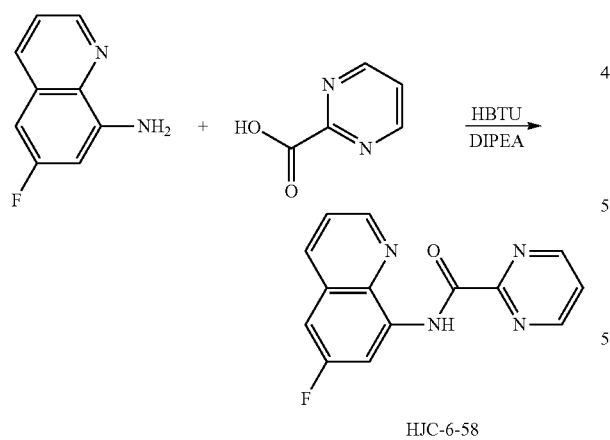

HJC-6-58

The title compound was prepared by the reaction of pyrimidine-2-carboxylic acid (62 mg, 0.5 mmol) and 6-fluoroquinolin-8-ylamine (40 mg, 0.25 mmol) according to the general procedure. Purification by a silica gel column (EtOAc/hexane=1:3) afforded the desired compound (65 mg, yield 97%) as a white solid (mp 210-211° C.). HPLC purity 99.5% ($t_R$=19.08 min). $^1$H NMR (600 MHz, CDCl$_3$) δ 12.23 (s, 1H), 9.01-9.03 (m, 2H), 8.87 (d, 1H, J=3.0 Hz), 8.85-8.86 (m, 1H), 8.09 (dd, 1H, J=8.4 Hz, J=1.8 Hz), 7.52 (t, 1H, J=4.8 Hz), 7.47 (dd, 1H, J=7.8 Hz, J=4.2 Hz), 7.16 (dd, 1H, J=9.0 Hz, J=3.0 Hz). $^{13}$C NMR (150 MHz, CDCl$_3$) δ 161.8, 160.4, 160.1, 157.9, 147.9, 136.4, 136.0, 135.9, 135.8, 135.8, 128.7, 128.6, 122.9, 122.7, 108.2, 107.9, 105.4, 105.3. HRMS (ESI) calcd for C$_{14}$H$_{10}$FN$_4$O 269.0833 (M+H)$^+$, found 269.0843.

Pyrazine-2-carboxylic acid (2-dimethylaminomethyl-quinolin-8-yl)amide (HJC-6-59)

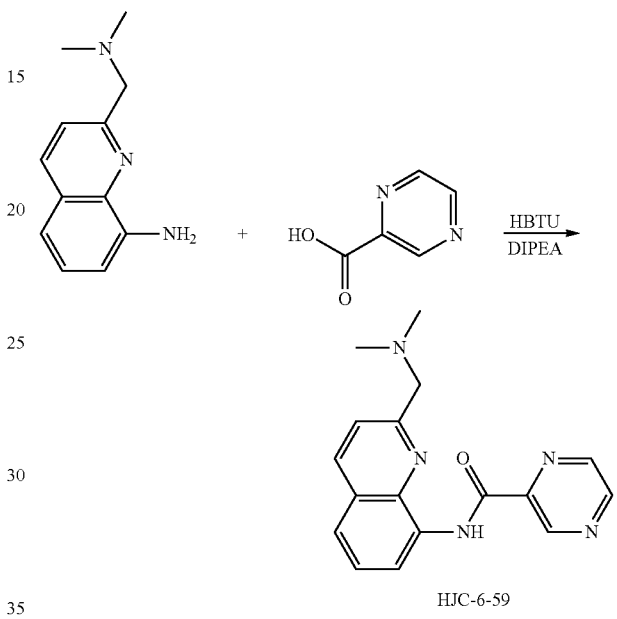

HJC-6-59

The title compound was prepared by the reaction of pyrazine-2-carboxylic acid (15 mg, 0.12 mmol) and 2-dimethylaminomethyl-quinolin-8-ylamine (see, e.g., Kim, Y. H.; et al., Bull. Korean Chem. Soc. 2005, 26, 47-50; Xue, G.; et al., Tetrahedron 2001, 57, 7623-7628) (20 mg, 0.1 mmol) according to the general procedure. Purification by a silica gel column (EtOAc/hexane=2:1) afforded the desired compound (25 mg, yield 82%) as a white solid (mp 249-250° C.). HPLC purity 98.9% ($t_R$=15.11 min). $^1$H NMR (600 MHz, acetone-d$_6$) δ 11.89 (s, 1H), 9.44 (s, 1H), 9.00 (d, 1H, J=7.8 Hz), 8.97 (d, 1H, J=1.8 Hz), 8.93 (d, 1H, J=1.2 Hz), 8.58 (d, 1H, J=8.4 Hz), 7.75-7.84 (m, 3H), 5.15 (s, 2H), 3.58 (s, 6H). $^{13}$C NMR (150 MHz, acetone-d$_6$) δ 161.9, 151.2, 149.1, 145.5, 145.0, 144.3, 139.5, 138.6, 134.7, 128.9, 128.7, 123.6, 122.4, 118.4, 62.0, 45.5. HRMS (ESI) calcd for C$_{17}$H$_{18}$N$_5$O 308.1506 (M+H)$^+$, found 308.1549.

Pyrimidine-2-carboxylic acid (2-methylquinolin-8-yl)amide (HJC-6-60)

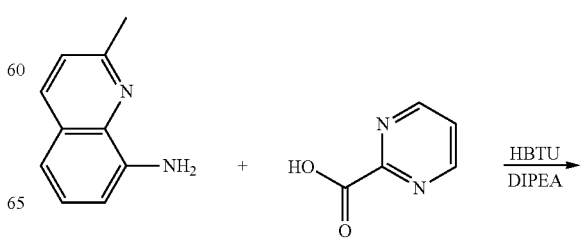

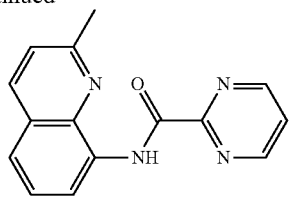

HJC-6-60

The title compound was prepared by the reaction of pyrimidine-2-carboxylic acid (30 mg, 0.24 mmol) and 2-methylquinolin-8-ylamine (32 mg, 0.2 mmol) according to the general procedure. Purification by a silica gel column (EtOAc/hexane=1:3) afforded the desired compound (40 mg, yield 76%) as a pale yellow solid (mp 172-173° C.). HPLC purity 99.9% ($t_R$=19.30 min). $^1$H NMR (600 MHz, CDCl$_3$) δ 12.26 (s, 1H), 9.01-9.03 (m, 3H), 8.05 (d, 1H, J=8.4 Hz), 7.51-7.55 (m, 2H), 7.49 (t, 1H, J=5.4 Hz), 7.34 (d, 1H, J=8.4 Hz), 2.82 (s, 3H). $^{13}$C NMR (150 MHz, CDCl$_3$) δ 160.3, 158.5, 157.8, 157.7, 138.6, 136.5, 133.7, 126.5, 126.3, 122.6, 122.5, 122.3, 117.4, 25.6. HRMS (ESI) calcd for $C_{15}H_{13}N_4O$ 265.1084 (M+H)$^+$, found 265.1093.

5-Methylpyrazine-2-carboxylic acid (6-methoxyquinolin-8-yl)amide (HJC-6-63)

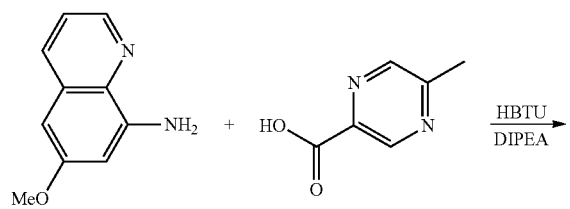

HJC-6-63

The title compound was prepared by the reaction of 5-methylpyrazine-2-carboxylic acid (82 mg, 0.6 mmol) and 6-methoxyquinolin-8-ylamine (35 mg, 0.2 mmol) according to the general procedure. Purification by a silica gel column (EtOAc/hexane=1:1) afforded the desired compound (50 mg, yield 85%) as a white solid (mp 213-214° C.). HPLC purity 99.8% ($t_R$=21.25 min). $^1$H NMR (600 MHz, CDCl$_3$) δ 11.94 (s, 1H), 8.76 (d, 1H, J=4.2 Hz), 8.70 (d, 1H, J=2.4 Hz), 8.56 (s, 1H), 8.04 (d, 1H, J=8.4 Hz), 7.41-7.43 (m, 1H), 6.85 (d, 1H, J=2.4 Hz), 3.96 (s, 3H), 2.69 (s, 3H). $^{13}$C NMR (150 MHz, CDCl$_3$) δ 161.8, 158.5, 157.4, 146.3, 143.8, 142.8, 142.6, 135.9, 135.1, 135.0, 129.2, 122.3, 109.5, 100.7, 55.8, 22.1. HRMS (ESI) calcd for $C_{16}H_{15}N_4O$ 295.1190 (M+H)$^+$, found 295.1199.

N-(6-Chloroquinolin-8-yl)pyrazine-2-carboxamide (HJC-7-92)

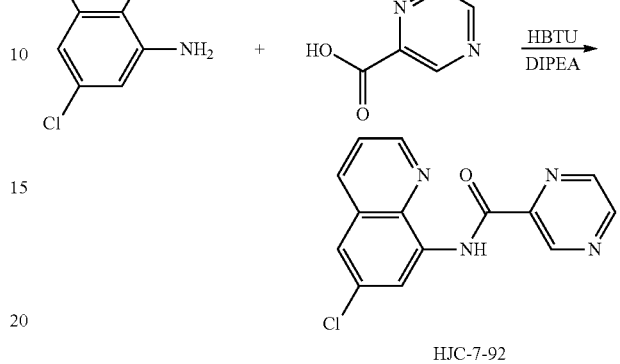

HJC-7-92

The title compound was prepared by the reaction of pyrazine-2-carboxylic acid (19 mg, 0.15 mmol) and 6-chloroquinolin-8-ylamine (18 mg, 0.10 mmol) according to the general procedure. Purification by a silica gel column (EtOAc/hexane=1:1) afforded the desired compound (25 mg, yield 89%) as a white solid. HPLC purity 99.2% ($t_R$=21.82 min). $^1$H NMR (600 MHz, CDCl$_3$) δ 12.02 (s, 1H), 9.56 (d, J=1.4 Hz, 1H), 9.01 (d, J=2.2 Hz, 1H), 8.92 (dd, J=4.2, 1.6 Hz, 1H), 8.75 (dd, J=2.4, 1.5 Hz, 1H), 8.11 (dd, J=8.3, 1.5 Hz, 1H), 7.58 (d, J=2.2 Hz, 1H), 7.52 (dd, J=8.3, 4.2 Hz, 1H). $^{13}$C NMR (150 MHz, CDCl$_3$) δ 161.4, 148.8, 147.6, 144.8, 144.8, 142.9, 137.7, 135.5, 135.0, 133.3, 128.5, 122.7, 121.0, 118.0. HRMS (ESI) calcd for $C_{14}H_{10}N_4OCl$ 285.0543 (M+H)$^+$, found 285.0534.

N-(6-Chloroquinolin-8-yl)-5-methylpyrazine-2-carboxamide (HJC-7-93)

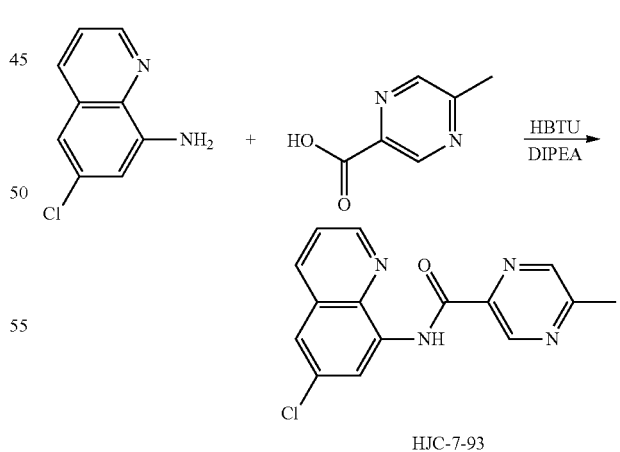

HJC-7-93

The title compound was prepared by reaction of 5-methyl pyrazine-2-carboxylic acid (21 mg, 0.15 mmol) and 6-chloroquinolin-8-ylamine (18 mg, 0.10 mmol) according to the general procedure. Purification by a silica gel column (EtOAc/hexane=1:1) afforded the desired compound (24 mg, yield 80%) as a white solid. HPLC purity 96.7%

($t_R$=22.61 min). $^1$H NMR (600 MHz, CDCl$_3$) δ 11.95 (s, 1H), 9.41 (s, 1H), 9.00 (d, J=2.1 Hz, 1H), 8.91 (dd, J=4.2, 1.5 Hz, 1H), 8.59 (s, 1H), 8.09 (dd, J=8.2, 1.2 Hz, 1H), 7.55 (d, J=2.1 Hz, 1H), 7.50 (dd, J=8.3, 4.2 Hz, 1H). NMR (150 MHz, CDCl$_3$) δ 161.82, 157.52, 148.75, 143.75, 142.72, 142.22, 137.74, 135.44, 135.22, 133.38, 128.56, 122.68, 120.81, 117.90, 21.97. HRMS (ESI) calcd for C$_{15}$H$_{12}$N$_4$OCl 299.0700 (M+H)$^+$, found 299.0692.

N-(6-Chloroquinolin-8-yl)pyrimidine-2-carboxamide (HJC-7-94)

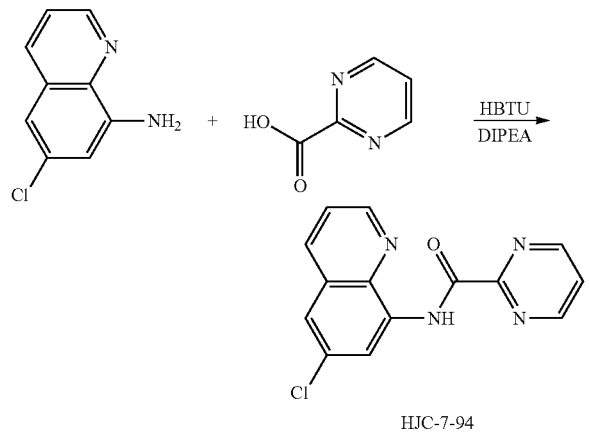

HJC-7-94

The title compound was prepared by reaction of pyrimidine-2-carboxylic acid (20 mg, 0.15 mmol) and 6-chloroquinolin-8-ylamine (18 mg, 0.10 mmol) according to the general procedure. Purification by a silica gel column (EtOAc/hexane=1:1) afforded the desired compound (25 mg, yield 81%) as a white solid. HPLC purity 99.5% ($t_R$=19.87 min). $^1$H NMR (300 MHz, CDCl$_3$) δ 12.26 (s, 1H), 9.09 (dd, J=7.9, 3.5 Hz, 3H), 8.96 (d, J=3.9 Hz, 1H), 8.14 (d, J=8.1 Hz, 1H), 7.61 (d, J=2.2 Hz, 1H), 7.55 (dd, J=10.0, 5.0 Hz, 2H). $^{13}$C NMR (75 MHz, CDCl$_3$) δ 158.12, 157.92, 157.23, 148.81, 135.61, 135.35, 132.65, 129.94, 123.66, 122.35, 114.90, 108.83. HRMS (ESI) calcd for C$_{14}$H$_{10}$N$_4$OCl 285.0534 (M+H)$^+$, found 285.0536.

N-(3-Methoxynaphthalen-1-yl)pyrazine-2-carboxamide (CTW-107)

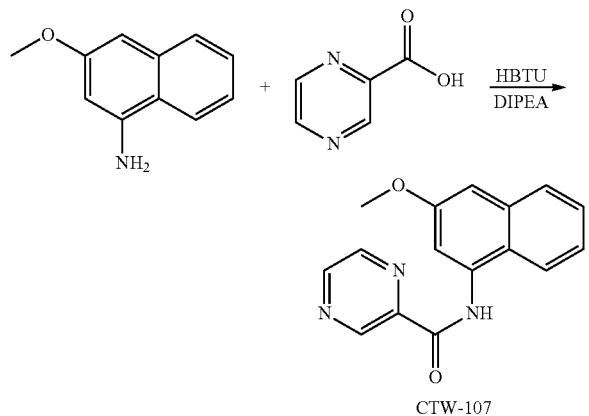

CTW-107

DIPEA (129 mg, 1.0 mmol) was added dropwise with stirring to a solution of 3-methoxynaphthalen-1-amine (25 mg, 0.14 mmol) and pyrazine-2-carboxylic acid (74 mg, 0.6 mmol) at rt in CH$_2$Cl$_2$ (3 mL). HBTU (227 mg, 0.6 mmol) was then added as a solid to the reaction mixture under an atmosphere of nitrogen at 0° C. and the reaction mixture was stirred at rt overnight. The crude reaction mixture was washed with water (10 mL) and extracted with ethyl acetate (2×25 mL). The organic layer was dried over anhydrous Na$_2$SO$_4$, filtered, and concentrated under reduced pressure. A silica gel column (hexane/ethyl acetate=3:1, v/v) afforded CTW-107 (32.9 mg, yield 84%) as a white wax-like solid. HPLC purity 96.5% ($t_R$=20.16 min). $^1$H NMR (300 MHz, CDCl$_3$) δ 12.01 (s, 1H), 9.56 (d, 1H, J=1.5 Hz), 8.82 (d, 1H, J=2.4 Hz), 8.77 (dd, 1H, J=4.5, 1.8 Hz), 8.74 (dd, 1H, J=2.4, 1.5 Hz), 8.72 (d, 1H, J=2.7 Hz), 8.07 (dd, 1H, J=8.4, 1.5 Hz), 7.44 (dd, 1H, J=8.1, 4.2 Hz), 6.88 (d, 1H, 3.0 Hz), 3.97 (s, 3H). $^{13}$C NMR (75 MHz, CDCl$_3$) δ 161.3, 158.3, 147.4, 146.2, 145.1, 144.7, 142.9, 135.7, 135.0, 134.8, 129.1, 122.2, 109.6, 100.8, 55.7. HRMS (ESI) calcd for C$_{16}$H$_{13}$N$_3$O$_2$ (M+H)$^+$ 281.1033; found 281.1036.

N-(3-Methoxynaphthalen-1-yl)pyrimidine-2-carboxamide (CTW-113)

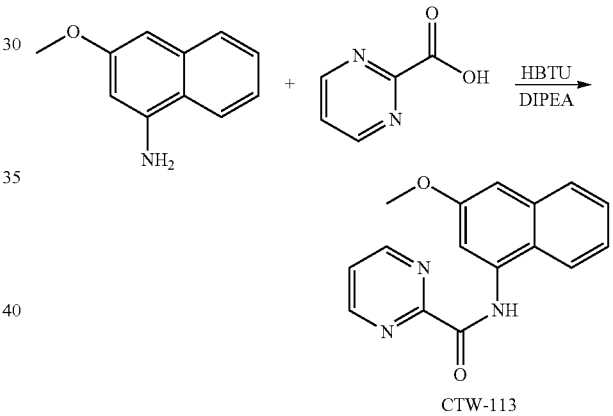

CTW-113

DIPEA (135 mg, 1.1 mmol) was added dropwise with stirring to a solution of 3-methoxynaphthalen-1-amine (36 mg, 0.21 mmol) and pyrazine-2-carboxylic acid (78 mg, 0.63 mmol) at rt in CH$_2$Cl$_2$ (3 mL). HBTU (239 mg, 0.63 mmol) was then added as a solid to the reaction mixture under an atmosphere of nitrogen at 0° C. and the reaction mixture was stirred at rt overnight. The crude reaction mixture was washed with water (10 mL) and extracted with ethyl acetate (2×25 mL). The organic layer was dried over anhydrous Na$_2$SO$_4$, filtered, and concentrated under reduced pressure. A silica gel column (hexane/ethyl acetate=3:1, v/v) afforded CTW-113 (32.9 mg, yield 84%) as a white wax-like solid. HPLC purity 99.5% ($t_R$=18.55 min). $^1$H NMR (300 MHz, CDCl$_3$) δ 12.01 (s, 1H), 9.14 (d, 2H, J=5.1 Hz), 8.84 (dd, 1H, J=4.2, 1.8 Hz), 8.57 (d, 1H, J=2.7 Hz), 8.35 (dd, 1H, J=8.4, 1.8 Hz), 7.82 (t, 1H, J=5.1), 7.64 (dd, 1H, J=8.4, 4.2 Hz), 7.19 (d, 1H, J=2.7 Hz), 3.94 (s, 3H). $^{13}$C NMR (75 MHz, CDCl$_3$) δ 160.3, 158.7, 158.0, 157.4, 147.1, 136.0, 135.1, 135.0, 133.9, 129.5, 124.1, 123.3, 109.1, 101.1, 56.1. HRMS (ESI) calcd for C$_{16}$H$_{13}$N$_3$O$_2$ (M+H)$^+$ 281.1033; found 281.1035.

Pyrimidine-2-carboxylic acid (6-methoxy-quinolin-8-yl)-amide (NY0134)

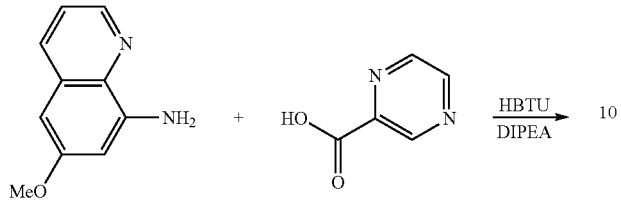

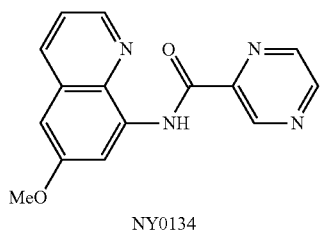

The title compound was prepared by reaction of 6-methoxy-quinolin-8-ylamine (82 mg, 0.47 mmol) and pyrazine-2-carboxylic acid (175 mg, 1.41 mmol) according to the general procedure. Purification by a silica gel column (EtOAc/hexane=2:1) afforded the desired compound (87 mg, yield 67%) as a white solid. HPLC purity 96.0% ($t_R$=19.96 min). $^1$H NMR (300 MHz, CDCl$_3$) δ 11.97 (s, 1H), 9.54 (d, J=1.5 Hz, 1H), 8.81 (d, J=2.5 Hz, 1H), 8.77-8.71 (m, 2H), 8.69 (d, J=2.7 Hz, 1H), 8.04 (dd, J=8.2, 1.6 Hz, 1H), 7.41 (dd, J=8.3, 4.2 Hz, 1H), 6.85 (d, J=2.7 Hz, 1H), 3.96 (s, 3H). $^{13}$C NMR (75 MHz, CDCl$_3$) δ 161.24, 158.29, 147.30, 146.13, 145.06, 144.62, 142.84, 135.66, 134.91, 134.80, 129.03, 122.15, 109.50, 100.71, 55.61. HRMS (ESI) calcd for C$_{15}$H$_{13}$N$_4$O$_2$ 281.1033 (M+H)$^+$, found 281.1027.

Pyrazine-2-carboxylic acid [6-(2-morpholin-4-yl-ethoxy)-quinolin-8-yl]-amide (NY0137)

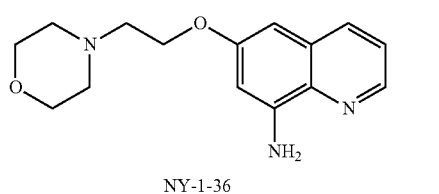

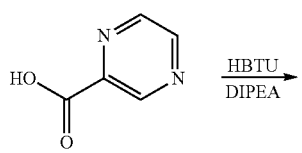

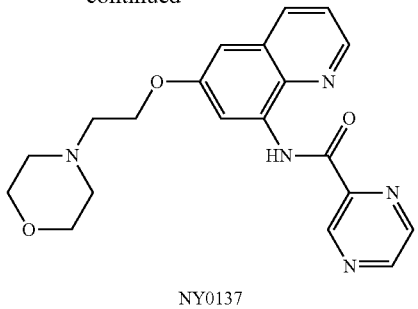

The title compound was prepared by the reaction of 6-(2-morpholin-4-yl-ethoxy)-quinolin-8-ylamine NY-1-36 (45 mg, 0.16 mmol) and pyrazine-2-carboxylic acid (25 mg, 0.20 mmol) according to the general procedure. Purification by a silica gel column (EtOAc/MeOH/Et$_3$N=50:1:0.5) afforded the desired compound (40 mg, yield 65%) as a yellow solid. HPLC purity 96.4% ($t_R$=21.33 min). $^1$H NMR (300 MHz, CDCl$_3$) δ 12.00 (s, 1H), 9.55 (d, J=1.4 Hz, 1H), 8.86-8.71 (m, 4H), 8.05 (dd, J=8.3, 1.6 Hz, 1H), 7.44 (dd, J=8.3, 4.3 Hz, 1H), 6.88 (d, J=2.7 Hz, 1H), 4.28 (t, J=5.6 Hz, 2H), 3.80-3.74 (m, 2H), 2.90 (t, J=5.6 Hz, 2H), 2.70-2.60 (m, 4H). $^{13}$C NMR (75 MHz, CDCl$_3$) δ 161.31, 157.38, 147.36, 146.27, 145.04, 144.64, 142.87, 135.71, 134.96, 134.85, 129.03, 122.21, 109.80, 101.56, 66.96, 66.43, 57.57, 54.18. HRMS (ESI) calcd for C$_{20}$H$_{22}$N$_5$O$_3$ 380.1717 (M+H)$^+$, found 380.1712.

5-Methyl-pyrazine-2-carboxylic acid [6-(2-morpholin-4-yl-ethoxy)-quinolin-8-yl]-amide (NY0138)

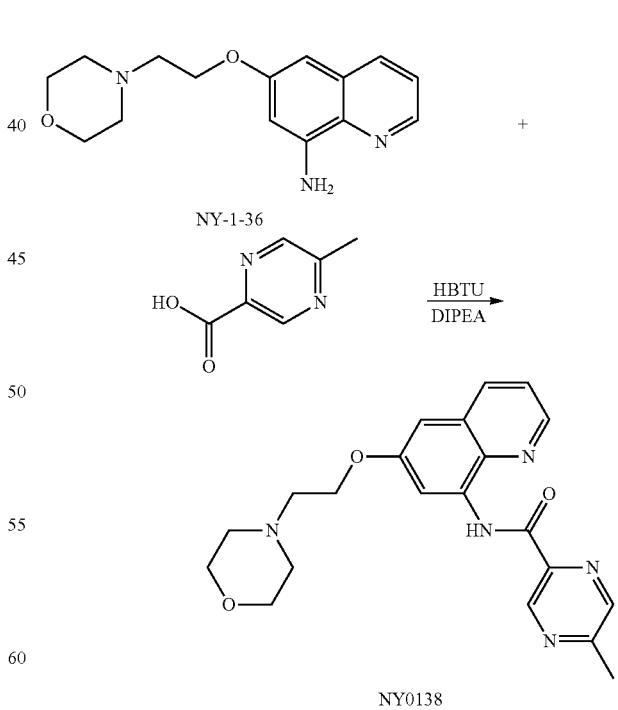

The title compound was prepared by the reaction of 6-(2-morpholin-4-yl-ethoxy)-quinolin-8-ylamine NY-1-36 (40 mg, 0.16 mmol) and 5-methyl-pyrazine-2-carboxylic acid (27 mg, 0.20 mmol) according to the general procedure.

Purification by a silica gel column (EtOAc/MeOH/Et₃N=50:1:0.5) afforded the desired compound (35 mg, yield 62%) as a white solid. HPLC purity 97.1% (t$_R$=22.23 min). ¹H NMR (300 MHz, CDCl₃) δ 11.95 (s, 1H), 9.42 (d, J=1.4 Hz, 1H), 8.78 (dd, J=4.2, 1.6 Hz, 1H), 8.73 (d, J=2.6 Hz, 1H), 8.59 (dd, J=1.4, 0.6 Hz, 1H), 8.05 (dd, J=8.3, 1.6 Hz, 1H), 7.44 (dd, J=8.3, 4.2 Hz, 1H), 6.88 (d, J=2.7 Hz, 1H), 4.29 (t, J=5.6 Hz, 2H), 3.82-3.74 (m, 4H), 2.91 (t, J=5.6 Hz, 2H), 2.71 (s, 3H), 2.69-2.61 (m, 4H). ¹³C NMR (75 MHz, CDCl₃) δ 161.70, 157.41, 157.24, 146.23, 143.61, 142.64, 142.38, 135.73, 135.03, 134.94, 129.03, 122.16, 109.65, 101.46, 66.96, 66.44, 57.58, 54.19, 21.92. HRMS (ESI) calcd for C₁₁H₂₄N₅O₃ 394.1874 (M+H)⁺, found 394.1868.

Pyrazine-2-carboxylic acid quinolin-6-yl ester (NY0142)

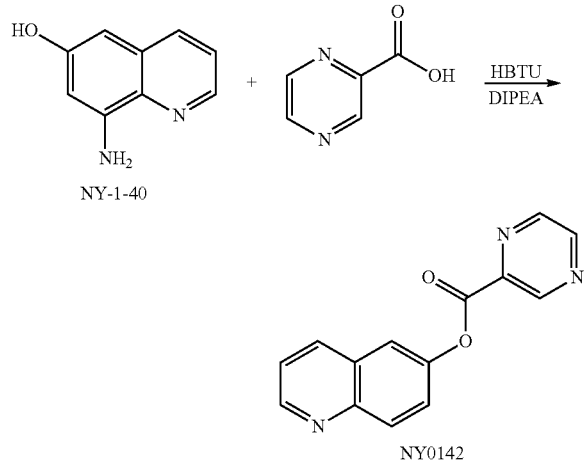

Coupling of NY-1-40 (28 mg) with pyrazine-2-carboxylic acid in the presence of HBTU and DIPEA in DCM at rt produced NY0142 (20 mg, yield 45%) as a white solid. HPLC purity 96.8% (t$_R$=15.63 min). ¹H NMR (300 MHz, CDCl₃) δ 9.51 (d, J=1.4 Hz, 1H), 8.90-8.84 (m, 2H), 8.78 (dd, J=4.2, 1.7 Hz, 1H), 8.08 (dd, J=8.4, 1.7 Hz, 1H), 7.43 (dd, J=8.3, 4.2 Hz, 1H), 7.08 (d, J=2.4 Hz, 1H), 6.84 (d, J=2.4 Hz, 1H). ¹³C NMR (75 MHz, CDCl₃) δ 148.10, 147.36, 146.78, 145.69, 144.64, 143.09, 135.93, 129.02, 122.17, 106.36, 103.96. HRMS (ESI) calcd for C₁₄H₁₁N₄O₂ 267.0877 (M+H)⁺, found 267.0872.

Pyrazine-2-carboxylic acid [6-(2-fluoro-ethoxy)-quinolin-8-yl]amide (NY0144)

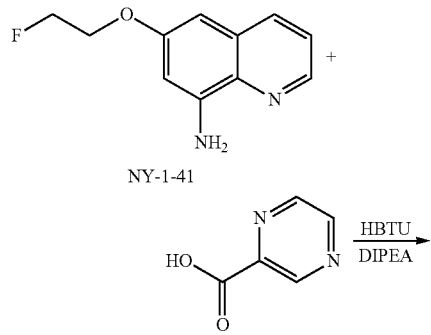

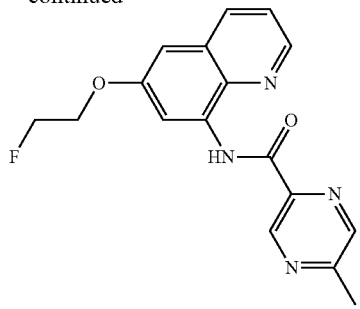

NY0144

The title compound was prepared by reaction of 6-(2-fluoro-ethoxy)-quinolin-8-yl amine NY-1-41 (36 mg, 0.17 mmol) and pyrazine-2-carboxylic acid (24 mg, 0.19 mmol) according to the general procedure. Purification by a silica gel column (EtOAc/Hexane=1:2) afforded the desired compound (52 mg, yield 96%) as a yellow solid. HPLC purity 96.5% (t$_R$=19.78 min). ¹H NMR (300 MHz, CDCl₃) δ 11.99 (s, 1H), 9.55 (d, J=1.5 Hz, 1H), 8.82 (d, J=2.5 Hz, 1H), 8.78 (dd, J=4.2, 1.6 Hz, 1H), 8.77-8.72 (m, 2H), 8.05 (dd, J=8.3, 1.6 Hz, 1H), 7.44 (dd, J=8.3, 4.2 Hz, 1H), 6.89 (d, J=2.7 Hz, 1H), 4.96-4.90 (m, 1H), 4.80-4.74 (m, 1H), 4.47-4.41 (m, 1H), 4.37-4.32 (m, 1H). ¹³C NMR (75 MHz, CDCl₃) δ 161.29, 157.04, 147.36, 146.47, 145.01, 144.65, 142.85, 135.77, 135.02, 128.92, 122.27, 109.40, 101.98, 82.91, 80.64, 67.60, 67.32. HRMS (ESI) calcd for C₁₆H₁₄FN₄O₂ 313.1095 (M+H)⁺, found 313.1090.

Pyrazine-2-carboxylic acid [6-(2-dimethylamino-ethoxy)-quinolin-8-yl]-amide (NY0147)

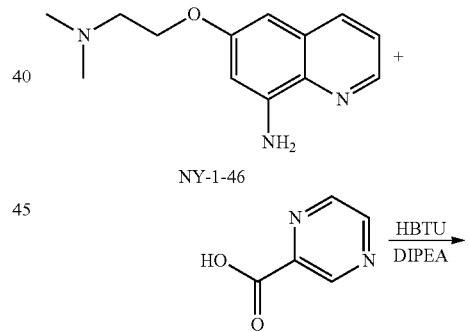

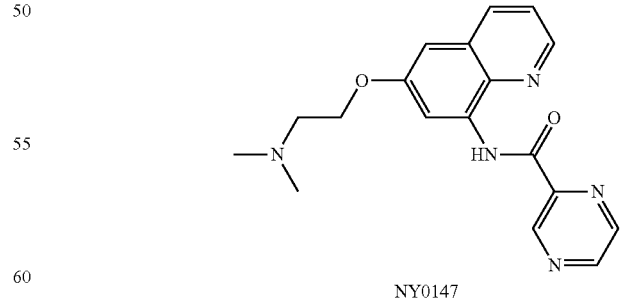

NY0147

The title compound was prepared by the reaction of 6-(2-dimethylamino-ethoxy)-quinolin-8-ylamine NY-1-46 (33 mg, 0.14 mmol) and pyrazine-2-carboxylic acid (21 mg, 0.17 mmol) according to the general procedure. Purification by a silica gel column (EtOAc/MeOH/Et₃N=100:1:1)

afforded the desired compound (35 mg, yield 73%) as a yellow oil. HPLC purity 99.0% ($t_R$=15.60 min). $^1$H NMR (300 MHz, CDCl$_3$) δ 11.98 (s, 1H), 9.54 (s, 1H), 8.81 (s, 1H), 8.75 (d, J=9.2 Hz, 3H), 8.04 (d, J=8.7 Hz, 1H), 7.46-7.39 (m, 1H), 6.88 (s, 1H), 4.24 (t, J=5.3 Hz, 2H), 2.84 (t, J=5.3 Hz, 2H), 2.40 (s, 6H). $^{13}$C NMR (75 MHz, CDCl$_3$) δ 161.23, 157.47, 147.31, 146.20, 145.07, 144.63, 142.85, 134.96, 134.79, 129.02, 122.16, 109.82, 101.58, 66.59, 58.15, 45.97. HRMS (ESI) calcd for $C_{18}H_{20}N_5O_2$ 338.1612 (M+H)$^+$, found 338.1611.

5-Methyl-pyrazine-2-carboxylic acid [6-(2-dimethylamino-ethoxy)-quinolin-8-yl]-amide (NY0148)

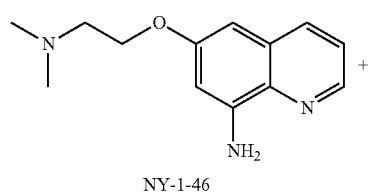

NY-1-46

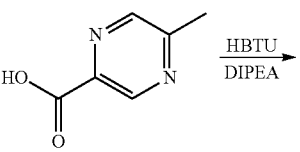

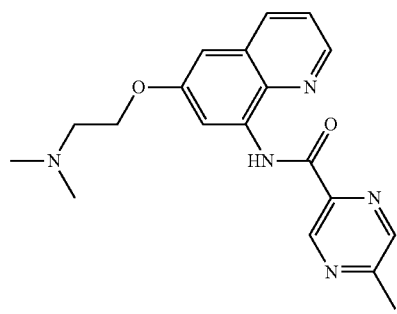

NY0148

The title compound was prepared by the reaction of 6-(2-dimethylamino-ethoxy)-quinolin-8-ylamine NY-1-46 (33 mg, 0.14 mmol) and 5-methyl-pyrazine-2-carboxylic acid (24 mg, 0.17 mmol) according to the general procedure. Purification by a silica gel column (EtOAc/MeOH/Et$_3$N=100:1:1) afforded the desired compound (28 mg, yield 56%) as a white solid. HPLC purity 97.6% ($t_R$=16.28 min). $^1$H NMR (300 MHz, CDCl$_3$) δ 11.94 (s, 1H), 9.42 (d, J=2.1 Hz, 1H), 8.85-8.69 (m, 2H), 8.59 (s, 1H), 8.05 (d, J=8.3 Hz, 1H), 7.43 (dd, J=8.2, 4.1 Hz, 1H), 6.89 (d, J=2.7 Hz, 1H), 4.25 (td, J=5.8, 1.9 Hz, 2H), 2.84 (td, J=5.6, 1.8 Hz, 2H), 2.71 (d, J=2.3 Hz, 3H), 2.48-2.33 (m, 6H). $^{13}$C NMR (75 MHz, CDCl$_3$) δ 161.64, 157.53, 157.18, 146.16, 143.61, 142.62, 142.42, 135.71, 134.96, 129.03, 122.11, 109.68, 101.50, 66.65, 58.18, 46.00, 21.91. HRMS (ESI) calcd for $C_{19}H_{22}N_5O_2$ 352.1768 (M+H)$^+$, found 352.1765.

(2-{8-[(Pyrazine-2-carbonyl)amino]quinolin-6-yloxy}ethyl)carbamic acid tert-butyl ester (NY0151)

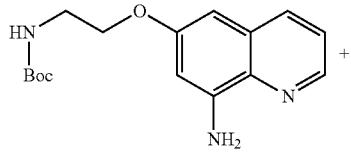

NY-1-50

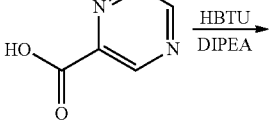

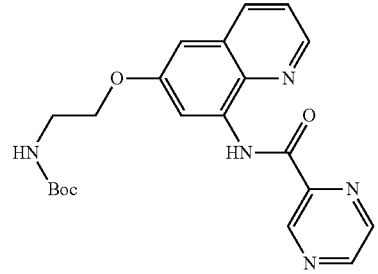

NY0151

The title compound was prepared by the reaction of [2-(8-aminoquinolin-6-yloxy)ethyl]carbamic acid tert-butyl ester NY-1-50 (75 mg, 0.25 mmol) and pyrazine-2-carboxylic acid (77 mg, 0.62 mmol) according to the general procedure. Purification by a silica gel column (EtOAc/Hexane=1:2) afforded the desired compound (81 mg, yield 80%) as a yellow oil. HPLC purity 97.4% ($t_R$=16.28 min). $^1$H NMR (300 MHz, CDCl$_3$) δ 11.96 (s, 1H), 9.54 (s, 1H), 8.75 (m, 4H), 8.03 (d, J=8.1 Hz, 1H), 7.48-7.36 (m, 1H), 6.83 (s, 1H), 5.21 (s, 1H), 4.17 (t, J=5.3 Hz, 2H), 3.63 (t, J=5.4 Hz, 2H), 1.47 (s, 9H). $^{13}$C NMR (75 MHz, CDCl$_3$) δ 161.30, 157.17, 155.95, 147.36, 146.33, 145.00, 144.64, 142.86, 135.75, 134.99, 134.86, 128.97, 122.24, 109.77, 101.15, 79.56, 67.48, 40.04, 28.40. HRMS (ESI) calcd for $C_{11}H_{24}N_5O_4$ 410.1823 (M+H)$^+$, found 410.1822.

(2-{8-[(5-Methylpyrazine-2-carbonyl)amino]quinolin-6-yloxy}ethyl)carbamic acid tert-butyl ester (NY0152)

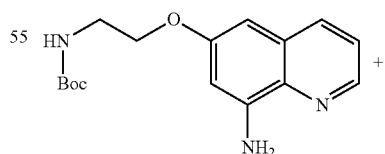

NY-1-50

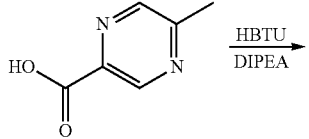

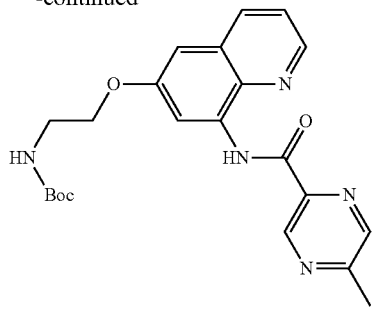

NY0152

The title compound was prepared by the reaction of [2-(8-amino-quinolin-6-yloxy)ethyl]carbamic acid tert-butyl ester NY-1-50 (75 mg, 0.25 mmol) and 5-methyl-pyrazine-2-carboxylic acid (86 mg, 0.62 mmol) according to the general procedure. Purification by a silica gel column (EtOAc/Hexane=1:2) afforded the desired compound (58 mg, yield 56%) as a colorless oil. HPLC purity 95.1% ($t_R$=21.40 min). $^1$H NMR (300 MHz, CDCl$_3$) δ 11.91 (s, 1H), 9.39 (s, 1H), 8.76 (s, 1H), 8.67 (s, 1H), 8.57 (s, 1H), 8.03 (d, J=8.2 Hz, 1H), 6.82 (s, 1H), 5.19 (s, 1H), 4.24-4.09 (m, 2H), 3.69-3.56 (m, 2H), 2.70 (s, 3H), 1.47 (s, 9H). $^{13}$C NMR (75 MHz, CDCl$_3$) δ 161.69, 157.24, 157.19, 155.94, 146.28, 143.59, 142.63, 142.33, 135.77, 135.03, 134.97, 128.97, 122.19, 109.63, 101.03, 79.55, 67.47, 40.05, 28.39, 21.91. HRMS (ESI) calcd for $C_{22}H_{26}N_5O_4$ 424.1979 (M+H)$^+$, found 424.1978.

(2-{8-[(Pyrimidine-2-carbonyl)amino]quinolin-6-yloxy}ethyl)carbamic acid tert-butyl ester (NY0153)

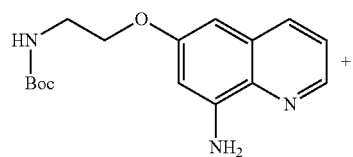

NY-1-50

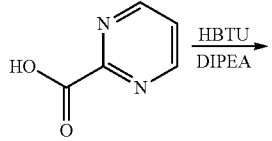

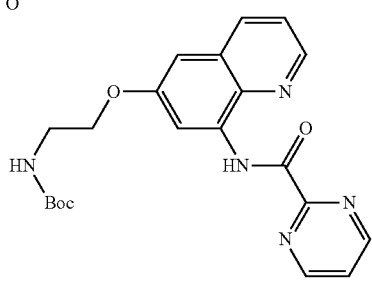

NY0153

The title compound was prepared by the reaction of [2-(8-aminoquinolin-6-yloxy)ethyl]carbamic acid tert-butyl ester NY-1-50 (75 mg, 0.25 mmol) and pyrimidine-2-carboxylic acid (77 mg, 0.62 mmol) according to the general procedure. Purification by a silica gel column (EtOAc/Hexane=2:1) afforded the desired compound (53 mg, yield 52%) as a colorless oil. HPLC purity 95.4% ($t_R$=19.63 min). $^1$H NMR (300 MHz, CDCl$_3$) δ 12.17 (s, 1H), 9.04 (d, J=2.5 Hz, 2H), 8.70 (d, J=19.3 Hz, 2H), 7.99 (d, J=8.2 Hz, 1H), 7.53 (td, J=4.6, 2.2 Hz, 1H), 7.45-7.36 (m, 1H), 6.79 (s, 1H), 5.29 (s, 1H), 4.23-4.10 (m, 2H), 3.70-3.53 (m, 2H), 1.46 (s, 9H). $^{13}$C NMR (75 MHz, CDCl$_3$) δ 160.36, 157.82, 157.16, 156.01, 146.27, 135.63, 134.97, 134.82, 128.90, 122.74, 122.17, 110.00, 101.14, 79.57, 67.49, 40.01, 28.40. HRMS (ESI) calcd for $C_{21}H_{24}N_5O_4$ 410.1823 (M+H)$^+$, found 410.1827.

4-(2-{8-[(Pyrazine-2-carbonyl)amino]quinolin-6-yloxy}ethyl)piperidine-1-carboxylic acid tert-butyl ester (NY0159)

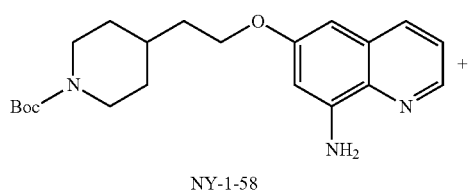

NY-1-58

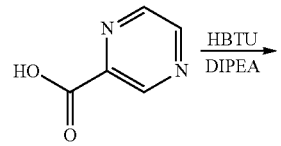

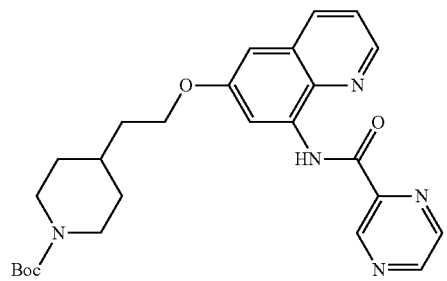

NY0159

The title compound was prepared by the reaction of 4-[2-(8-aminoquinolin-6-yloxy)ethyl]piperidine-1-carboxylic acid tert-butyl ester NY-1-58 (100 mg, 0.33 mmol) and pyrazine-2-carboxylic acid (81 mg, 0.66 mmol) according to the general procedure. Purification by a silica gel column (EtOAc/Hexane=2:1) afforded the desired compound (110 mg, yield 78%) as a light yellow oil. HPLC purity 97.3% ($t_R$=24.88 min). $^1$H NMR (300 MHz, CDCl$_3$) δ 11.99 (s, 1H), 9.58-9.52 (m, 1H), 8.81 (s, 1H), 8.73 (t, J=9.4 Hz, 3H), 8.03 (d, J=7.8 Hz, 1H), 7.48-7.37 (m, 1H), 6.85 (s, 1H), 4.25-4.01 (m, 4H), 2.74 (t, J=13.0 Hz, 2H), 1.74 (m, 5H), 1.46 (s, 9H), 1.31-1.15 (m, 2H). $^{13}$C NMR (75 MHz, CDCl$_3$) δ 161.30, 157.61, 154.84, 147.35, 146.14, 145.04, 144.61, 142.87, 135.62, 134.89, 134.79, 129.08, 122.18, 109.79, 101.31, 79.24, 65.65, 35.71, 32.92, 32.09, 28.47, 21.93. HRMS (ESI) calcd for $C_{26}H_{32}N_5O_4$ 478.2449 (M+H)$^+$, found 478.2447.

125

(2-{8-[(5-Methylpyrazine-2-carbonyl)amino]quinolin-6-yloxy}ethyl)carbamic acid tert-butyl ester (NY0160)

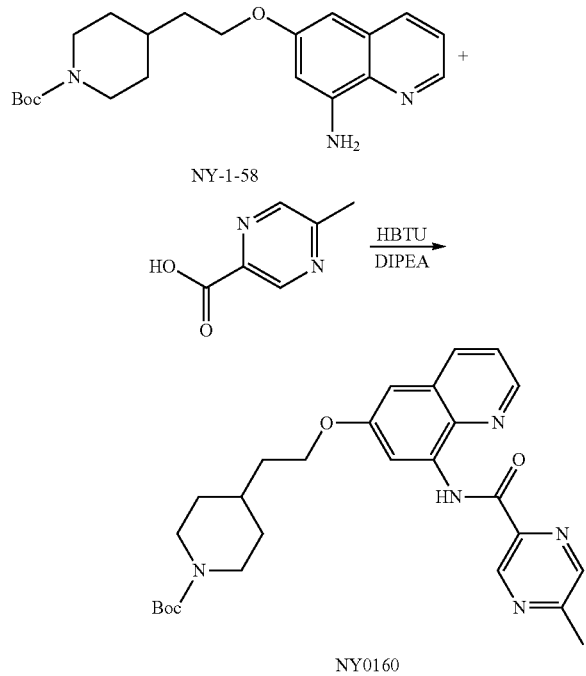

The title compound was prepared by the reaction of 4-[2-(8-aminoquinolin-6-yloxy)ethyl]piperidine-1-carboxylic acid tert-butyl ester NY-1-58 (100 mg, 0.33 mmol) and 5-methylpyrazine-2-carboxylic acid (91 mg, 0.66 mmol) according to the general procedure. Purification by a silica gel column (EtOAc/Hexane=1:2) afforded the desired compound (101 mg, yield 77%) as a light yellow oil. HPLC purity 96.4% ($t_R$=25.43 min). $^1$H NMR (300 MHz, CDCl$_3$) δ 11.91 (s, 1H), 9.37 (s, 1H), 8.71 (d, J=15.9 Hz, 2H), 8.55 (s, 1H), 8.01 (d, J=8.3 Hz, 1H), 7.46-7.35 (m, 1H), 6.82 (s, 1H), 4.11 (m, 4H), 2.80-2.76 (m, 2H), 2.67 (s, 3H), 1.75 (m, 5H), 1.45 (s, 9H), 1.30-1.19 (m, 2H). $^{13}$C NMR (75 MHz, CDCl$_3$) δ 161.66, 157.60, 157.20, 154.82, 146.07, 143.53, 142.61, 142.33, 135.60, 134.93, 134.84, 129.05, 122.11, 109.60, 101.17, 79.20, 65.63, 38.56, 35.70, 32.93, 32.08, 28.45, 21.88. HRMS (ESI) calcd for $C_{27}H_{34}N_5O_4$ 492.2605 (M+H)$^+$, found 492.2610.

4-(2-{8-[(Pyrimidine-2-carbonyl)amino]quinolin-6-yloxy}ethyl)piperidine-1-carboxylic acid tert-butyl ester (NY0161)

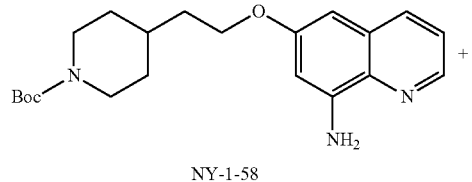

126

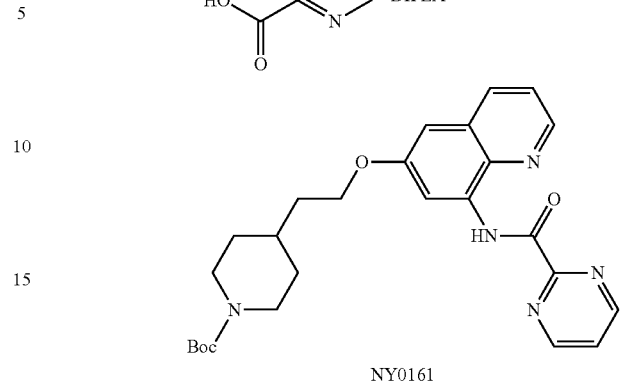

The title compound was prepared by the reaction of 4-[2-(8-aminoquinolin-6-yloxy)ethyl]piperidine-1-carboxylic acid tert-butyl ester NY-1-58 (100 mg, 0.33 mmol) and pyrimidine-2-carboxylic acid (81 mg, 0.66 mmol) according to the general procedure. Purification by a silica gel column (EtOAc/Hexane=2:1) afforded the desired compound (98 mg, yield 76%) as a light yellow oil. HPLC purity 97.0% ($t_R$=23.30 min). $^1$H NMR (300 MHz, CDCl$_3$) δ 12.17 (s, 1H), 9.04-8.92 (m, 2H), 8.72 (s, 2H), 8.00 (d, J=8.2 Hz, 1H), 7.49 (t, J=4.6 Hz, 1H), 6.82 (s, 1H), 4.20-3.98 (m, 4H), 2.69 (d, J=12.7 Hz, 2H), 1.77 (m, 5H), 1.44 (s, 9H), 1.24-1.12 (m, 2H). $^{13}$C NMR (75 MHz, CDCl$_3$) δ 160.21, 157.94, 157.83, 157.72, 157.62, 154.81, 146.09, 135.53, 134.91, 134.87, 129.02, 122.62, 122.12, 109.94, 101.35, 79.18, 65.69, 38.55, 35.64, 32.86, 32.05, 28.45. HRMS (ESI) calcd for $C_{26}H_{32}N_5O_4$ 478.2454 (M+H)$^+$, found 478.2456.

General Procedure for the Boc-Deprotection:

To a solution of the responding Boc-protected compound in DCM (4 mL) was added TFA (1 mL) at 0° C. The mixture was stirred at 0° C. for 2 hr. Part of the solvent was removed, and then the residue was adjusted to pH7-8 with sat. NaHCO$_3$ solution (aq.). The solid was filter and dried over anhydrous Na$_2$SO$_4$ to give the desired product without further purification.

Pyrazine-2-carboxylic acid [6-(2-aminoethoxy)quinolin-8-yl]amide (NY0154)

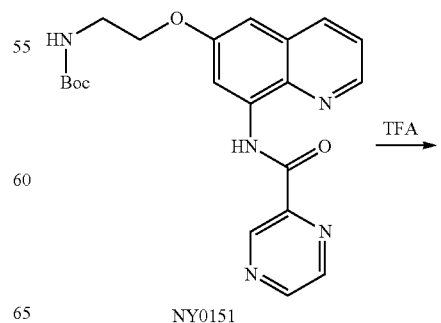

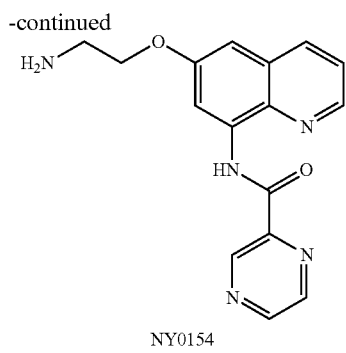

NY0154

The title compound was prepared from NY0151 (60 mg, 0.15 mmol) according to the general Boc-deprotection procedure and the desired compound (43 mg, yield 95%) was obtained as a white solid. HPLC purity 97.4% ($t_R$=14.59 min). $^1$H NMR (300 MHz, CD$_3$OD/D$_2$O) δ 9.27 (s, 1H), 8.85 (s, 1H), 8.74 (m, 2H), 8.45 (s, 1H), 8.28-8.16 (m, 1H), 7.54 (dd, J=8.6, 4.3 Hz, 1H), 7.11 (s, 1H), 4.45 (d, J=5.3 Hz, 2H), 3.54 (t, J=5.2 Hz, 2H). $^{13}$C NMR (75 MHz, CD$_3$OD/D$_2$O) δ 166.60, 161.50, 156.05, 147.53, 146.97, 144.47, 143.81, 143.11, 135.51, 133.97, 129.05, 122.70, 109.28, 102.00, 64.30, 38.98. HRMS (ESI) calcd for C$_{16}$H$_{16}$N$_5$O$_2$ 310.1299 (M+H)$^+$, found 310.1300.

5-Methylpyrazine-2-carboxylic acid [6-(2-aminoethoxy)quinolin-8-yl]amide (NY0156)

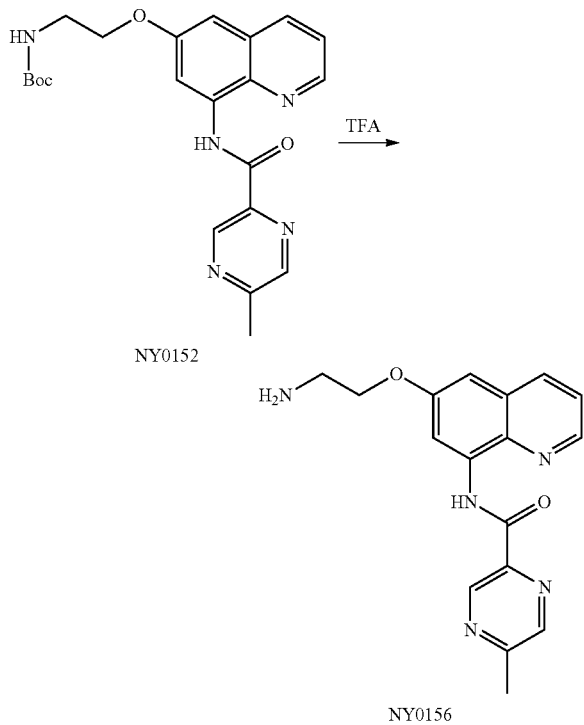

The title compound was prepared from NY0152 (40 mg, 0.10 mmol) according to the general Boc-deprotection procedure and the desired compound (25 mg, yield 84%) was obtained as a light pink solid. HPLC purity 96.0% ($t_R$=15.14 min). $^1$H NMR (300 MHz, CD$_3$OD/D$_2$O) δ 9.07 (s, 1H), 8.73 (d, J=3.5 Hz, 1H), 8.55 (s, 1H), 8.47 (s, 1H), 8.20 (d, J=8.3 Hz, 1H), 7.56 (d, J=5.7 Hz, 1H), 7.09 (s, 1H), 4.42 (t, J=4.6 Hz, 2H), 3.52 (d, J=5.1 Hz, 2H), 2.63 (s, 3H). $^{13}$C NMR (75 MHz, CD$_3$OD/D$_2$O) δ 161.79, 157.84, 156.10, 146.92, 143.53, 141.96, 141.77, 135.38, 135.33, 134.16, 129.00, 122.64, 109.09, 101.71, 64.24, 38.88, 20.42. HRMS (ESI) calcd for C$_{17}$H$_{18}$N$_5$O$_2$ 310.1299 (M+H)$^+$, found 324.1457.

Pyrimidine-2-carboxylic acid [6-(2-aminoethoxy)quinolin-8-yl]amide (NY0162)

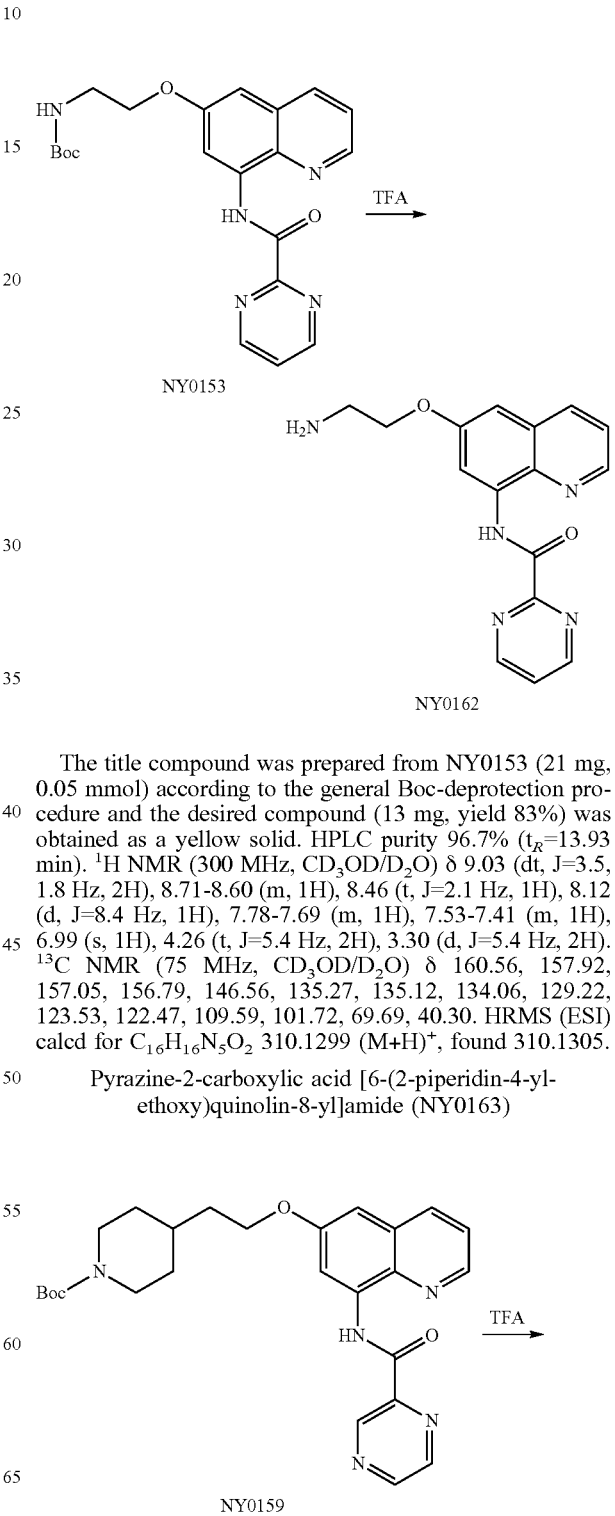

The title compound was prepared from NY0153 (21 mg, 0.05 mmol) according to the general Boc-deprotection procedure and the desired compound (13 mg, yield 83%) was obtained as a yellow solid. HPLC purity 96.7% ($t_R$=13.93 min). $^1$H NMR (300 MHz, CD$_3$OD/D$_2$O) δ 9.03 (dt, J=3.5, 1.8 Hz, 2H), 8.71-8.60 (m, 1H), 8.46 (t, J=2.1 Hz, 1H), 8.12 (d, J=8.4 Hz, 1H), 7.78-7.69 (m, 1H), 7.53-7.41 (m, 1H), 6.99 (s, 1H), 4.26 (t, J=5.4 Hz, 2H), 3.30 (d, J=5.4 Hz, 2H). $^{13}$C NMR (75 MHz, CD$_3$OD/D$_2$O) δ 160.56, 157.92, 157.05, 156.79, 146.56, 135.27, 135.12, 134.06, 129.22, 123.53, 122.47, 109.59, 101.72, 69.69, 40.30. HRMS (ESI) calcd for C$_{16}$H$_{16}$N$_5$O$_2$ 310.1299 (M+H)$^+$, found 310.1305.

Pyrazine-2-carboxylic acid [6-(2-piperidin-4-yl-ethoxy)quinolin-8-yl]amide (NY0163)

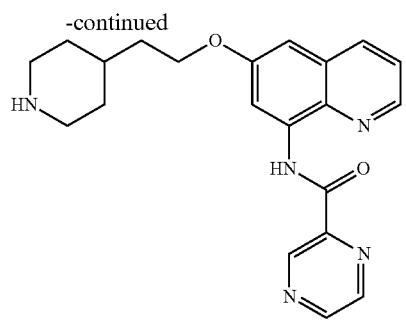

NY0163

The title compound was prepared from NY0159 (30 mg, 0.05 mmol) according to the general Boc-deprotection procedure and the desired compound (19 mg, yield 83%) was obtained as a yellow solid. HPLC purity 97.3% ($t_R$=16.74 min). $^1$H NMR (300 MHz, CD$_3$OD/CDCl$_3$) δ 9.37 (s, 1H), 8.82 (s, 1H), 8.76 (s, 1H), 8.68 (t, J=3.3 Hz, 1H), 8.49 (s, 1H), 8.10 (d, J=8.3 Hz, 1H), 7.45 (dt, J=8.1, 3.3 Hz, 1H), 6.93 (s, 1H), 4.14 (t, J=4.2 Hz, 2H), 3.05 (d, J=12.3 Hz, 2H), 2.61 (dd, J=13.6, 10.9 Hz, 2H), 1.81 (d, J=12.6 Hz, 5H), 1.29 (d, J=13.8 Hz, 2H). $^{13}$C NMR (75 MHz, CD$_3$OD/CDCl$_3$) δ 161.25, 157.36, 147.35, 146.03, 144.85, 143.59, 143.33, 135.32, 134.88, 134.25, 129.20, 122.13, 109.57, 101.12, 78.20, 77.76, 77.33, 65.60, 45.76, 36.02, 33.02, 32.63. HRMS (ESI) calcd for C$_{21}$H$_{24}$N$_5$O$_2$ 378.1925 (M+H)$^+$, found 378.1922.

5-Methylpyrazine-2-carboxylic acid [6-(2-piperidin-4-yl-ethoxy)quinolin-8-yl]amide (NY0164)

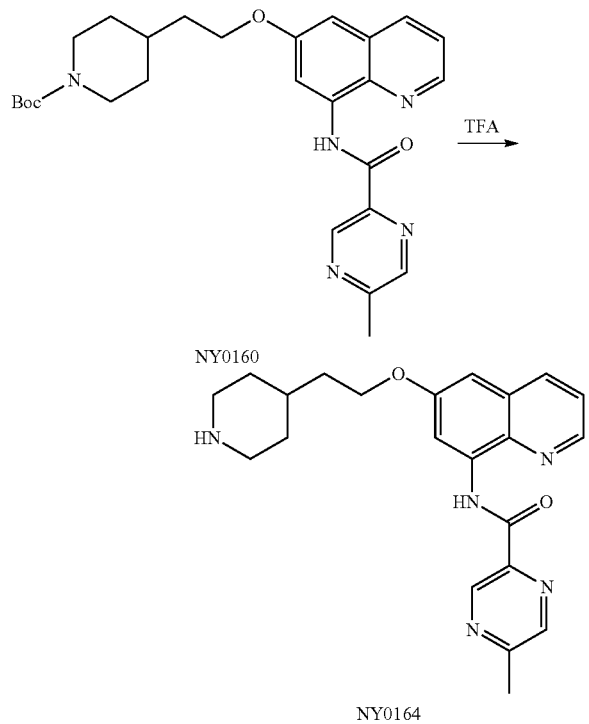

The title compound was prepared from NY0160 (43 mg, 0.09 mmol) according to the general Boc-deprotection procedure and the desired compound (30 mg, yield 88%) was obtained as a yellow solid. HPLC purity 97.1% ($t_R$=17.33 min). $^1$H NMR (300 MHz, CD$_3$OD/CDCl$_3$) δ 9.13 (s, 1H), 8.65 (d, J=3.6 Hz, 1H), 8.58 (s, 1H), 8.41 (d, J=1.9 Hz, 1H), 8.08 (d, J=8.3 Hz, 1H), 7.49-7.40 (m, 1H), 6.89 (s, 1H), 4.12 (t, J=5.9 Hz, 2H), 3.06 (d, J=12.5 Hz, 2H), 2.72-2.55 (m, 5H), 1.80 (d, J=13.6 Hz, 5H), 1.36-1.14 (m, 2H). $^{13}$C NMR (75 MHz, CD$_3$OD/CDCl$_3$) δ 161.56, 157.54, 157.25, 146.14, 143.32, 142.26, 142.09, 135.19, 134.98, 134.15, 129.15, 122.23, 109.48, 101.21, 78.18, 77.75, 77.31, 65.68, 45.59, 35.91, 32.87, 32.41, 20.58. HRMS (ESI) calcd for C$_{22}$H$_{26}$N$_5$O$_2$ 392.2081 (M+H)$^+$, found 392.2086.

Pyrimidine-2-carboxylic acid [6-(2-piperidin-4-yl-ethoxy)quinolin-8-yl]amide (NY0165)

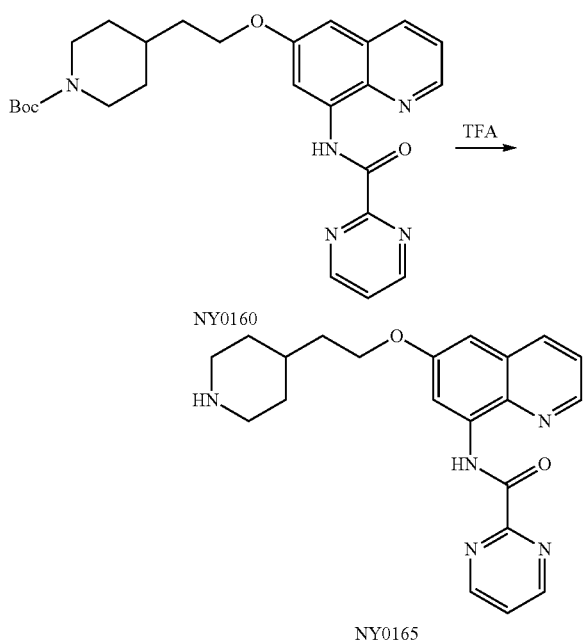

The title compound was prepared from NY0161 (40 mg, 0.08 mmol) according to the general Boc-deprotection procedure and the desired compound (25 mg, yield 81%) was obtained as a yellow solid. HPLC purity 97.0% ($t_R$=23.30 min). $^1$H NMR (300 MHz, CD$_3$OD/CDCl$_3$/D$_2$O) δ 9.05 (d, J=5.5 Hz, 2H), 8.70 (d, J=3.8 Hz, 1H), 8.51 (d, J=3.1 Hz, 1H), 8.11 (d, J=8.3 Hz, 1H), 7.72 (t, J=5.3 Hz, 1H), 7.47 (s, 1H), 6.93 (d, J=3.1 Hz, 1H), 4.17 (d, J=7.1 Hz, 2H), 3.23 (d, J=12.4 Hz, 2H), 2.79 (t, J=12.5 Hz, 2H), 1.98-1.77 (m, 5H), 1.40 (m, 2H). $^{13}$C NMR (75 MHz, CD$_3$OD/CDCl$_3$/D$_2$O) δ 160.47, 157.90, 157.15, 156.97, 146.37, 135.19, 135.12, 134.21, 129.20, 123.44, 122.35, 109.70, 101.56, 78.16, 77.73, 77.30, 65.64, 44.85, 35.39, 32.04, 30.74. HRMS (ESI) calcd for C$_{21}$H$_{24}$N$_5$O$_2$ 378.1925 (M+H)$^+$, found 378.1925.

Having now fully described the invention, it will be understood by those of skill in the art that the same can be performed within a wide and equivalent range of conditions, formulations, and other parameters without affecting the scope of the invention or any embodiment thereof. All patents, patent applications and publications cited herein are fully incorporated by reference herein in their entirety.

INCORPORATION BY REFERENCE

The entire disclosure of each of the patent documents and scientific articles referred to herein is incorporated by reference for all purposes.

EQUIVALENTS

The invention may be embodied in other specific forms without departing from the spirit or essential characteristics thereof. The foregoing embodiments are therefore to be considered in all respects illustrative rather than limiting the invention described herein. Scope of the invention is thus indicated by the appended claims rather than by the foregoing description, and all changes that come within the meaning and range of equivalency of the claims are intended to be embraced therein.

We claim:
1. A compound selected from the group consisting of:

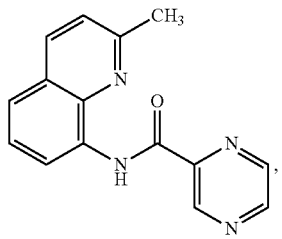,

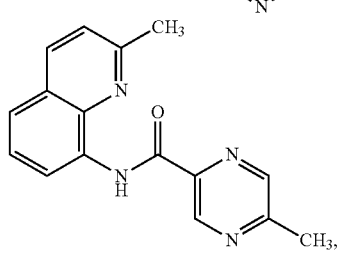,

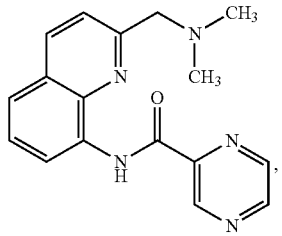,

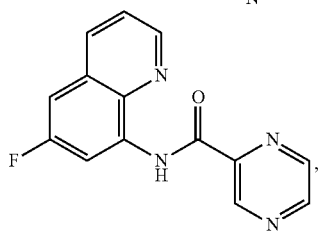,

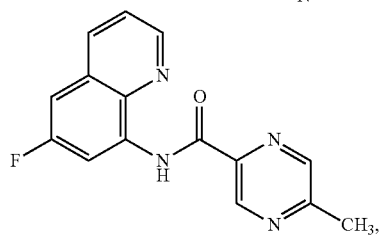,

-continued

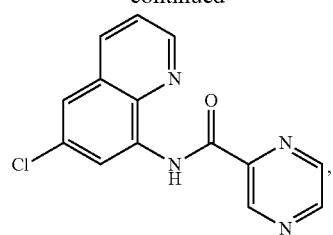,

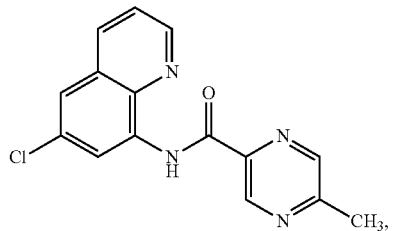,

,

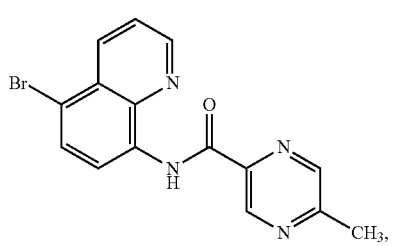,

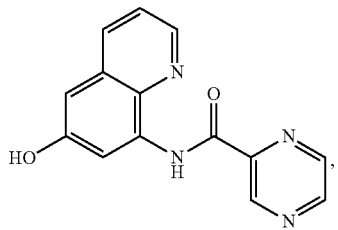,

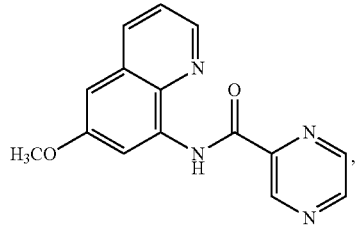,

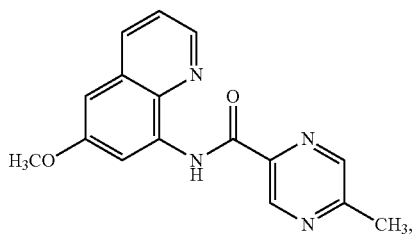,

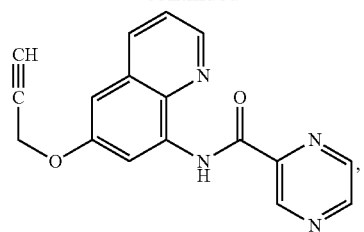,
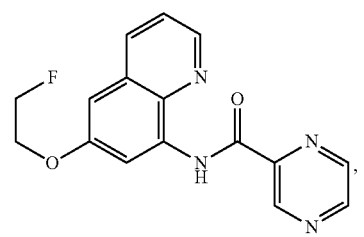,
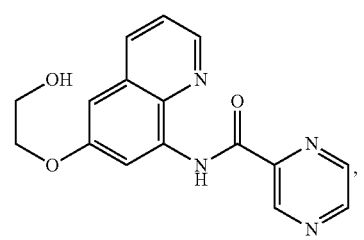,
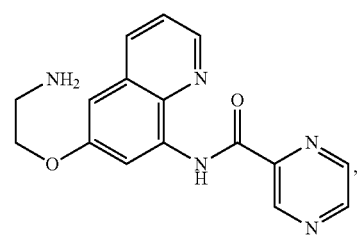,
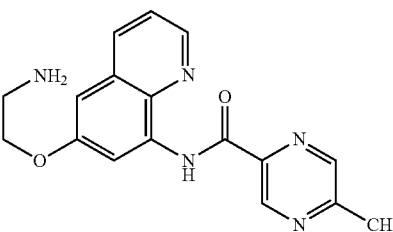,
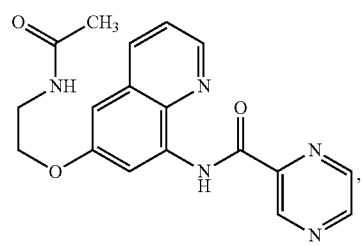,
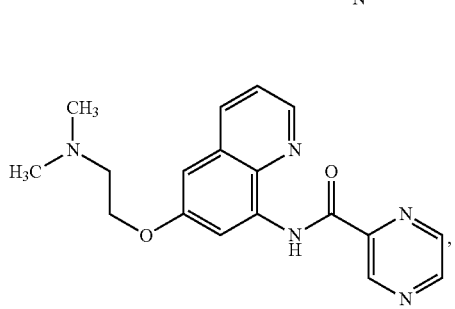,
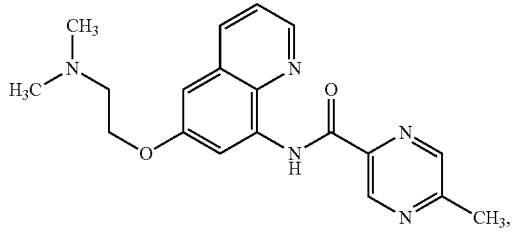,
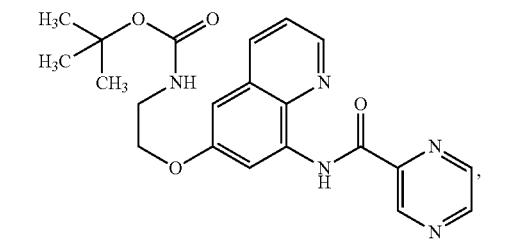,
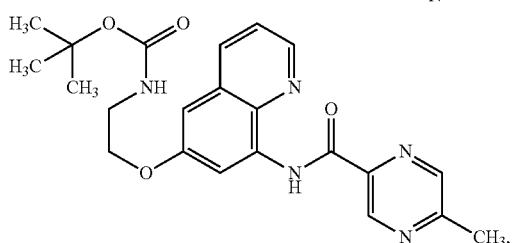,
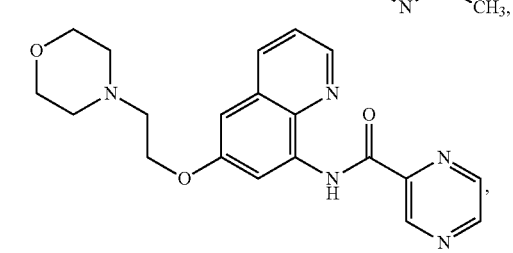,
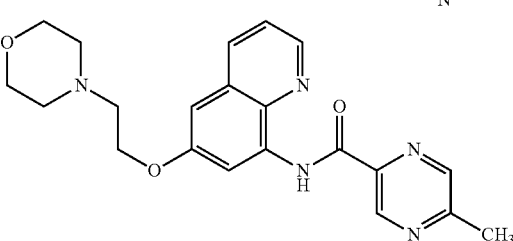,
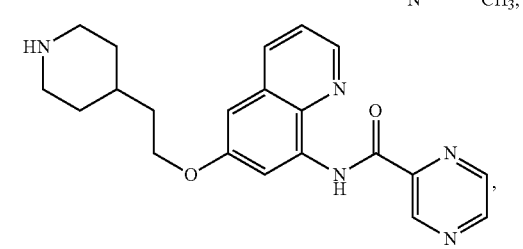,
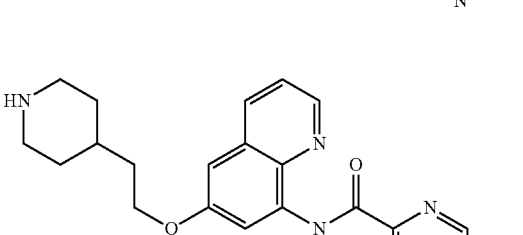, or a pharmaceutically acceptable salt thereof.

2. A pharmaceutical composition comprising a pharmaceutically acceptable carrier and a compound of claim 1, or a pharmaceutically acceptable salt thereof.

3. A kit comprising a compound of claim 1, or a pharmaceutically acceptable salt thereof, and instructions for administering the compound to a patient having a hyperproliferative disease.

4. The kit of claim 3, wherein the hyperproliferative disease is cancer.

5. The kit of claim 4, wherein the cancer is pancreatic cancer.

6. The kit of claim 4, wherein the kit further comprises one or more anticancer agents.

7. The kit of claim 6, wherein the compound is administered together with the one or more anticancer agents.

8. A method for inhibiting cancer cell proliferation in a patient, comprising administering to a patient in need thereof a therapeutically effective amount of the pharmaceutical composition of claim 2.

9. The method of claim 8, wherein the cancer cell is a pancreatic cancer cell.

10. The method of claim 8, wherein the patient is a human.

11. The method of claim 8, wherein the method further comprises administering to the patient one or more anticancer agents.

12. The method of claim 11, wherein the one or more anticancer agents is selected from the group consisting of a chemotherapeutic agent and radiation therapy.

* * * * *